(12) United States Patent
Evans et al.

(10) Patent No.: US 8,097,007 B2
(45) Date of Patent: Jan. 17, 2012

(54) SELF-ANCHORING SLING AND INTRODUCER SYSTEM

(75) Inventors: Douglas G. Evans, Snellville, GA (US); Ken Butcher, Conyers, GA (US); Michele Gandy Davis, Forsyth, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 2140 days.

(21) Appl. No.: 10/633,254

(22) Filed: Aug. 1, 2003

(65) Prior Publication Data
US 2004/0144395 A1  Jul. 29, 2004

Related U.S. Application Data

(60) Provisional application No. 60/400,616, filed on Aug. 2, 2002, provisional application No. 60/479,039, filed on Jun. 17, 2003.

(51) Int. Cl.
*A61B 17/08* (2006.01)
*A61F 2/02* (2006.01)
*A61F 13/00* (2006.01)

(52) U.S. Cl. .............. 606/151; 600/30; 600/37

(58) Field of Classification Search .......... 606/151, 606/222, 223, 224, 139, 144, 148, 107; 600/29, 600/30, 37, 38; 112/222–224, 48, 49; 24/16 PB, 24/301, 328, 335, 336, 338; 81/487, 489, 81/491; 30/322; 174/102 R
See application file for complete search history.

(56) References Cited

U.S. PATENT DOCUMENTS

| | | | |
|---|---|---|---|
| 1,450,101 A | | 3/1923 | Mathewson |
| 2,097,018 A | | 10/1937 | Chamberlin |
| 2,427,176 A | * | 9/1947 | Aldeen .............. 439/883 |
| 3,126,600 A | * | 3/1964 | De Marre .............. 24/301 |
| 3,913,179 A | | 10/1975 | Rhee |
| 4,172,458 A | | 10/1979 | Pereyra |
| 4,409,866 A | * | 10/1983 | McBride .............. 81/491 |
| 4,509,516 A | * | 4/1985 | Richmond .............. 606/144 |
| 4,655,221 A | | 4/1987 | Devereux |
| 4,775,380 A | | 10/1988 | Seedhom et al. |

(Continued)

FOREIGN PATENT DOCUMENTS
DE  102 11 360  10/2003
(Continued)

OTHER PUBLICATIONS

International Search Report for appln. PCT/03/24212 (May 24, 2004).

(Continued)

*Primary Examiner* — Julian Woo
(74) *Attorney, Agent, or Firm* — Rutan & Tucker, LLP

(57) ABSTRACT

A system for supporting the urethra using an introducer needle, the ends of which are flattened and which have openings therethrough, a handle having a latch mechanism which engages the opening in the flattened portion of the first end of the introducer needle, an implant, and a connector joining the end of the implant to the flattened portion of one of the ends of the introducer needle. These components are used to draw the implant into position, either through vaginal or abdominal incisions, to form a U-shaped loop beneath the urethra. The ends of the implant are adjusted to provide proper support for the urethra. The implant can have slits that open under applied tensile force.

1 Claim, 46 Drawing Sheets

U.S. PATENT DOCUMENTS

| | | | | |
|---|---|---|---|---|
| 4,784,139 | A | 11/1988 | Demos | |
| 4,799,484 | A * | 1/1989 | Smith et al. | 606/223 |
| 4,911,164 | A | 3/1990 | Roth | |
| 4,938,760 | A | 7/1990 | Burton et al. | |
| 5,013,292 | A | 5/1991 | Lemay | |
| 5,112,344 | A | 5/1992 | Petros | |
| 5,123,910 | A | 6/1992 | McIntosh | |
| 5,149,329 | A | 9/1992 | Richardson | |
| 5,234,436 | A * | 8/1993 | Eaton et al. | 606/107 |
| 5,356,432 | A | 10/1994 | Rutkow et al. | |
| 5,362,294 | A | 11/1994 | Seitzinger | |
| 5,439,467 | A | 8/1995 | Benderev et al. | |
| 5,473,796 | A * | 12/1995 | Fusillo | 24/338 |
| 5,474,543 | A | 12/1995 | McKay | |
| 5,562,689 | A | 10/1996 | Green et al. | |
| 5,647,836 | A | 7/1997 | Blake, III et al. | |
| 5,655,270 | A * | 8/1997 | Boisvert | 24/336 |
| 5,689,860 | A * | 11/1997 | Matoba et al. | 24/335 |
| 5,693,072 | A | 12/1997 | McIntosh | |
| 5,774,994 | A * | 7/1998 | Stein et al. | 30/322 |
| 5,830,220 | A | 11/1998 | Wan et al. | |
| 5,840,011 | A | 11/1998 | Landgrebe et al. | |
| 5,860,425 | A | 1/1999 | Benderev et al. | |
| 5,899,909 | A | 5/1999 | Claren et al. | |
| 5,904,692 | A | 5/1999 | Steckel et al. | |
| 5,934,283 | A | 8/1999 | Willem et al. | |
| 5,971,967 | A | 10/1999 | Willard | |
| 6,005,191 | A * | 12/1999 | Tzeng et al. | 174/102 R |
| 6,030,393 | A | 2/2000 | Corlew | |
| 6,042,534 | A * | 3/2000 | Gellman et al. | 600/30 |
| 6,042,536 | A | 3/2000 | Tihon et al. | |
| 6,063,094 | A | 5/2000 | Rosenberg | |
| 6,068,591 | A | 5/2000 | Bruckner et al. | |
| 6,110,101 | A | 8/2000 | Tihon et al. | |
| 6,197,036 | B1 | 3/2001 | Tripp et al. | |
| 6,221,060 | B1 | 4/2001 | Willard | |
| 6,273,852 | B1 * | 8/2001 | Lehe et al. | 600/30 |
| 6,306,079 | B1 | 10/2001 | Trabucco | |
| 6,336,731 | B1 * | 1/2002 | Chien | 81/491 |
| 6,382,214 | B1 | 5/2002 | Raz et al. | |
| 6,406,423 | B1 | 6/2002 | Scetbon | |
| 6,440,154 | B2 | 8/2002 | Gellman et al. | |
| 6,475,139 | B1 | 11/2002 | Miller | |
| 6,491,703 | B1 | 12/2002 | Ulmsten | |
| 6,612,977 | B2 | 9/2003 | Staskin et al. | |
| 6,638,210 | B2 | 10/2003 | Berger | |
| 6,638,211 | B2 | 10/2003 | Suslian et al. | |
| 6,675,483 | B2 * | 1/2004 | Bond et al. | 30/322 |
| 6,689,047 | B2 | 2/2004 | Gellman | |
| 6,755,781 | B2 * | 6/2004 | Gellman | 600/38 |
| 7,063,716 | B2 * | 6/2006 | Cunningham | 606/222 |
| 2001/0049467 | A1 | 12/2001 | Lehe et al. | |
| 2001/0053916 | A1 | 12/2001 | Rioux | |
| 2002/0007222 | A1 | 1/2002 | Desai | |
| 2002/0028980 | A1 | 3/2002 | Thierfelder et al. | |
| 2002/0052653 | A1 | 5/2002 | Durgin | |
| 2002/0058959 | A1 | 5/2002 | Gellman | |
| 2002/0072694 | A1 | 6/2002 | Snitkin et al. | |
| 2002/0077526 | A1 | 6/2002 | Kammerer et al. | |
| 2002/0099258 | A1 | 7/2002 | Staskin et al. | |
| 2002/0147382 | A1 | 10/2002 | Neisz et al. | |
| 2002/0151762 | A1 | 10/2002 | Rocheleau et al. | |
| 2002/0188169 | A1 | 12/2002 | Kammerer et al. | |
| 2003/0023136 | A1 | 1/2003 | Raz et al. | |
| 2003/0023138 | A1 | 1/2003 | Luscombe | |
| 2003/0050530 | A1 | 3/2003 | Neisz et al. | |
| 2003/0065246 | A1 | 4/2003 | Inman et al. | |
| 2003/0171644 | A1 | 9/2003 | Anderson et al. | |
| 2003/0176762 | A1 | 9/2003 | Kammerer | |
| 2003/0176875 | A1 | 9/2003 | Anderson et al. | |
| 2003/0212305 | A1 | 11/2003 | Anderson et al. | |

FOREIGN PATENT DOCUMENTS

| | | | |
|---|---|---|---|
| EP | 0 437 481 | B | 3/1995 |
| EP | 0 745 351 | A | 12/1996 |
| EP | 0 556 313 | B | 3/1997 |
| EP | 0 740 925 | B | 3/1999 |
| EP | 0 778 749 | | 12/2000 |
| EP | 1 151 722 | A | 11/2001 |
| EP | 1 159 921 | A | 12/2001 |
| EP | 0 854 691 | B | 1/2002 |
| EP | 0 983 033 | A | 10/2002 |
| EP | 1 342 454 | | 9/2003 |
| WO | WO 90/03766 | | 4/1990 |
| WO | WO 96/06567 | | 3/1996 |
| WO | WO 97/13465 | | 4/1997 |
| WO | WO 98/35632 | | 8/1998 |
| WO | WO 00/18325 | | 4/2000 |
| WO | WO 00/27304 | | 5/2000 |
| WO | WO 00/66030 | | 11/2000 |
| WO | WO 00/74594 | A1 | 12/2000 |
| WO | WO 00/74613 | A1 | 12/2000 |
| WO | WO 00/74633 | A2 | 12/2000 |
| WO | WO 01/52750 | | 7/2001 |
| WO | WO 02/02031 | | 1/2002 |
| WO | WO 02/19946 | | 3/2002 |
| WO | WO 02/26108 | | 4/2002 |
| WO | WO 02/28312 | | 4/2002 |
| WO | WO 02/28315 | | 4/2002 |
| WO | WO 02/39914 | A1 | 5/2002 |
| WO | WO 02/058562 | A1 | 8/2002 |
| WO | WO 02/058563 | A1 | 8/2002 |
| WO | WO 02/058564 | A2 | 8/2002 |
| WO | WO 02/058565 | A2 | 8/2002 |
| WO | WO 02/062237 | | 8/2002 |
| WO | WO 02/065921 | A1 | 8/2002 |
| WO | WO 02/065922 | A1 | 8/2002 |
| WO | WO 02/065923 | A1 | 8/2002 |
| WO | WO 02/071931 | A1 | 9/2002 |
| WO | WO 02/098322 | A1 | 12/2002 |
| WO | WO 03/002027 | A1 | 1/2003 |
| WO | WO 03/013369 | A1 | 2/2003 |
| WO | WO 03/068107 | A1 | 8/2003 |
| WO | WO 03/075792 | A1 | 9/2003 |
| WO | WO 03/092546 | A2 | 11/2003 |
| WO | WO 03/096928 | | 11/2003 |
| WO | WO 03/096930 | | 11/2003 |
| WO | WO 2004/016196 | A2 | 2/2004 |
| WO | WO 2004/019786 | A1 | 3/2004 |

OTHER PUBLICATIONS

Written Opinion for appln. PCT/03/24212 (Aug. 24, 2004).
Bryans, Fred E.; "Marlex gauze hammock sling operation with Cooper's ligament attachment in the management of recurrent urinary stress incontinence" 1979.
Burch, John C.; "Urethrovaginal fixation to Cooper's ligament for correction of stress incontinence, cystocele, and prolapse" (publication date unknown).
Falconer, C., Ekman-Ordeberg, G., Malmstrom, A., Ulmsten, U.; "Clinical Outcome and Changes in Connective Tissue Metabolism After Intravaginal Slingplasty in Stress Incontinent Women"; The International Urogynecology Journal; 1996.
Falconer, C., Soderberg, M., Blomgren, B., Ulmsten, U.; "Influence of Different Sling Materials on Connective Tissue Metabolism in Stress Urinary Incontinent Women"; The International Urogynecology Journal; 2001.
Horbach, Nicolette S.; "Suburethral Sling Procedures"; Urogynecology and Urodynamics Theory and Practice Fourth Edition; 1996.
Karram, Mickey M., Bhatia, Narender N.; "Patch procedure: Modified Transvaginal Fascia Lata Sling for recurrent or severe stress urinary incontinence"; Mar. 1990.
Kersey J.; "The gauze hammock sling operation in the treatment of stress incontinence"; British Journal of Obstetrics and Gynaecology; vol. 90 pp. 945-949; Oct. 1983.
Korda, Andrew; Peat, Brian; Hunter, Peter; "Experience with Silastic Slings for Female Urinary Incontinence"; Aust NZ J Obstet Gynaecol 1989.
Lichtenstein, Irving L., Shulman, Alex G., Amid, Parviz K., Montllor, Michele M.; "The Tension-Free Hernioplasty"; The American Journal of Surgery vol. 157; Feb. 1989.
McIndoe, G.A.J., Jones, R.W., Grieve B.W.; "The Aldridge Sling Procedure in the Treatment of Urinary Stress Incontinence"; Aust NZ J Obstet Gynaecol; 1987.

Morgan, J.E.; "A sling operation, using Marlex polypropylene mesh, for treatment of recurrent strss incontinence"; (publication date unknown).

Narik, G., Palmrich, A.H.; "A simplified sling operation suitable for routine use"; (publication date unknown).

Nichols, David H.; "The Mersilene Mesh Gauze-Hammock For Severe Urinary Stress Incontinence"; Obstetrics and Gynecology; (publication date unknown).

Norris, Jeffrey P., Breslin, David S., Staskin, David R.; "Use of Synthetic Material in Sling Surgery: A Minimally Invasive Approach"; Journal of Endourology; vol. 10, No. 3, Jun. 1996.

O'Donnell, Pat D.; "Combined Raz Urethral Suspension and McGuire Pubovaginal Sling for Treatment of Complicated Stress Urinary Incontinence"; Jan. 1992.

Raz, Shlomo; Female Urology; Second Edition; 1996.

Ridley, John H.; "Appraisal of the Goebell-Frangenheim-Stoeckel sling procedure"; (publication date unknown).

Stanton, Stuart L.; "Suprapubic Approaches for Stress Incontinence in Women"; (publication date unknown).

Staskin, David R., Choe, Jong M., Breslin, David S.; "The Gore-Tex sling procedure for female sphincteric incontinence: indications, technique, and results"; World J. Urol.; 1997.

Choe, Jong M., Staskin, David R.; "Gore-Tex Patch Sling: 7 Years Later"; 1999.

Cook; Urogynecology; Product Technical Datasheet and Order form.

Walters, Mark D.; "Percutaneous Suburethral Slings: State of the Art"; (publication date unknown).

* cited by examiner

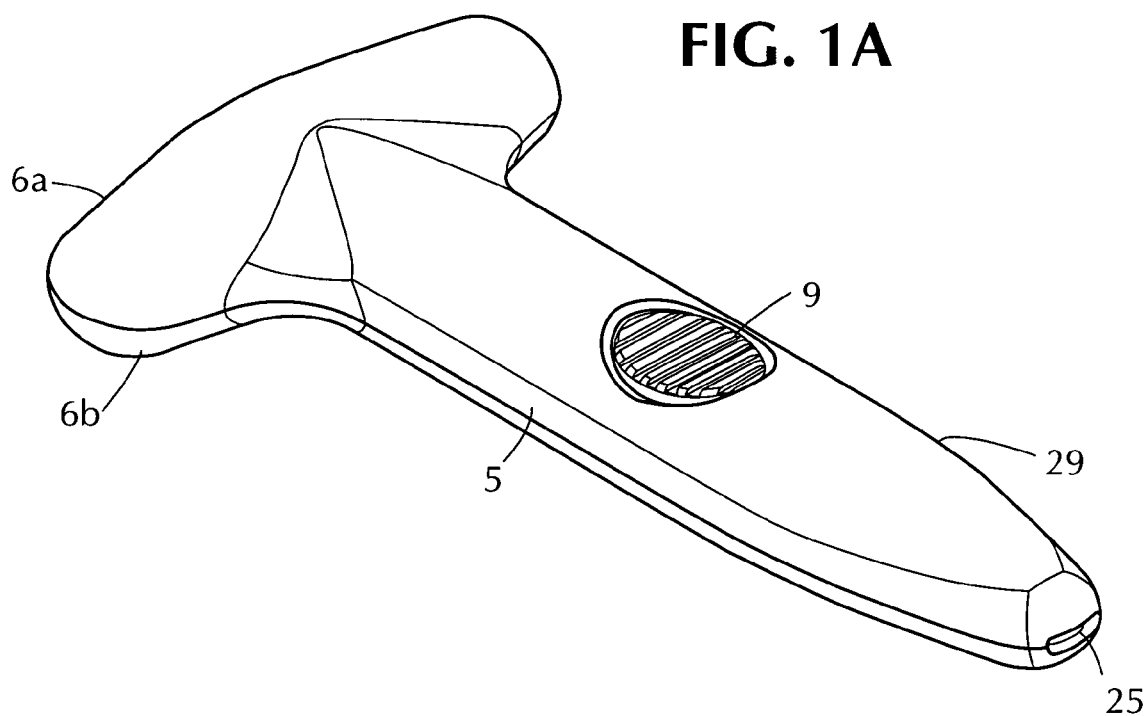
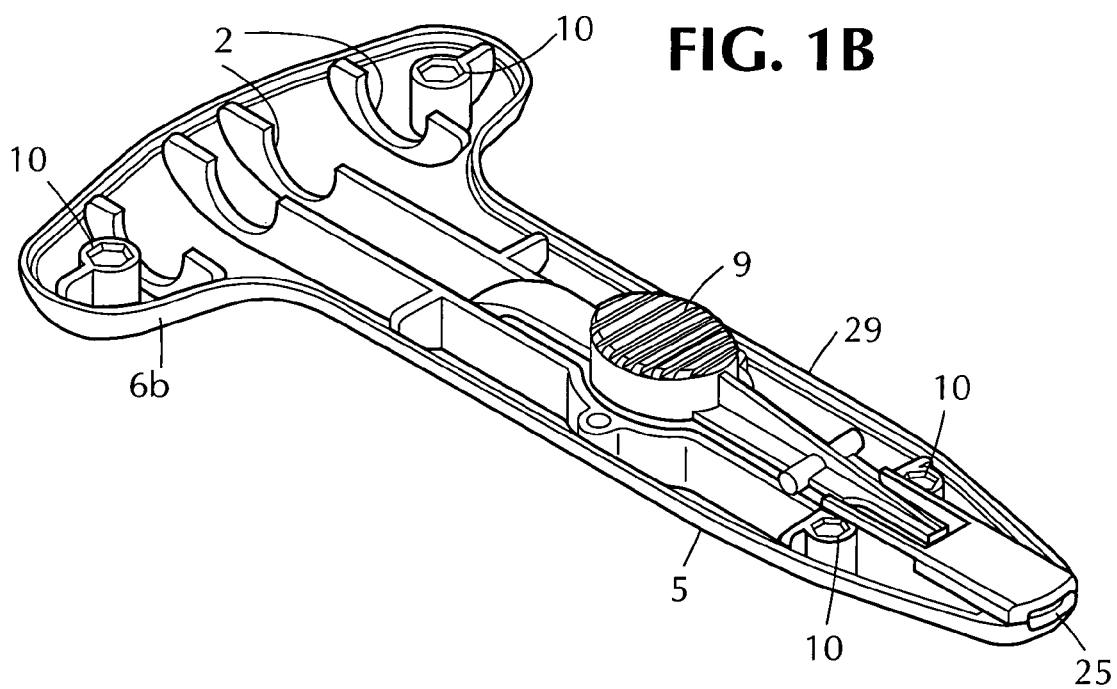

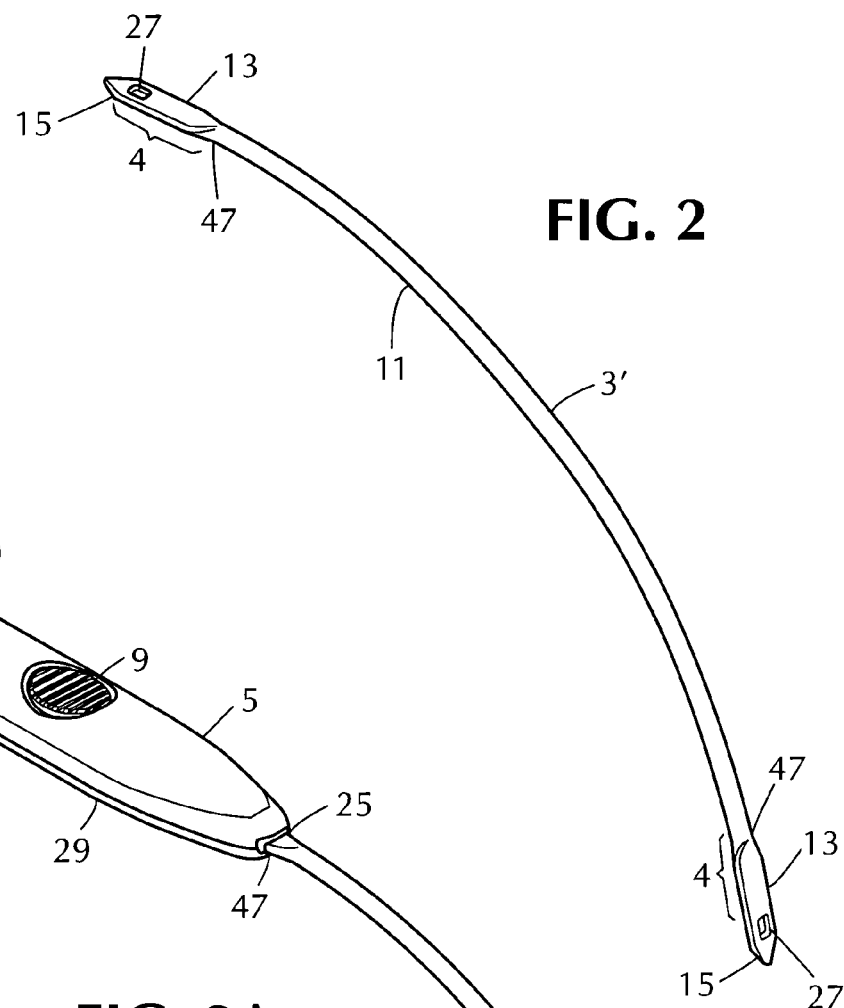
FIG. 2
FIG. 3A

FIG. 15A     FIG. 15B     FIG. 15C
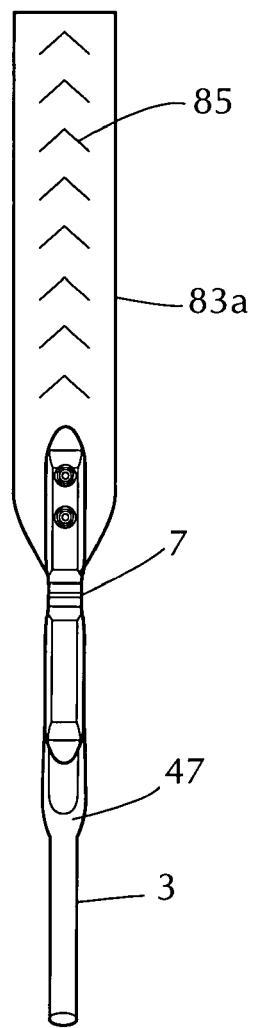
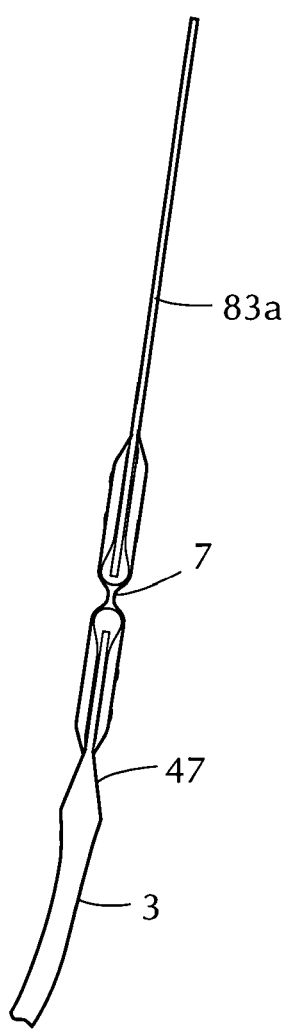
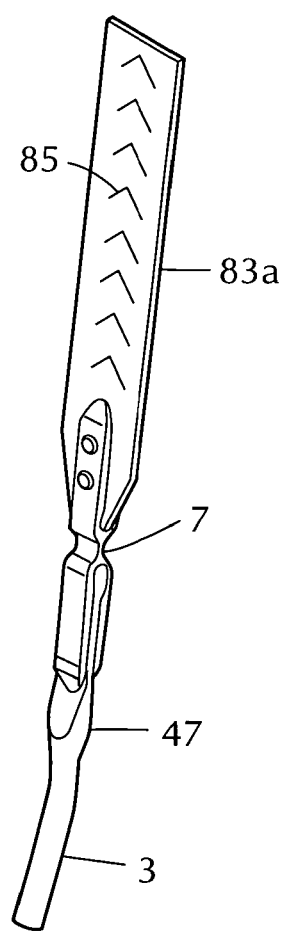

FIG. 18A
FIG. 18A
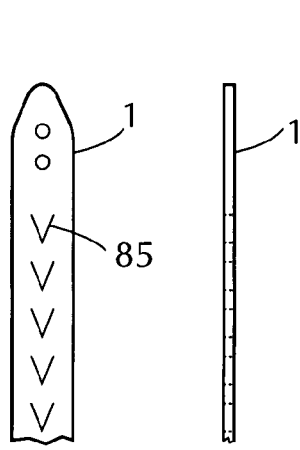
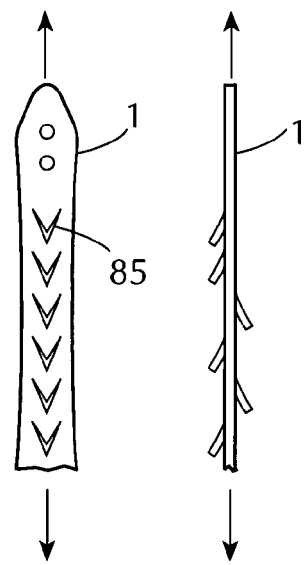
FIG. 19A
FIG. 19B
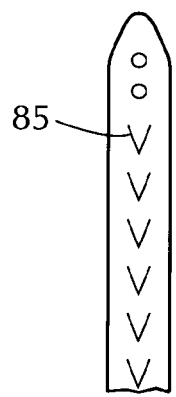
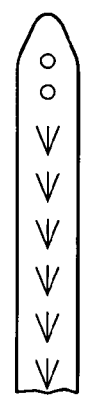
FIG. 19C
FIG. 19D
FIG. 19E
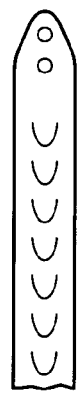
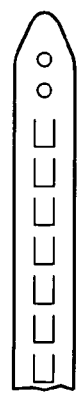
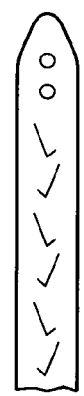

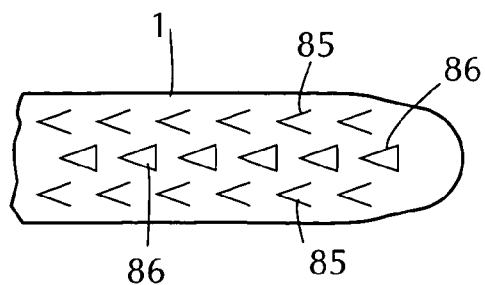
FIG. 26C
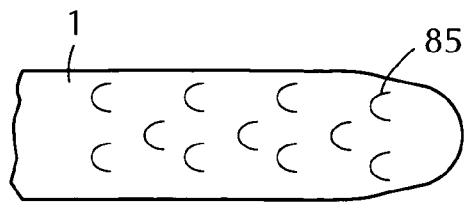
FIG. 26D
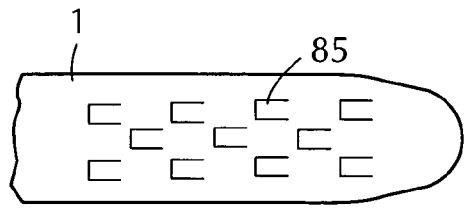
FIG. 26E
FIG. 27
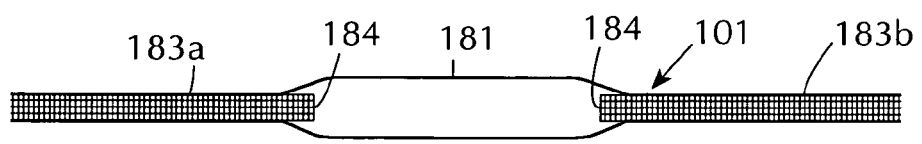
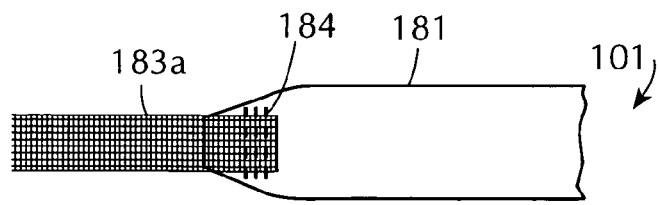
FIG. 28A
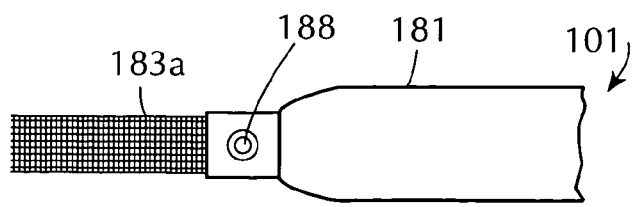
FIG. 28B FIG. 35  FIG. 36  FIG. 37
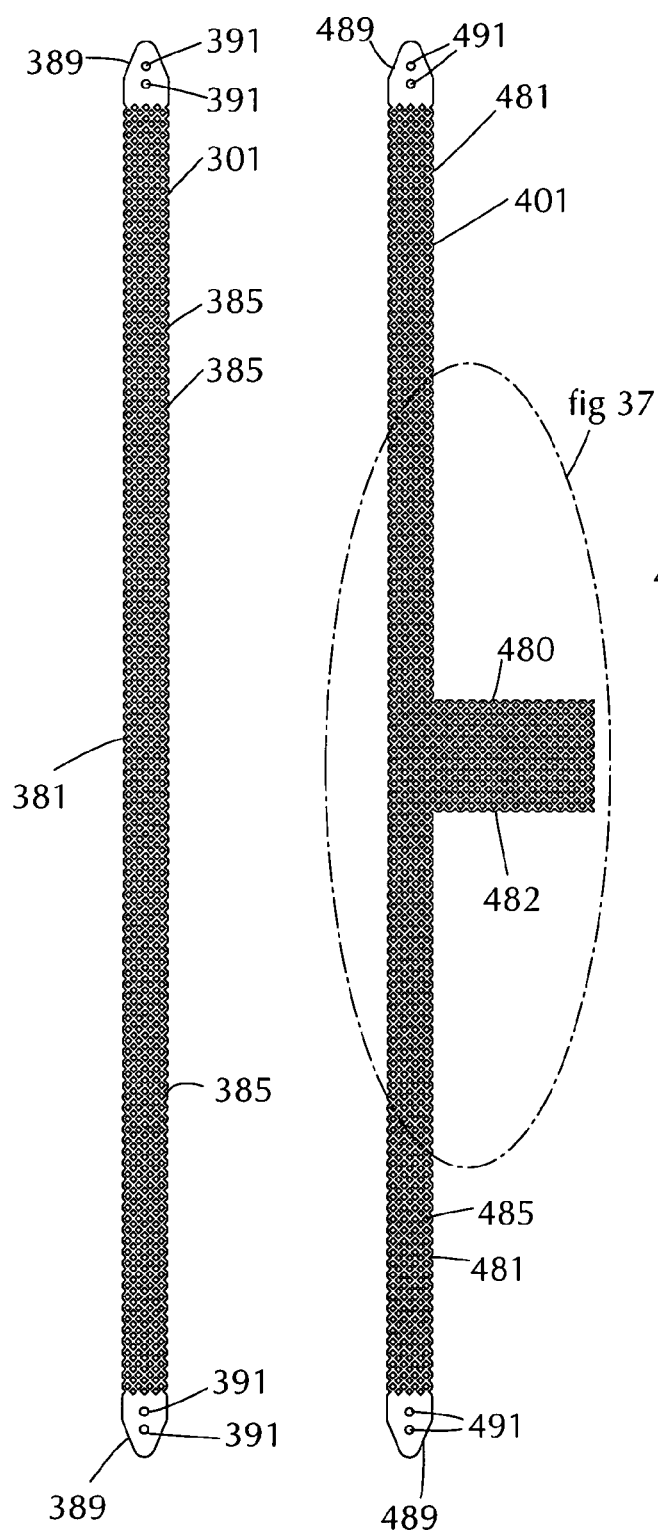
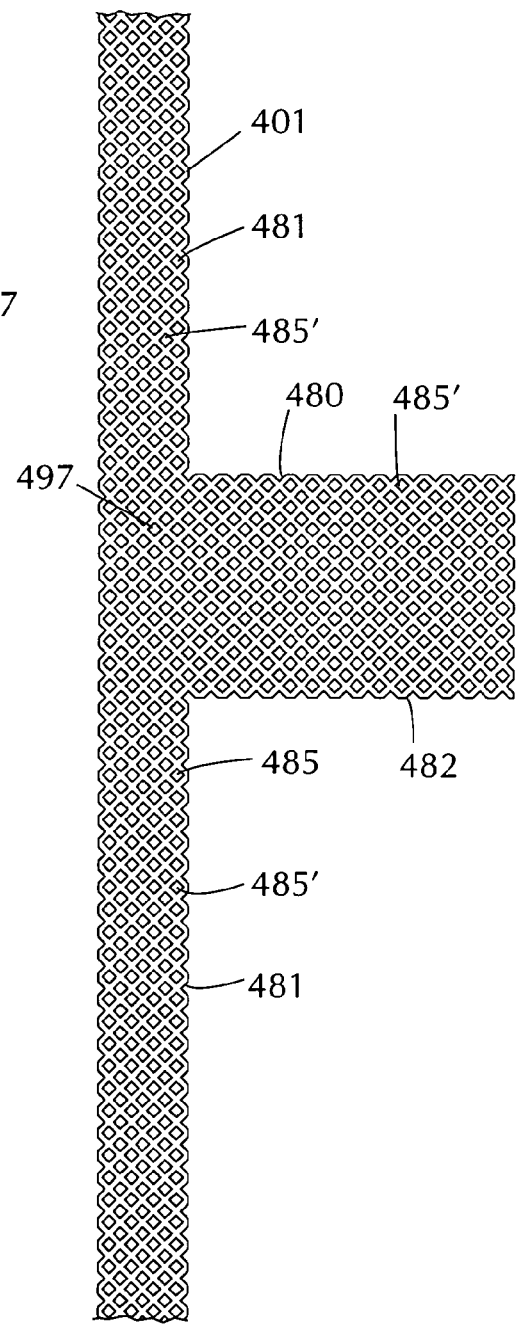

FIG. 42
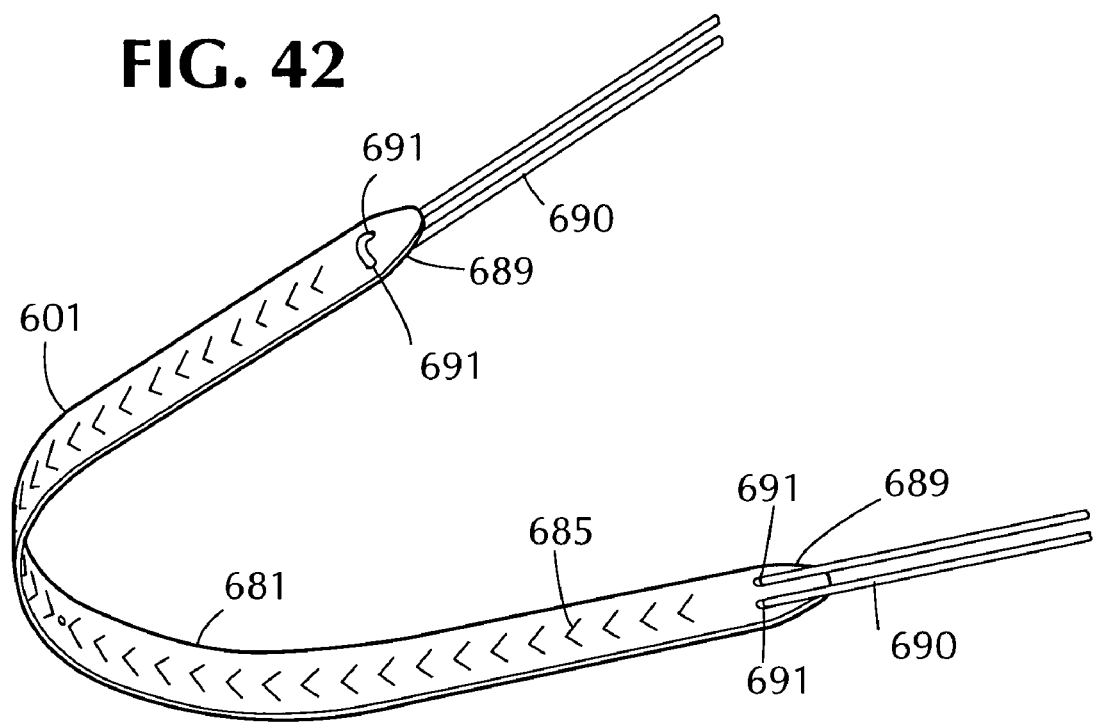
FIG. 43A     FIG. 43B     FIG. 43C
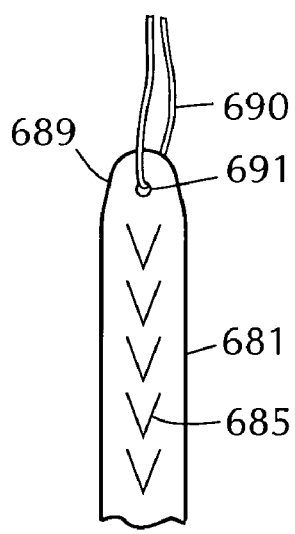 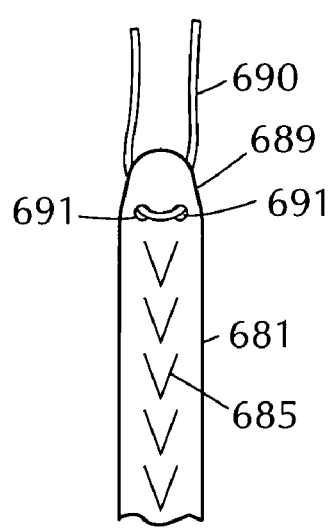 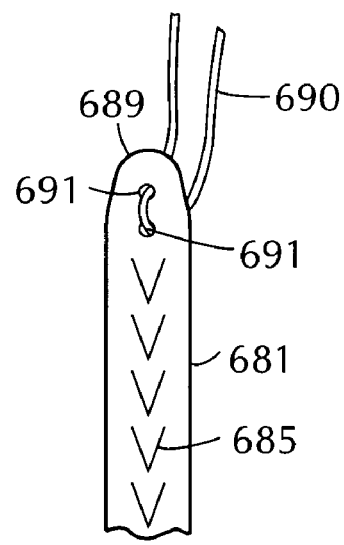

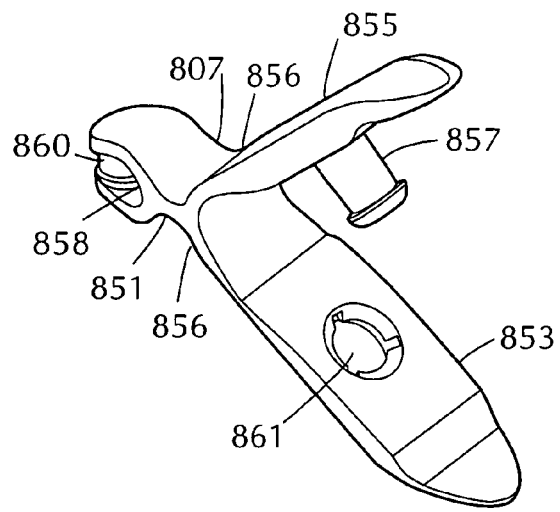
FIG. 50A
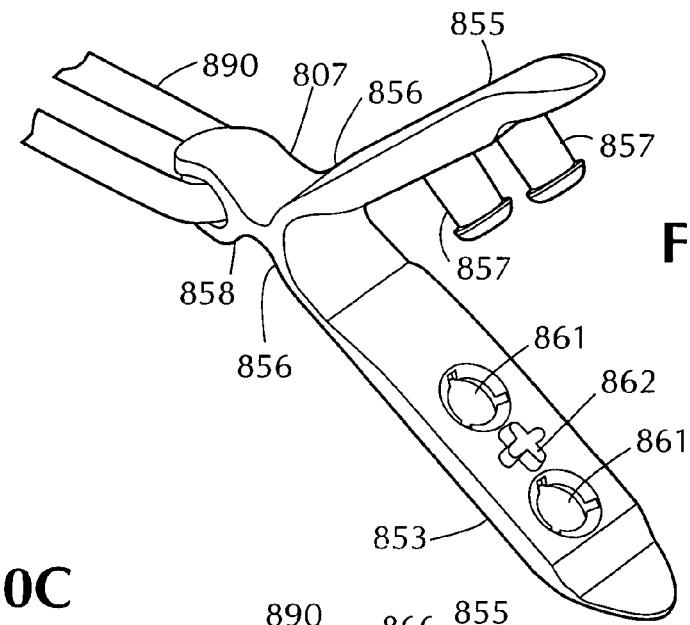
FIG. 50B
FIG. 50C
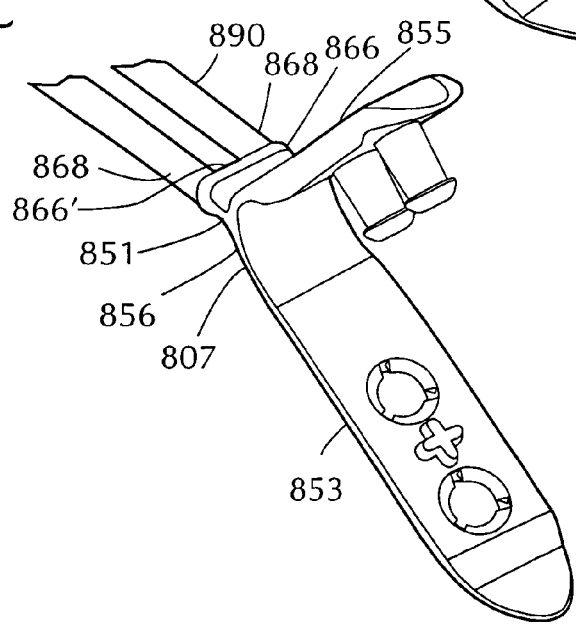

FIG. 52
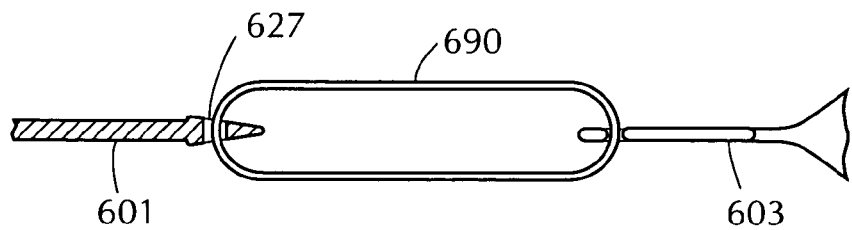
FIG. 53A FIG. 53B
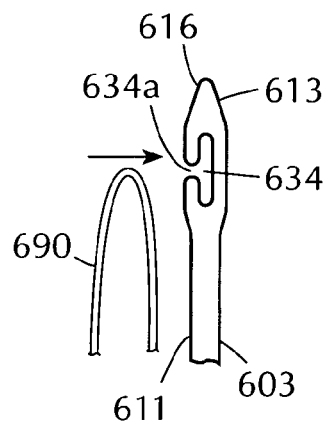 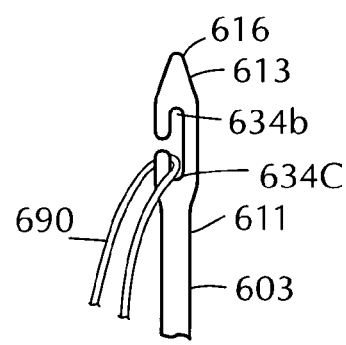
FIG. 54
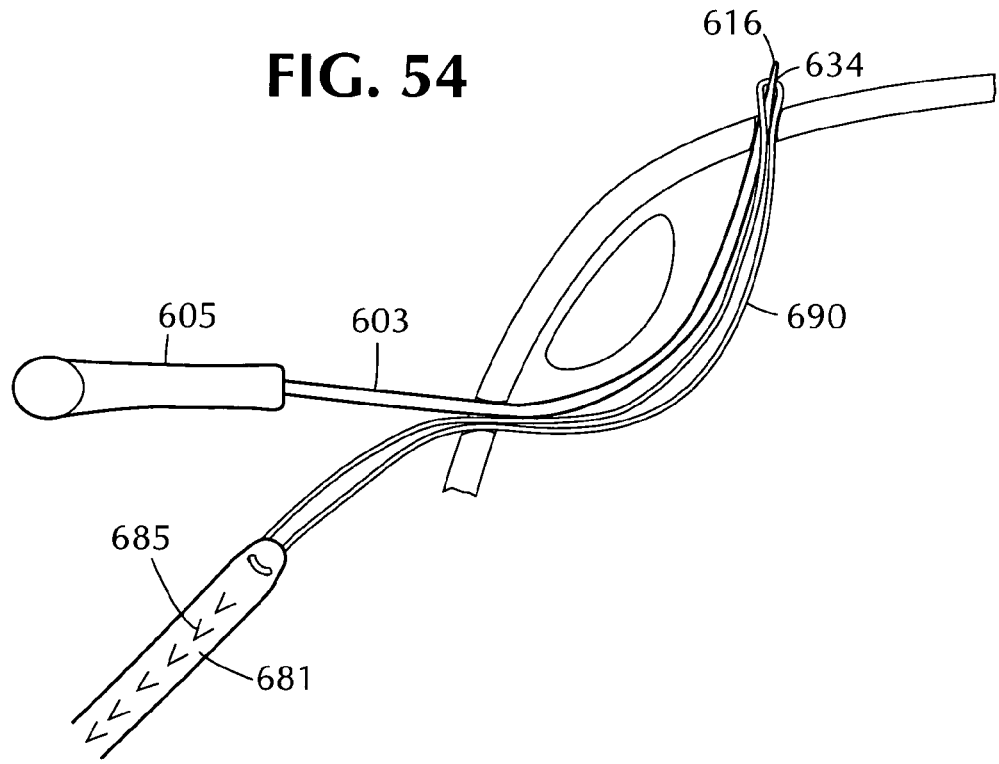

FIG. 57A     FIG. 57B     FIG. 57C
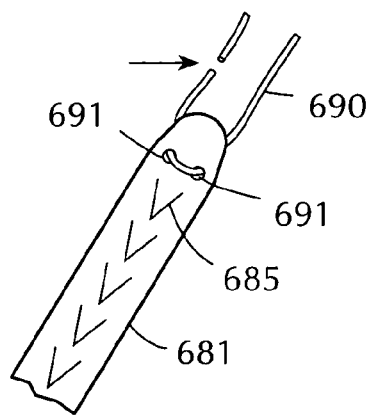 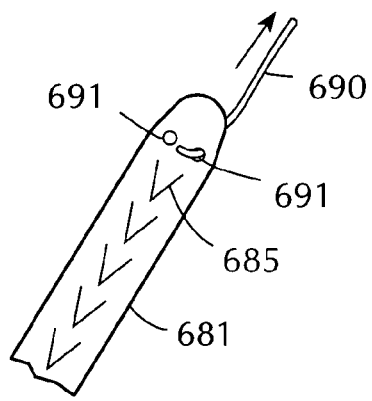 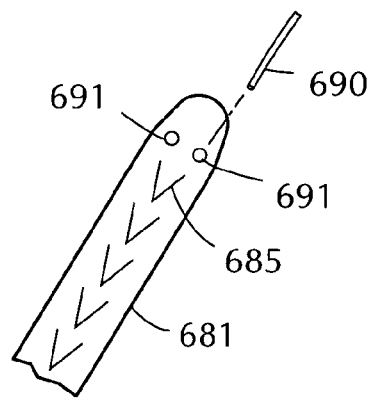
FIG. 58A     FIG. 58B
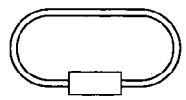 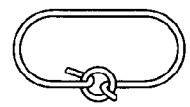
FIG. 58C     FIG. 58D
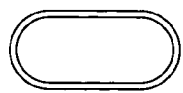 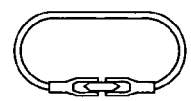
FIG. 58E     FIG. 58F     FIG. 58G
 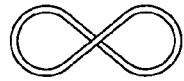 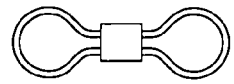

SELF-ANCHORING SLING AND INTRODUCER SYSTEM

CROSS-REFERENCE TO RELATED APPLICATIONS

This application claims the benefit of U.S. Provisional Patent Application No. 60/400,616, filed on Aug. 2, 2002, and 60/479,039, filed on Jun. 17, 2003.

BACKGROUND OF THE INVENTION

Various surgical techniques benefit from the use of nonnative flat supporting members inserted into the patient's body to apply pressure to the patient's own tissue. Such implanted supporting members can be made from synthetic material, natural material, whether harvested from the patient or elsewhere, or composites of both synthetic and natural materials. When using harvested natural material, it may be desirable to treat the source tissue to alter its physical properties to insure it is biocompatible and does not cause an adverse reaction with the patient's immune system.

One example of a sheet-like support structure for use in a range of surgical techniques is described in U.S. Pat. No. 6,197,036. This patent discloses a pelvic floor reconstruction surgical patch made from natural or synthetic biocompatible material. According to the '036 patent, the preferred material for use in the patch is synthetic fabric made from polyester, more preferably, collagen coated polyester. The patch has a number of holes which are arranged in a specific manner with respect to the patch's corners.

Another material that can be used as a patch to reinforce soft tissue is processed porcine intestinal tissue. Examples of support structures made from such material include the Surgisis® Gold™ Hernia Repair Grafts, the Surgisis® Soft Tissue Grafts, and the Surgisis® IHM™ Inguinal Hernia Matrix, all manufactured by Cook Surgical, of Bloomington, Ind. and described in Cook Surgical's literature.

An increasingly-widespread technique for treating female urinary incontinence is that of sling suspension. Examples of such procedures and equipment which can be employed are discussed in U.S. Pat. Nos. 5,112,344, 5,899,909, and 6,273,852 B1. In this technique, a flat supporting member is used to treat female urinary incontinence by permanently positioning a strip-like sling beneath the patient's urethra. By implanting the sling and then adjusting the sling to apply a desired level of force to the patient's urethra, the amount of pressure which the patient must thereafter exert to void her bladder is increased, improving continence. The sling member is preferably implanted in the patient's tissue by using a needle to draw the sling into its approximate position. Then, the surgeon can make fine adjustments to properly locate the sling member, and to apply the required amount of tension to the tissue requiring support.

Although originally implanted slings were anchored in the patient's body, for example, by using sutures to join the sling ends to the patient's pelvis, it is now more common to leave the sling ends unattached. The sling is maintained in position through friction between sling material and the patient's own tissue, in particular, in the case of a sling implanted in the lower abdomen, with the rectus fascia. This approach is known as a "self-anchoring" or "tension-free" procedure.

In self-anchoring sling support procedures it is important that the sling be held firmly in place by friction with the patient's tissue. Should the ends of the sling slip, then insufficient support will be provided for the urethra to alleviate incontinence, and the procedure will be unsuccessful. It is also important that the sling material used be strong enough to withstand, without rupture or tear, any forces that are encountered following implantation, for example, when the patient sneezes.

Slings can be made from tape or mesh. Numerous implant materials have been considered and used for sling procedures, including both synthetic mesh and natural tissue.

Although easy to sterilize, strong and inexpensive, synthetic mesh material has a number of shortcomings which will be discussed in further detail below. Just by way of example, when synthetic mesh material is used as a sling support, the roughness of the synthetic mesh may lead to abrasion of the patient's urethra, and that can cause infection and/or erosion of the patient's tissue.

When performing sling support procedures, it is important to use an implant which is well-tolerated by the patient's immune system. To this end, sling supports can be made from processed natural material. One example of such a processed tissue sling support is the Stratasis® TF support, manufactured by Cook Urological, Inc. of Spencer, Ind. The Stratasis® TF support is a three-dimensional extracellular matrix which includes collagen, non-collagenous proteins, and biomolecules that is made of natural biomaterial derived from the small intestine of pigs. The Stratasis® TF support is gradually replaced by the patient's body.

A traditional sling procedure involves placing a narrow strip of an implant material (natural tissue or synthetic mesh) under the urethra and securing it to the rectus fascia or other portions of the patient's anatomy with sutures to hold the implant in position during the healing process.

More recently, a newer technique has been used to place a strip of synthetic mesh under the urethra without securing the mesh in place with sutures. In this technique, the implant member is held in place during the healing process by the friction between the mesh and the surrounding tissue. This improvement, which employs specialized instrumentation, has helped reduce operative time and has made the procedure less invasive.

Although each of these techniques has demonstrated good results, each has a number of potential complications, due, in part, to the type of material from which the sling is formed.

Synthetic mesh is used with the self-anchoring techniques. Among the benefits to using synthetic mesh material is that the friction of the synthetic mesh with the surrounding tissue allows for suture-free placement of the mesh strip. "Kits" are commercially available which include a suitable mesh implant member and the small needles needed to pass the synthetic mesh implant member into the patient's body; few other surgical instruments are required. This has resulted in a simpler and less invasive procedure in which only small incisions are required, no patient tissue need be harvested, and just a short hospital stay is required.

Clinical articles have suggested that the synthetic mesh material used in this procedure is subject to a higher risk of causing erosion of the patient's tissue than are natural materials. Furthermore, the synthetic mesh material has a higher risk of infection than does natural material, probably because the mesh provokes a foreign body reaction from the patient's body or may harbor bacteria around the mesh. The synthetic mesh material also tends to have a greater amount of scar tissue formation around the mesh fibers, instead of vascular ingrowth.

Natural materials, for example, autologous, allograft, or xenograft tissues, or soft collagen fiber engineered materials, which are used in traditional techniques, offer such benefits as a lower risk of erosion than the synthetic materials. Natural materials also have a lower risk of infection, presumably because there is no foreign body reaction. The natural materials also experience better tissue ingrowth than the synthetic materials because they are made up of collagen fibers, which can serve as a tissue-building framework.

Disadvantageously, the natural materials require sutures be used to anchor the material in position. To implant the natural material slings, traditional instrumentation is used. Such instrumentation often requires more invasive surgical techniques, larger incisions, harvesting of the patient's own tissue for use as the sling, and consequently, may result in a longer hospital stay.

Although natural support members offer many benefits when used in the manner described above (for example, they are not abrasive), they also are generally more expensive than their synthetic counterparts, since such support members are derived from natural source materials that must be treated to insure sterility, stability and biocompatibility.

Given the expense of natural support members, it is desirable to reduce the amount of natural material used in each support member without also reducing the self-anchoring properties, positioning ability, strength or durability of that support member.

There also exists a long-felt and unsolved need for a support system, and, in particular, a sling suspension system which offers the respective cost and tolerance benefits of both synthetic and natural materials, without the weaknesses of either of those techniques.

Although some doctors are satisfied with the results that they have achieved using synthetic mesh sling kits, other doctors prefer not to use the synthetic materials due to the materials' higher potential for complications such as the occurrence of infection or foreign body reaction around the mesh, or urethral or vaginal wall erosion due to the mesh. In some cases of erosion, mesh has been observed to unravel, creating a sharp "fishing line" effect, which can slice through the patient's tissue. This is not a concern with natural fibrous materials such as autologous, allograft, or xenograft tissues, which elongate less and do not neck down under load.

Existing surgical hardware, such as the McGuire™ suture guide, which has a central suturing hole, and available from C.R. Bard, Inc. of Murray Hill, N.J., is based upon what is known as the "Stamey" needle. Although such devices could be modified for use in the field of this invention, they do not possess all the requisite properties for the uses envisioned for this invention.

Thus, there exists a long-felt and unsolved need for a sling suspension system which offers the distinct benefits of both synthetic and natural materials, without the weaknesses of either of those techniques.

SUMMARY OF THE INVENTION

First, it should be understood that although this disclosure speaks of the sling suspension of the female urethra, this invention is not to be limited thereto. By way of non-limiting example, the devices and techniques taught herein could be employed to support other body organs such as the bowel or bladder. Consequently, all portions of this description should be understood to encompass such alternative uses of this invention, as well as all modifications in size and proportion of the disclosed invention's parts which may be required to implement those alternative uses.

Taken together, the components used in this invention and described hereafter provide a minimally invasive, simple technique that is easily learned and which requires little operative time. The implant member will offer the low complication rate and good tissue ingrowth of a natural material, while the texturing provides the self-anchoring properties of a synthetic mesh, thereby eliminating the need for sutures or other anchoring means.

Among the benefits of this invention is improved flexibility; the surgeon can use this system for either an upward or a downward approach without any need to employ special equipment.

The present invention is intended to provide a self-anchoring sling kit, using natural material, hybrid material, or even synthetic material, which is an improvement upon known systems. This system takes advantage of the best features of both synthetic mesh and natural tissue implants, using those materials separately or together, and provides an excellent combination of versatility, ease of use, and safety.

The invention also concerns a new device and technique to treat stress urinary incontinence in women. The technique is a modification of a traditional pubourethral sling procedure, which is done to provide an underlying support to the urethra.

More specifically, the present invention is directed to a system for supporting the urethra which includes an introducer needle at least one or both of the ends of which are flattened and which have openings therethrough, a handle having a latch mechanism which engages the opening in the flattened portion of the first end of the introducer needle, an implant member, and a connector joining the end of the implant member to the flattened portion of one of the ends of the introducer needle.

One aspect of this invention involves a system for supporting a female urethra having an introducer needle with first and second ends, each end having a flattened portion with an opening therethrough, a handle having a latch mechanism which engages the opening in the flattened portion of the first end of the introducer needle, an implant member having an end and a connector joining the end of the implant member to the flattened portion of the second end of the introducer needle. The introducer needle can be curved and symmetrical, and the flattened portion of the first end may differ in size from the flattened end of the second portion. The introducer needle can have a flared section with a cross-sectional profile that is larger than a cross-sectional profile of the connector.

This invention also is drawn to a connector for attachment to the end of an implant member having an arm having a hole therethrough or an introducer needle including a flat spatulated section having an opening. The connector has a central portion, a first arm pivotally mounted to that central portion and having a first opening at a first end, a second arm pivotally mounted to the central portion and having a first projection extending therefrom, the first projection being positioned so that when the first arm and the second arm move together, the first projection is received in the first opening, and an implant attachment structure to which the implant member is connected. Teeth or a "+"-shaped boss may protrude from the arm surfaces to engage the implant member. Any other suitable boss shape, such as a hemisphere or cylinder, also could be used. A second set of arms also may be provided.

Still another aspect of this invention is a connector for attachment to an implant member or an introducer needle including a flat spatulated section having an opening. This includes an elongated base portion having a first engaging structure at a first end and a second engaging structure at a second end, a first arm pivotally mounted to the elongated base portion and having a third engaging structure, the third engaging structure being positioned so that when the first arm pivots toward the elongated base portion, the first and the second engaging structures meet and engage, and a second arm pivotally mounted to the elongated base portion and having a fourth engaging structure, the fourth engaging structure being positioned so that when the second arm pivots toward the elongated base portion, the second and fourth engaging structures meet and engage. The engaging structures can be mating openings and projections.

Additionally, this invention relates to a connector for attachment to an implant member or an introducer needle with a flat spatulated section having an opening. The connector has an elongated base portion with a first engaging structure, an arm pivotally mounted to the elongated base portion and having a having a second engaging structure, the engaging structures meeting when the arm pivots toward the elongated base portion, and an attachment point for connection to an implant member. The engaging structures may have openings and projections that can meet. The attachment point can be joined to the implant member by a staple, a rivet, an adhesive or a suture, for example.

A further aspect of this invention is an introducer needle for use in a surgical procedure having a central portion, first and second flat spatulated sections that may be integral with the central portion, at least one flat spatulated section having a tip and a constant width portion disposed between the tip and the central portion, and an opening formed in the flat spatulated section, and a flared section connects the first flat spatulated section to the central portion. The flared section has a cross-sectional profile that covers a cross-sectional profile of the first flat spatulated section. The introducer needle may be asymmetric. The spatulated sections may have different shapes.

Another introducer needle has a first flat spatulated section, a first straight portion connected to a distal end of the first flat spatulated section, a curved portion connected to a distal end of the first straight portion, a second straight portion connected to a distal end of the curved portion, a second flat spatulated section connected to a distal end of the second straight section, and a flared section connecting the first flat spatulated section to the first straight central portion, the flared section having a cross-sectional profile that covers a cross-sectional profile of the first flat spatulated section. At least one flat spatulated section has a tip and a constant width portion disposed between the tip and the central portion, and an opening formed in that the flat spatulated section. The spatulated sections, flared section, straight portions and curved portions can be integrally formed. The straight portions may differ in length.

Also, an introducer needle can have a body portion with a proximal straight portion integral with a distal curved portion, a handle receiving the proximal end of the straight portion and a flat spatulated section having a "T"-shaped opening located at the distal end of the curved portion. The handle may be permanently attached to the straight portion.

An introducer needle for use in a surgical procedure employing a filament has a tubular body, a rod disposed in the tube's lumen, and a needle tip movably disposed in the lumen at the distal end of the tubular body and attached to the rod, the needle tip having an opening therein for receiving the filament. When the rod is moved toward the distal end of the tubular body the needle tip moves forward.

Another introducer needle has a body portion with a curved portion, a flared section located at the distal end of the curved portion, and a flat spatulated section having a "T"-shaped opening located at the distal end of the flared section, a leg of the "T" extending to an edge of the flat spatulated section.

An introducer needle for use in a surgical procedure includes a body portion with a curved portion, a flared section located at the distal end of the curved portion, and a flat spatulated section having an internal opening located at the distal end of the flared section. The internal opening may be "H"-shaped or substantially rectangular, and in the latter case, can have a central portion larger in size than a front end and a back end of the internal opening.

Also, a handle for an introducer needle having a flat spatulated section having an opening includes a housing with an elongated portion having a distal end with an opening therethrough, the opening being dimensioned to receive the flat spatulated section and hold the flat spatulated position in a connecting position in the housing, and an elastically-biased latch portion having a projection dimensioned and disposed so that when the flat spatulated section is received by the opening and is held in the connecting position, the projection passes cooperates with the opening to secure the handle to the introducer needle. The housing may be made from two shells, and also can include an insert with a slot dimensioned to receive the flat spatulated section, the insert being disposed between the shells. A weight may be disposed within the housing.

According to this invention, an implant member includes a central portion with first and second sides, first and second arm sections integral with the first and second sides of the central portion, respectively, at least one of the first and second arm sections having an irregular border. At least one of the central portion and the first and second arms can have an edge with slits or openings therein.

A different implant member includes an elongated body of flexible material with first and second ends and a central portion that includes an axis running along a length of the implant member. The central portion has slits arranged along the axis, the slits moving out of the implant member's plane when tension is applied to the implant member.

Still another implant member has a central portion with first and second ends, and first and second arms joined to the first and second ends, respectively. The central portion can be made of a material that is differed from the first and second arms, possibly natural and synthetic materials, respectively.

Still another implant member includes an elongated body with slits that open when tensile force is applied to the body.

Also, the implant member can include a body with first, second and third sections, the second section being located between the first and the third sections, the first and the third sections each having slits therein that open when tensile force is applied to the body. These slits can be arranged in rows, and the rows can be parallel. Slits in adjoining rows can be staggered in position.

A different implant member has first and second extension loops and a support section with first and second ends having holes, the first extension loop passing through one hole and the second extension loop passing through another hole. Connectors with structure for attachment to a needle tip can be joined to the extension loops.

An implant can be made by providing a body and forming slits in the body that are arranged to open when tensile force is applied to the body. These slits can be arranged in rows, which may be parallel. A skin graft mesher can be used to create the slits in the body.

Methods of providing support for a female urethra are taught that involve creating at least one incision in the patient's abdominal wall at the level of the pubic symphysis, creating an incision in the anterior vaginal wall just below the urethral meatus, advancing an introducer needle, having a detachable handle joined thereto, into the retropubic space via the incision in the patient's abdomen and downward until the needle is exposed at the vaginal incision, connecting one end of an implant member to the end of the introducer needle protruding from the vaginal incision using a permanent snap-on tissue connector, withdrawing the introducer needle through the abdominal incision with the implant member attached, and positioning the implant member loosely under the urethra by at least one of gently pulling on the abdominal end of the implant member and by loosening the implant member by pulling on the implant member with a clamp at the vaginal incision.

Also, a method of providing support for a female urethra can involves creating at least one incision in the patient's abdominal wall at the level of the pubic symphysis, creating a second incision in the anterior vaginal wall below the urethral meatus, advancing an introducer needle, having a detachable handle joined thereto, through the vaginal incision upward until the introducer needle tip is exposed through the first abdominal incision, connecting one end of an implant member to the end of the introducer needle protruding from the vagina using a permanent snap-on tissue connector, drawing a portion of the implant inward through the vaginal incision and through the first abdominal incision, and positioning the implant member loosely under the urethra by at least one of gently pulling on the abdominal end of the implant member and by loosening the implant member by pulling on the implant member with a clamp at the vaginal incision.

Among the benefits of this invention is improved flexibility; the surgeon can use this system for either an upward or downward approach without the need to employ special equipment.

BRIEF DESCRIPTION OF THE DRAWINGS

In the accompanying drawing figures, which are merely illustrative, and wherein like reference characters denote similar elements throughout the several views:

FIG. 1A is a perspective view of an introducer handle with pushbutton according to the present invention, seen from the front, right side and top, and FIG. 1B is a perspective view of the bottom shell portion of the handle shown in FIG. 1A;

FIG. 2 is a perspective view of a dual-ended introducer needle according to the present invention, seen from the front, right side and top;

FIG. 3A is a perspective view showing the handle connected to an introducer, as seen from the front, right side and top.

FIGS. 15A-C are front, side and perspective views showing the connector of FIGS. 9A-D affixed to an implant member and a introducer needle;

FIG. 18A depicts an implant member in accordance with the present invention in a tension-free state, and FIG. 18B shows that implant member when tension is applied thereto;

FIGS. 19A-E are views showing the configuration of different internal slits in various implant members according to this invention;

FIGS. 26A-E are top plan views showing a number of different implant member configurations having internal slits to improve anchoring properties over a flat member;

FIG. 27 is a top plan view of a composite implant member;

FIGS. 28A-28G are views showing various ways to assemble a composite implant member in accordance with this invention;

FIG. 35 is a top plan view showing an embodiment of this invention in which all but the ends of the implant have slits;

FIG. 36 is a top plan view of still another embodiment of this invention having an enlarged central section to better support body tissue;

FIG. 37 is a close-up of a portion of FIG. 36;

FIG. 42 is a perspective view showing another form of implant member;

FIGS. 43A-C are front perspective views showing several alternate configurations of the implant member of FIG. 42;

FIG. 50A is a perspective view of a connector suitable for use with the implant member shown in FIG. 45; FIG. 50B is a perspective view of an alternate version of the connector of FIG. 50A, and FIG. 50C depicts another version of a connector joined to the implant member of FIG. 45;

FIG. 52 is a side cross-sectional view showing another embodiment of this invention;

FIGS. 53A and 53B are side views showing how an implant member such as that shown in FIG. 45 is attached to an introducer needle;

FIG. 54 is a side cross-sectional view showing the embodiment of FIG. 45 during implantation in a patient's body;

FIGS. 57A-C are perspective views showing different steps in the use of an implant member in accordance with this invention;

FIGS. 58A-G are side elevational views showing different ways of forming loops for use with an implant member in accordance with this invention;

DETAILED DESCRIPTION OF THE PREFERRED EMBODIMENTS

Figure 3B:
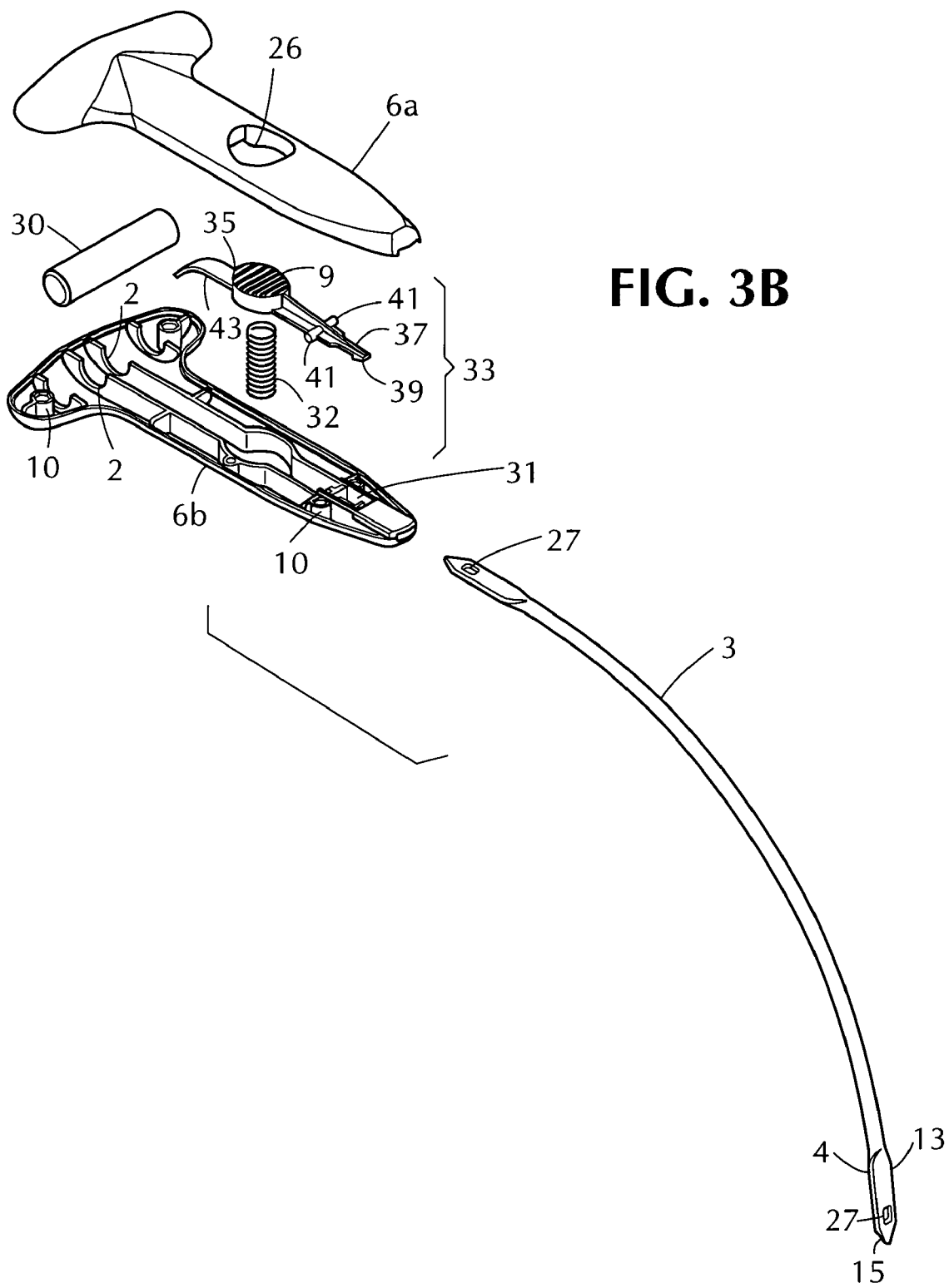
FIG. 3B is a perspective exploded view of the assembled components shown in FIG. 3A.

Referring now to the drawings, the various embodiments of the present invention will be discussed in detail.

In the following discussion, like numbers will be used to describe like portions of the different embodiments.

Figures 12, 13:
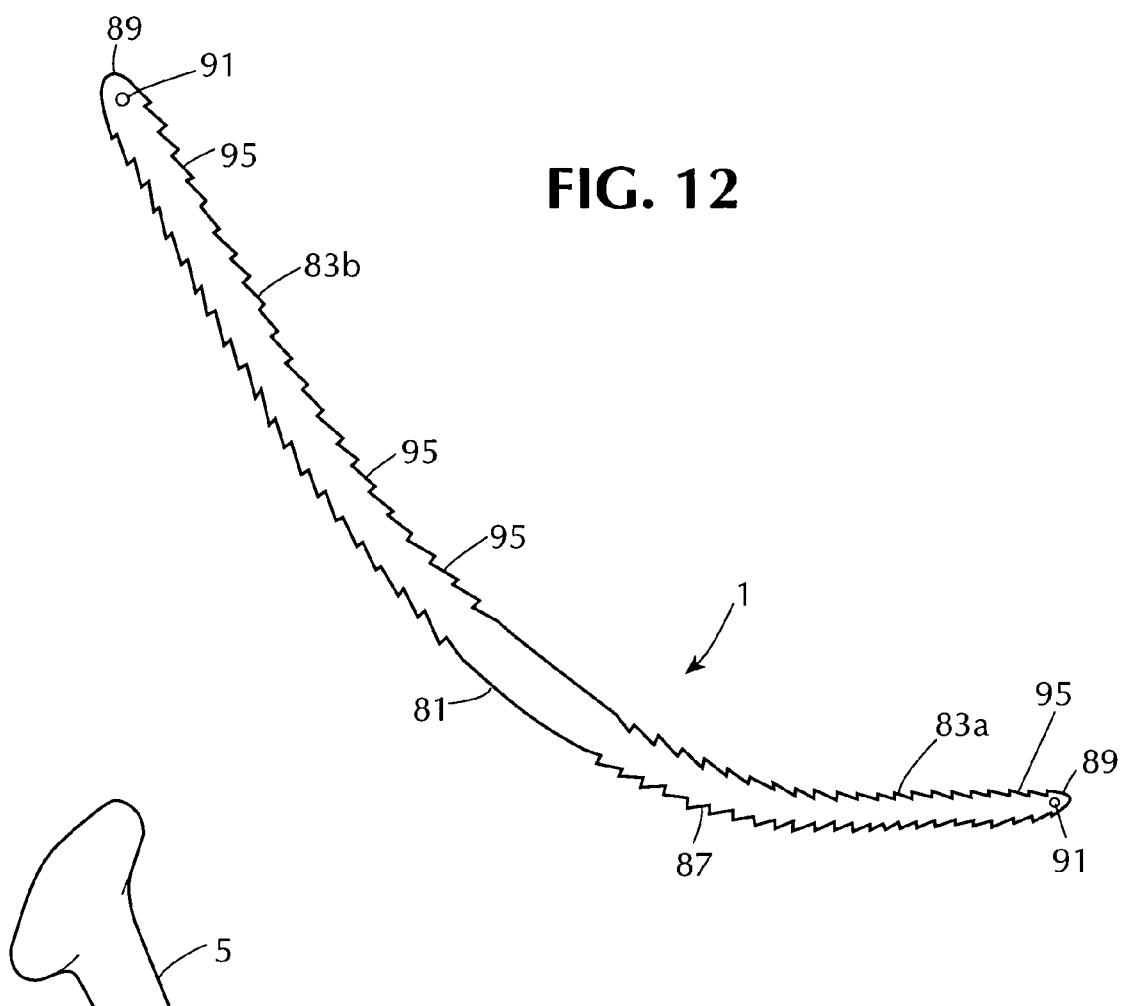
FIG. 12 is a perspective view of a textured natural tissue implant.
FIG. 13 is a perspective view showing the assembled introducer needle, connector and tissue implant.

With general reference to FIG. 13 for the purpose of introducing various components of the present invention, this invention involves an implant member 1, which can be made of natural material, synthetic material, or a combination thereof, and which can be textured or slit, and also an introducer system having a handle 5, a connector 7, and an introducer needle 3. The purpose of this invention is to place a piece of material beneath the patient's urethra so that the urethra is supported, helping to prevent the involuntary release of urine from the bladder. Using this invention implants also could be placed in other parts of a patient's body to support other body organs.

Together, these components facilitate a minimally invasive and simple technique that is easily learned and which requires little operative time. The implant member 1 is designed to have both a low complication rate and good tissue ingrowth of a natural material, while the texturing of the implant member 1 provides the self-anchoring properties of a synthetic mesh, eliminating the need for sutures or other anchoring means.

As will later be discussed in detail, the handle 5 allows the surgeon to guide accurately the introducer needle 3 into the patient's body, and increases device safety greatly when compared to a conventional implantation system wherein the surgeon directly grasps a needle without a handle (not shown). One end 4 of the introducer needle 3 is received in and is securely held by the handle 5. The other, free, end 4 of the introducer needle 3 is joined to the implant member 1 by a connector 7. Using the handle 5 the surgeon can draw the implant member 1 into place beneath the patient's urethra. The implant member 1 is then detached from the introducer needle 3 and is positioned as the surgeon wishes.

As will now be discussed in detail, this invention involves several different handle configurations, each of which can receive introducer needles that are suitable for performing a sling suspension procedure. Several different needle configurations are also proposed. In addition, a variety of different connectors for joining implant members to the needles are taught, and a number of implant members are disclosed. Some implant members can be joined directly to the needle.

As depicted in FIGS. 3A and 3B, the introducer system of the present invention includes a curved, double-ended introducer needle body 3 having blunt-tipped stainless steel introducer tips 4 at each end, and a modular handle 5 that can be attached to one of the ends 4 of the introducer needle 3. This introducer system is used with a tissue connector 7, as shown in FIG. 13. The tissue connector 7 allows the implant member 1 to be quickly and securely joined to the introducer needle 3. The handle 5 provides a solid, ergonomic interface, enabling the user to advance the introducer needle 3 into the patient's body with a high degree of control.

The handle 5 can be securely locked onto the introducer needle 3, yet still can be easily detached by depressing a pushbutton 9. As explained below, the pushbutton 9 releases the internal handle structure which holds the introducer needle 3 in place on the handle 5.

As will also be discussed later, at least one and possibly both ends 4 of the introducer needle has a flat, spatulated section 13 with a rounded tip 15 that serves as a dissecting tip enabling the clean and atraumatic dissection of the patient's tissue during insertion. The flat, spatulated section 13 also helps the introducer needle 3 remain close to the surface of the pubic bone during the insertion procedure. The rounded tip 15 serves to minimize unintended perforations of the bladder and other organs or vessels. The introducer needle 3 is dimensioned and curved to reflect the curvature of the posterior surface of the pubic bone, allowing the introducer needle 3 to stay in the "zone of safety" during placement. Symmetric or asymmetric introducers needles 3 can be used.

The present invention contemplates a handle 5 that can be removably joined to the introducer needle 3, as depicted in FIGS. 1A, 1B, 3A, 3B, 4A, 4B, and 5A-5C. Each of these drawings show somewhat different embodiments of the handle 5, but all are intended to improve safety by allowing the surgeon to securely hold and manipulate the introducer needle 3 received therein.

With reference now to FIGS. 1A and 1B, a first embodiment of handle 5 is preferably assembled from upper and lower shell portions 6a, 6b which, when joined together, have the desired handle shape, and which are designed to accommodate various handle components, discussed below. The handle 5 allows a solid, ergonomic interface for the user to advance the introducer needle 3 into the patient.

With continued reference to FIGS. 1A and 1B, handle 5 is preferably generally "T" shaped, with the long leg 29 of the "T" being internally shaped to receive one of the two spatulated sections 13 of the introducer needle 3 (the handle 5 also can be designed so that only one end of an asymmetric introducer needle can be received therein). The long leg 29 of the "T" shape can facilitate orientation and use of the present invention, and can be used for guidance, as well as to indicate the position of the introducer needle 3. A further benefit of this arrangement is that the long leg and horizontal bar of the "T" facilitate orientation of the needle held by the handle.

Figure 5A:
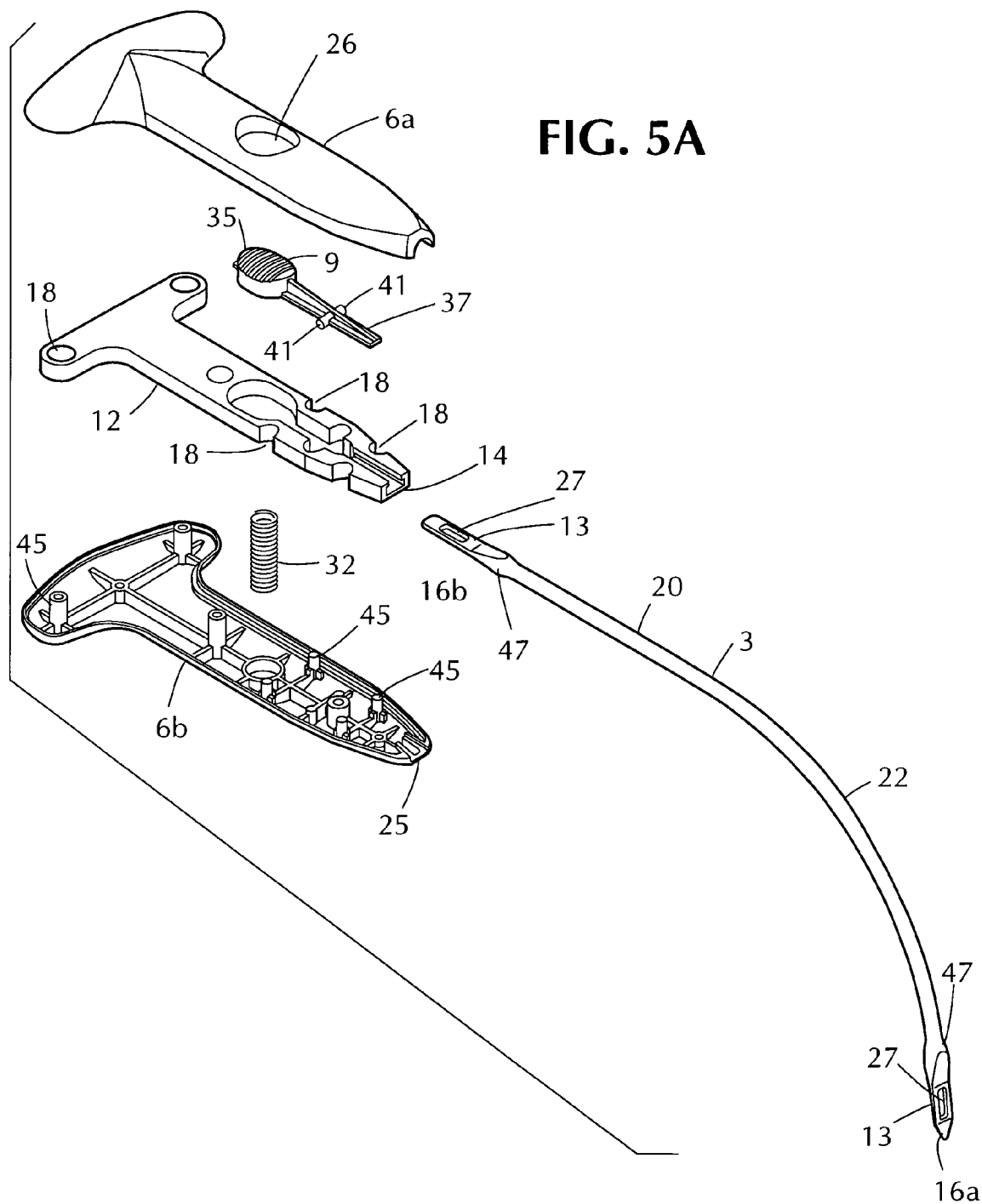
FIG. 5A is an exploded view showing another embodiment of a handle and needle in accordance with this invention.
Figure 5B:
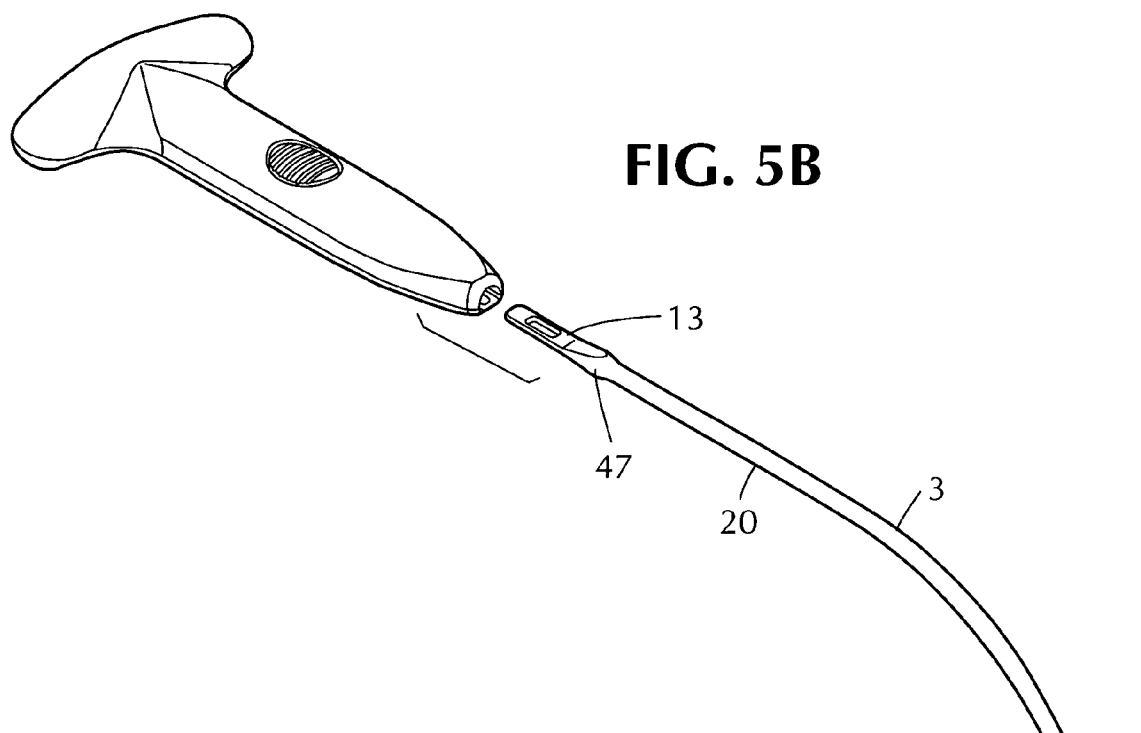
FIG. 5B shows the assembled handle as the needle is being inserted thereinto.
Figure 5C:
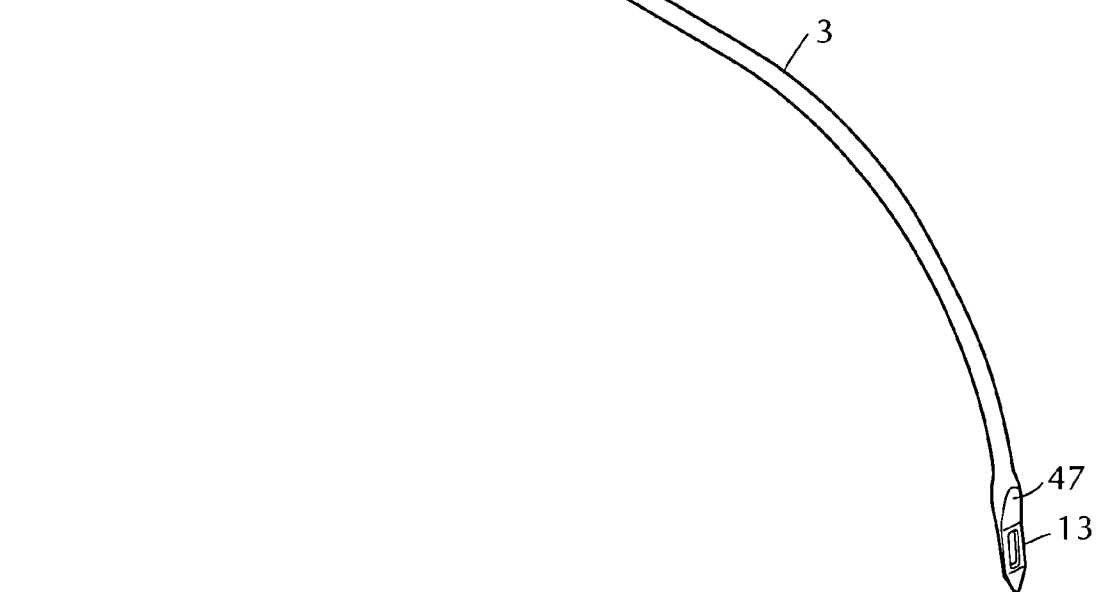
FIG. 5C depicts the needle as received in the handle.

Turning now to FIGS. 5A-C, an asymmetric introducer needle 3 is shown. The asymmetric geometry of this introducer needle 3 provides the benefits of having a tight bend radius as the distal end for close passage around the pubic bone, and a straight portion at the proximal end increases the working length of the needle. This working length is important because it allows the introducer needle 3 to fully extend between the suprapubic and retropubic incisions during use.

In contrast, if a dual-ended symmetric needle 3' such as that shown in FIG. 2 is used, it may be necessary to make compromises in needle design in order to obtain both a tight symmetrical curvature and, at the same time, an adequate working length.

In a further aspect of this invention, and with reference now to FIGS. 5A-C and 6A-B, the flat portions 13 of the introducer needle 3 are made with different sizes and shapes in order to help insure that the introducer needle 3 is properly oriented during use.

Figure 6A:
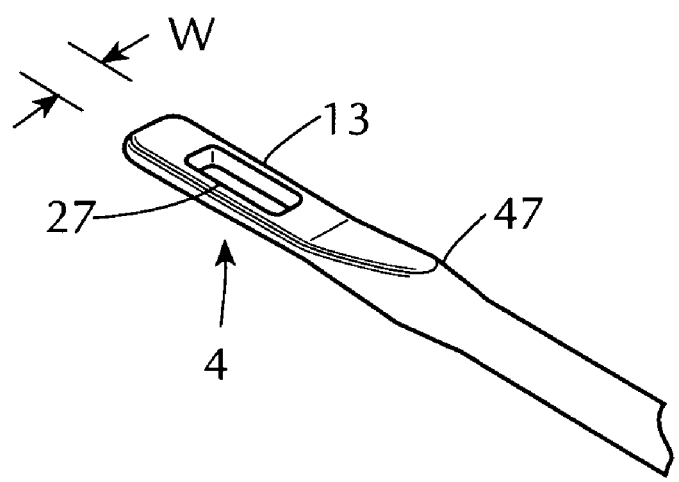
FIGS. 6A and 6B are close-up perspective views showing, respectively, the blunt and pointed tips of the needle depicted in FIG. 5A.

As seen in FIG. 6A, the flat portion 13 of the needle tip which adjoins the flared portion 47 of the needle and fits into the handle 5 where it is secured by the latch mechanism 33 preferably is made generally rectangular in shape. This flat portion 13 has a width W.

Figure 6B:
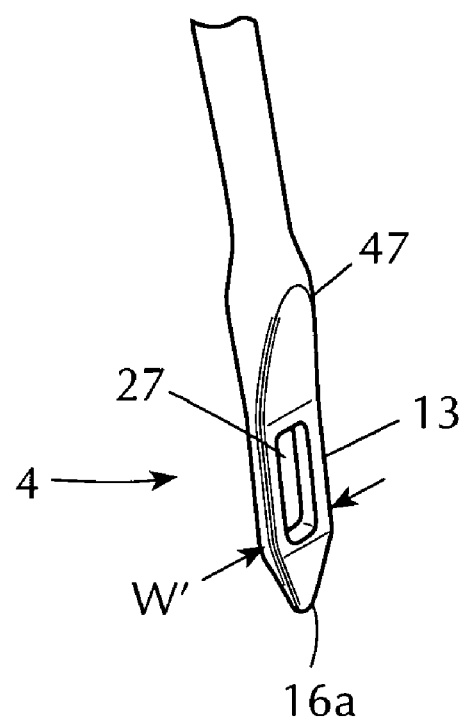

In contrast, as shown in FIG. 6B, the flat portion 13 of the needle tip 4 which passes through the patient's tissue has a pointed dissecting tip 16a having a gradual taper that facilitates advancement of the flat portion 13 through such tissue. This needle tip 4 also can be somewhat wider in width W' than the needle tip 4 which is received in the handle 5, since, as noted above, this prevents the needle 3 from being installed backward in the handle 5.

In addition, each of the flat portions 13 shown in FIGS. 6A and 6B has a central slot or opening 27, which, as already explained, insures that when the introducer needle 3 is joined to a connector 7 those parts are attached with the proper orientation.

As can be seen in FIGS. 1A-B and 4A-B, the end of the long leg 29 of the "T" formed by the joined upper and lower shells 6a, 6b has a small hole or slot 25 therein and an internal cavity 31 sized to securely receive most of the spatulated end 13 of a symmetric introducer needle 3' or, if an asymmetric needle 3 is used, the blunt end 16b of the introducer needle 3 intended to be secured in the handle 5. The handle 5 can be securely locked onto an introducer needle 3, yet also can be easily detached by depressing a pushbutton 9, as will be discussed below.

The edges of the two shell portions 6a, 6b are preferably arranged to form a lap joint (not shown) when assembled. Optionally, the shell portions 6a, 6b can be arranged with one shell 6a having projecting pins (not shown) and the other shell 6b having matching receptacles 10, preferably located at stress points. It is thought to be preferable to employ round pins and hexagonal holes 10; this way, air or adhesive pockets are avoided when the upper and lower shells 6a, 6b are joined, the air or glue escaping through the gaps formed between the different shaped parts, but any other hole and pin configuration, such as round or square, matching or nonmatching, also could be employed.

Also by way of non-limiting example, the upper and lower shell portions 6a, 6b could be joined together using ultrasonic welding, a snap-fit, a press-fit, adhesive bonding, external fasteners, or any other suitable technique, whether now known or hereafter developed.

With continued reference to FIGS. 1A-B and 3A-B, handle 5 also includes a slot or recess 2 which receives a weight 30. Weight 30 serves to improve the balance of the handle 5 when the two shells 6a, 6b are joined together to receive the introducer needle 3. Preferably, weight 30 is chosen so that when the surgeon holds the assembly in his hand, the needle 3 rests horizontally and the needle tip 4 does not press down or up. In other words, the assembly should have neutral balance.

Alternatively, a surgeon may prefer a different, non-neutral weight balance, in which case the weight 30 could be selected accordingly.

As explained in detail below, the handle 5 may latch on and off of the introducer needle 3, preferably using the pushbutton release 9 on the handle 5, or, alternatively, via a smooth snap-on detent (not shown) that provides an audible "click" and/or a tactile confirmation when the introducer needle 3 is snapped into or out of the handle 5. The handle 5 is preferably removable because once the introducer needle 3 has been used to introduce the implant member 1 into the patient's body, it may be easier for the surgeon to separate the introducer needle 3 from the implant member 1 once the handle 5 has been separated. Also, a detachable handle 5 could be suitably sterilized and reused, which will reduce expenses.

As depicted in FIGS. 3A-B, 4A-B and 5A, the lower shell 6b of the handle 5 has a central slot 25 at its distal end designed to accept either end 4 of a symmetrical introducer needle 3', or the slightly smaller blunt end 16b of an asymmetrical introducer needle 3, which ends are dimensioned to fit closely through the slot 25, and provides a solid, secure attachment for the needle. The distal end of the handle 5 also may be tapered so as to effectively increase the working length of the introducer needle 3.

Figure 4A:
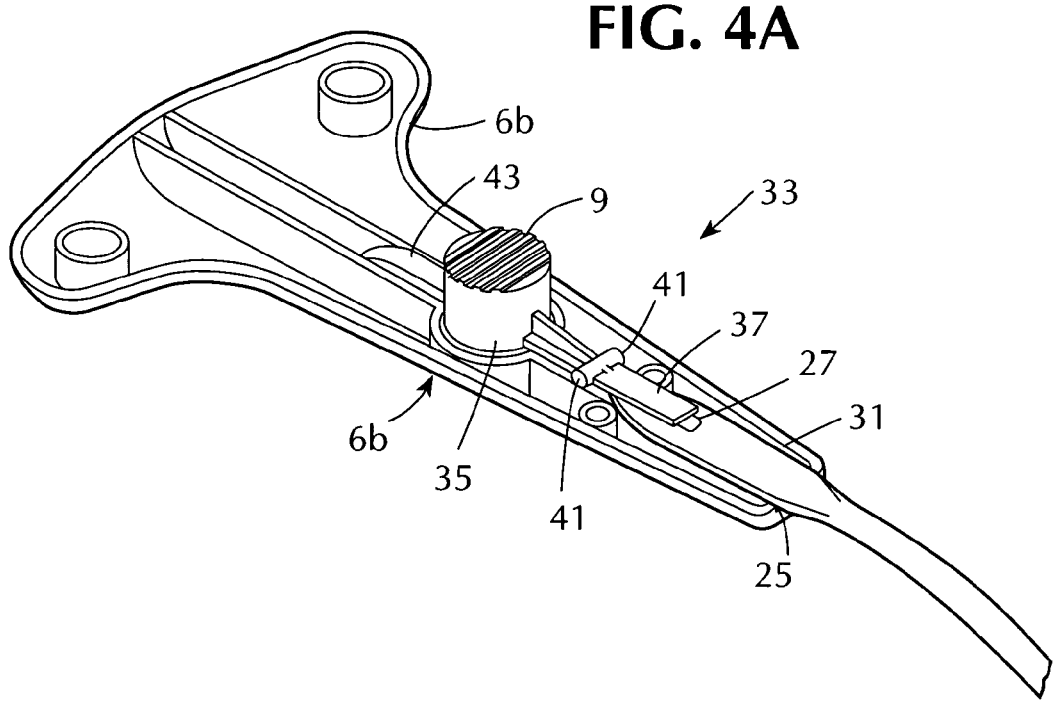
FIGS. 4A-B show the introducer handle with the top portion removed, FIG. 4B showing the components in exploded form.
Figure 4B:
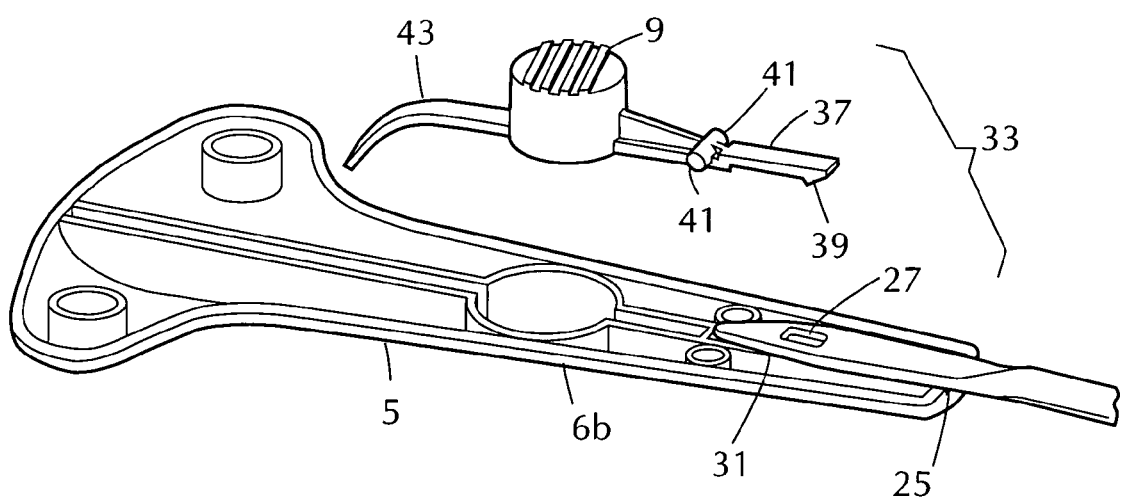

The handle 5 has internal structure arranged to accommodate and cooperate with a latch mechanism 33, as shown in FIGS. 1B, 3B, 4A and 4B. As best seen in FIGS. 3B and 4A, the latch mechanism 33 has a biased and pivotable elongated latch member 35 with a projection 39 which engages the opening 27 in the end 4 of the introducer needle 3. When the handle 5 is assembled as shown, the latch mechanism 33 securely holds the end 4 of the introducer needle 3 until the operator chooses to release the end 4 of the introducer needle 3 by pressing the button 9 on that latch mechanism 33.

As shown in FIGS. 1B, 3B and 4A, the elongated latch member 35 is received in the lower shell 6b of handle 5. The latch member 35 has an end catch section 37 with a triangular or rounded projection 39 that is sized and positioned to engage the opening 27 in the end 4 of the introducer needle 3 (in the case of the asymmetric needle, the blunt end 16b). As previously explained, and with reference now to FIGS. 6A and 6B, by making the two spatulated sections 13 of the introducer needle 3 differ in size and shape somewhat and by enlarging the needle end 16a which passes through the patient's tissue and which is sharper than the other blunt end 16b, the internal structure of the handle 5 can receive only the smaller blunt end 16b of the introducer needle 3. This prevents erroneous insertion of the sharper end 16a of the introducer needle 3 into the handle 5. Whereas the blunt end 16b of the introducer needle 3 received in the handle 5 has a generally rectangular shape, the end 16a of the introducer needle 3 that first passes through the patient's body has a triangular shape suitable for dissecting tissue as it advances. Also, the blunt end 16b of the introducer needle 3 received in the handle 5 has a width W that is narrower than the width W' of the other end 16a. Again, this difference is size and shape between the two ends 16a, 16b prevents misinsertion of the introducer needle 3 in the handle 5.

A further benefit of this arrangement is that the differing appearances of the flat, spatulated sections 13 provides a visual cue which helps the surgeon determine how to mount the introducer needle 3 in the handle 5.

With reference now to FIGS. 3B and 4A, moving in the proximal direction away from the end catch section 37, the elongated latch member 35 has a pair of projecting rounded pivot arms 41 which serve as pivots that rest upon part of the internal section of the lower handle shell 6b, and a pushbutton 9. The end 43 of the elongated latch member 35 located furthest from the end 4 of the introducer needle 3 curves downward toward the bottom of the lower handle shell 6b so that this end portion is bent when the elongated latch member 35 is held in the assembled handle 5. Bending the curved end 43 of the elongated latch member 35 generates a biasing force, which in turn is transferred via the rounded pivot arms 41 to the end catch section 37, thereby urging the projection 39 downward and toward the opening 27 in the end 4 of the introducer needle 3. This downward force keeps the projection in the slot formed in the needle tip, and thereby secures the needle tip 4 in the handle 5. Preferably, the curved end 43 generates a progressive resistance to applied force, so that as force applied to the elongated latch member 35 increases, further pressing of the pushbutton 9 becomes more difficult.

Alternatively, as shown in FIG. 5A, a separate spring 32 such as a helical spring can be mounted beneath the pushbutton 9 to oppose inadvertent downward movement of the pushbutton 9. As shown in FIG. 3B, this spring 32 also could be used with the curved end 43, for example, in case during the sterilization process, the curved end 43 permanently deforms, which would otherwise limit the force that such a curved end 43 could apply (other types of springs such as a leaf spring also could be used). This way, the introducer needle 3 is securely held in the handle 5 until release by the user.

Those skilled in the art will appreciate that as depicted in FIGS. 1B, 3B and 4A-B, the handle 5 which receives elongated latch member 35 has suitably-shaped internal contours to accommodate the various structural components of the elongated latch member 35 and introducer needle 3. Other schemes for securing the introducer needle also could be used.

Another preferred embodiment of a handle 5 in accordance with this invention will now be described with reference to FIGS. 5A and 5B. In this embodiment, handle 5 includes an insert 12 having a slot 14 which is dimensioned to accept the blunt end 16b of the introducer needle 3. This insert 12 is preferably made of a durable and dimensionally stable material which does not yield or abrade under the stresses applied and conditions experienced during use of this invention, and thereby serves to reinforce the handle 5. The insert 12 also adds weight to the handle 5 and helps to counterbalance the weight of the introducer needle 3 when the introducer needle 3 is joined to the handle 5. Preferably, the weight of the insert 12 matches the weight of the introducer needle 3 so that the device balances evenly in the surgeon's hand. By way of nonlimiting example, the insert 12 could be made from a machined or molded piece of stainless steel, aluminum, alloy metal, high-density plastic or other suitable material that has been suitably sterilized.

Each shell 6a, 6b of the handle 5 has an internal structure constructed to hold the insert 12 securely; by way of non-limiting example, the insert 12 has several recesses 18 which are dimensioned and disposed to receive posts 45 formed in the lower shell 6b of the handle 5. When the upper and lower shells 6a, 6b are joined together, the posts 45 and recesses 18 cooperate to hold securely the insert 12 in position.

In the embodiment depicted in FIGS. 5A and 5B, the elongated latch member 35 is biased by an abutting spring 32 so that the projection 39 presses downward into the slot or opening 27 formed in the tip of the introducer needle 3. As shown, the spring 32 presses the portion of the elongated latch member that is proximal to the projecting rounded arms 41 upward, and so the elongated latch member rotates about the projecting rounded arms 41 so that the distal end 37 of the elongated latch member 35, which has the projection 39 engaging the slot 27 formed in the end 4 of the introducer needle 3, is pressed downward toward the introducer needle 3.

It will be appreciated that the spring 32 or another suitable biasing member could be placed in a different location, for example, on the other side of the elongated latch member 35 in the area above and across from the projection 39.

To release the introducer needle 3 of any of the foregoing embodiments, the operator depresses the button 9 into the handle 5 with force sufficient to overcome the biasing force of the curved section 43 of the elongated latch member 35 and/or the pressing applied by the spring 32 to the elongated latch member 35. The button 9 pivots downward about the projecting rounded arms 41, and the projection 39 is raised upward and out of the opening 27 in the introducer needle 3. The introducer needle 3 then can be withdrawn from the handle 5.

It will be appreciated that the shape of the projection 39 is such that when, as shown in FIG. 3B, a introducer needle 3 is inserted into the handle 5, the surface of the projection 39 rides up onto the flat, spatulated section 13 of the end 4 of the introducer needle and is displaced upward above the advancing introducer needle 3. The introducer needle 3 continues to advance inward until the tip 4 of the introducer needle 3 reaches the end of the chamber dimensioned to accommodate the introducer needle 3, and the opening 27 in the introducer needle 3 is positioned beneath the projection 39, at which point the projection 39 is forced downward into the opening 27 through the urging force exerted by the curved section 43 of the elongated latch member 35. Now, the introducer needle 3 is securely joined to the handle 5, as depicted in FIGS. 3A-B and 9A-C.

Also by way of non-limiting example, pushbutton 9 and the opening 26 in the top shell 6a in which it is received are arranged so that the button surface is flush with the handle 5, and is positioned so that when the surgeon grasps the handle 5, the pushbutton 9 falls between the surgeon's fingers. This helps to avoid inadvertent release of the introducer needle 3 from the handle 5.

Furthermore, the elongated latch member 35 is preferably constructed so that it only releases the introducer needle 3 when the pushbutton 9 is fully-depressed; until then, the introducer needle 3 remains securely held in the handle 5. This way, a slight depressing of the pushbutton 9 from routine handling will not trigger release of the introducer needle 3. Furthermore, the opening in which the pushbutton 5 sits is contoured so that if the pushbutton 9 is inadvertently pressed by a hand or finger covering that opening, the introducer needle 3 is not released. These two features combine to reduce the likelihood of accidental introducer needle release.

All of these features combine to render it unlikely that a surgeon could inadvertently depress the pushbutton 9 while grasping the handle 5.

By way of non-limiting example, the upper and lower shells 6a, 6b of handle 5 are preferably manufactured by injection molding using a suitable plastic material. Any other suitable manufacturing technique, such as machining of a plastic or metal blank, also could be employed.

It will be appreciated that the dimensions and configuration of the handle shell 6a, 6b and any internal structure, such as the elongated latch member 35, should be selected so that the handle 5 can withstand the loads and torques experienced during use to advance introducer needle 3 and position the implant member 1.

The present invention also envisions the use of a handle 5 and introducer needle 3 which have been permanently joined together.

As part of the present invention, the introducer needle 3 and the "T"-shaped handle 5 are used to position the implant member 1 in the patient's body. This requires the needle 3 to be joined to the implant member 1. This is accomplished using a dual-ended connector 7, such as that shown in FIGS. 7A-D, 8A-G, 9A-D and 10. Such connectors 7 provide a permanent, snap-fit connection between introducer needles 3 and the implant member 1, and thereby ensure secure connection between those components during passage into the patient. "Permanent" means that it is not intended to be separated and so it would be difficult to manually separate a connector 7 from the introducer needle 3 or the implant member 1 after they have become permanently affixed (it does not, however, require that it be impossible to separate those parts). By providing a permanent connection, there is also less of a chance that a connector 7 could be left behind in the patient's body following completion of this procedure.

The ergonomically-designed handle 5 also could be straight, or a combination of straight and T-shaped for optimum grip during both the abdominal and vaginal approaches. A T-shaped handle 5 may be generally preferred by doctors for a vaginal approach, while a straight handle (not shown) may be generally preferred for an abdominal approach, and so a handle 5 which allows for both types of grips may be preferred and more practical. It will be understood that the precise manner in which the surgeon grips the handle 5 is a matter of individual preference, and that the gripping techniques disclosed herein are by way of non-limiting example.

Next, a number of different needles in accordance with this invention will be discussed.

With reference now to FIGS. 5A-B and 6A-B, the flat, spatulated section 13 of the needle end 4 is adjacent to a flared region 47. This flared region 47, owing to its size and profile, facilitates passage of the introducer needle 3 into the patient's body, and, after the implant member 1 has been joined to the introducer needle 3 by a connector 7, also facilitates withdrawal of the introducer needle and accompanying introduction of the connector 7 and attached implant member 1 into the patient's body. Preferably, seen in a direction perpendicular to the direction along which the needle end 4 is advanced into the body (the long axis of the introducer needle 3), the flared section 47 is somewhat larger in cross-section than the cross-section of the connector 7 that can be attached to the needle end 4. The connector 7 rides easily behind the flared section 47. Further, the shapes of the connector 7 and the flared region 47 are complementary.

The present invention contemplates the use of needles with and without the flared section. Examples of needle with the flared section can be seen in FIGS. 2, 3A-B and 4A-B. A needle having a flared section refers to a needle having a cross section at a given position such that the connector which follows the needle rides in the "shadow" of that given area. In other words, the width of the given area in any particular direction is at least as large as the width of the connector in the same direction. As discussed in detail below, the present invention discloses use of a needle having a flared section; seen in an end view, each point on the perimeter of the largest portion of the flared section lies on or outside of the perimeter of the largest portion of the connector which is drawn along by the needle.

Testing has showed that far less resistance is encountered over the connector 7 and implant member 1 when using a needle having the flared section, as compared to the use of a needle without such a flared section (not shown). A puncture test was conducted through a layer of porcine abdominal fascia using both types of needles. Whereas the needle with the flared section required 2.7 lbs. of force to penetrate through the fascia, the other type of needle required 3.2 lbs. of force to penetrate the fascia.

A second test was performed to evaluate the force over the connector 7 and implant member 1 after the initial opening was made. The test consisted of pulling each needle assembled with the connector 7 and implant member 1 through a layer of porcine abdominal fascia in a simulated-use test fixture. This test simulated the clinical use of the device being pulled through the rectus fascia or endopelvic fascia of a patient. The peak force measured using the needle without a flared section was 3.6 lbs., whereas and the peak force using the needle with the flared section and connector was 1.2 lbs.

For the needle without the flared section, the force to pull the connector 7 and implant member 1 through (3.6 lbs.) is higher than the initial penetration force (3.2 lbs.) For the needle having the flared section 47 and the connector 7, the force to pull the connector 7 and implant member 1 through (1.2 lbs.) is substantially lower than the initial penetration force (2.7 lbs.).

The general shape of needles which can be used with this invention will now be described.

As depicted in FIG. 2, the introducer needle 3' can be curved and double-ended. Each end 4 of the introducer needle 3 can interchangeably accept either the handle 5 or a connector 7 to be described. The curved central portion 11 of the introducer needle 3 is preferably circular in cross-section, although other cross-sectional profiles such as elliptical, hexagonal, square or triangular also could be employed. The curvature of the central portion 11 is sufficient to enable close tracking along the posterior surface of the patient's pubic bone between the abdominal and vaginal incisions. Consequently, it may be preferable to provide a range of different introducer needles, collectively sized to cover a range of different patient body sizes.

Each end 4 of the double-ended introducer needle 3' is spatulated with a thin, flat design to provide clean and atraumatic dissection, rather than cutting or piercing, of the patient's tissue during insertion. Because these two ends 4 have the same shape, each of the needle ends 4 can interchangeably engage either the handle 5 or a connector 7. Each end 4 of the double-ended needle 3' has a generally-arcuate central section 11 leading to a tip region having a flat, spatulated section 13. The size and precise shape of the spatulated section 13 can be selected to reflect the patient's anatomy. Preferably, the introducer needle 3' (or 3) is shaped to allow close tracking along the posterior surface of the pubic bone, keeping the needle tips 4 in the "zone of safety". The "zone of safety" is, generally, the area behind the posterior surface of the pubic bone between the upper and lower edges of the pubic symphysis. This area is relatively free of vasculature and other organs that could be damaged if the needle 3 were deviated too far posteriorly or laterally.

The flat, spatulated ends 4 provide a solid mounting surface for engagement with a slot 25 in the handle 5 by distributing the forces encountered during the procedure over a wide area inside the handle 5. Such forces may include compression, torque, bending and tension. The rounded needle tips 15 also serve to minimize unwanted perforations of the bladder and other vessels, while at the same time allowing the needle to gently dissect the patient's tissue as the needle advances into the patient's body. Although here the ends 4 of the introducer needle 3' are preferably the same size and shape, this invention is not to be so limited; as already explained, different size and shape ends also could be provided.

It also will be appreciated that the length, curvature and tip arrangement of the introducer needle 3' all affect the manner in which the introducer needle 3' tracks during use, and that this invention is intended to cover all such arrangements.

By way of non-limiting example, a curved introducer needle 3 according to this invention can subtend an obtuse angle, i.e., 98°, and have a bend radius of 4.7 inches, or can subtend a right angle, 90°, and have a 3.4 inch radius, or can subtend an acute angle, i.e., 60°, and have a 3.3 inch radius.

Again, all of these dimensions have been given by way of example only and not limitation. Other dimensions also could be used.

Also optionally, and with reference now to FIGS. 5A-B, the portion of the introducer needle 3 leading to the flat spatulated sections 13 could be straight, so that a straight section 20 is located between the curved section and at least one of the needle ends 4. Such straight sections 20 are presently thought to be of particular use with an introducer needle 3 having a right angle bend, and also could be used with other needle configurations.

By way of nonlimiting example, and with reference to FIGS. 5A-C, the introducer needle 3 can be constructed with an asymmetric geometry such that the curved section 22 is provided near the distal end, and the portion of the introducer needle 3 located between the surgeon and the curved portion 22 is longer than the portion of the introducer needle 3 projecting forward from the curved portion 22. This arrangement provides added working length at the proximal end of the introducer needle 3, which improves handling, while the shorter segment at distal end of the introducer needle 3 can better conform to the pubic bone as it advances. The increased length of the proximal end of the introducer needle 3 also permits the use of a longer handle 5, which may allow for more precise positioning of the introducer needle 3.

Presently, it is thought to be preferable to round the needle ends 4 for maximum safety. However, the ends could be sharp-edged or even pointed to facilitate penetration through the fascial layers during insertion.

Each end of the introducer needle 3 has an opening or slot 27 therethrough. As depicted in FIGS. 2 and 6A-B, the openings 27 are preferably rectangular, although other shapes, such as circles, ovals, squares and triangles also could be employed. More than one opening 27 also could be provided in each end 4. These openings 27, as will be explained in greater detail below, are used to join one end 4 of the introducer needle 3 to a handle 5, and also to connect the other end 4 of the introducer needle 3 to the implant member 1.

The introducer needle 3 can be made of any suitable biocompliant material such as stainless steel. If desired, the introducer needle 3 could be coated with a low-friction layer of material (not shown) such as polytetrafluoroethylene to reduce insertion trauma.

Figure 5D:
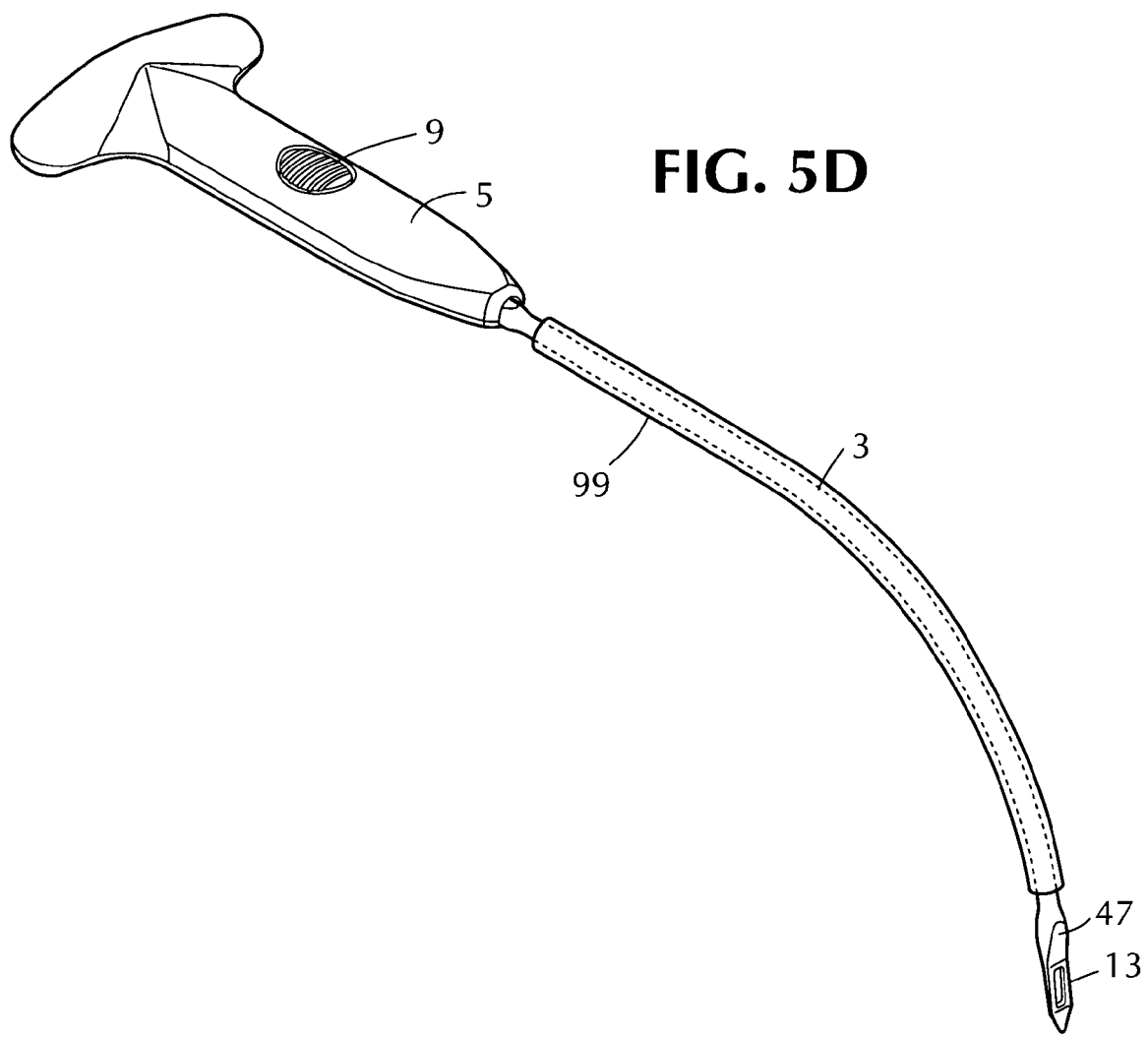
FIG. 5D illustrates the needle received in the handle and covered by a sheath.

Optionally, and with reference now to FIG. 5D, the introducer needle 3 could be provided with a shrink-tubing sleeve. Such a sleeve would serve two purposes; first, if made of PTFE (Teflon®) or similar material, it could provide a very lubricious surface to ease passage of the introducer needle 3 through the body, while at the same time preventing injury to the body tissue. Secondly, the sleeve could be made in a very bright color such as green or blue to improve visibility during a cystoscopy to confirm bladder integrity. Even if bladder perforation is not observed, the bright color of the sleeve can be seen through the thin bladder wall confirming safe placement of the introducer needle 3.

As depicted in FIG. 5D, the sheath is tubular, with open ends; however, it will be appreciated that the distal end of the sheath could be closed to further facilitate advancement of the introducer needle 1 into the patient's body. If desired, the closed end of the sheath could be cut off once the sheath has entered and passed through the patient's body, for example, when it protrudes through an abdominal incision.

With reference now to FIG. 13, the connector 7 is used to obtain a positive, snap-fit connection between the introducer needle 3 and the implant member 1 to ensure secure attachment during passage of the introducer needle 3 and the implant 1 into the patient. Preferably, the connector 7 is flexible, and permanent. Several different embodiments of connectors according to this invention now will be described.

To minimize tissue trauma during use, all of the surfaces of the connector 7 are preferably tapered and/or rounded, and have a low-friction surface. The connector 7 can be made from a low-friction, biocompatible material, and, if desired, can be surface treated or coated to improve its properties.

To further minimize tissue trauma, it is preferable to have, as depicted in FIGS. 9A-D and 15A-C, the tips of the arms of each connector 7 which abut the flat, spatulated section 13 of the introducer needle 3 be shaped to conform to the tapered end 4 of the introducer needle 3 (in other words, these parts have complementary shapes). Preferably, the ends of the connector 7 that abut the flat, spatulated section 13 of the introducer needle 3 have flexible tips that conform snugly to the end 4 of the needle 3. Also, the arms of the connector are preferably long enough so that they cover much of the flat, spatulated section 13 of the introducer needle end 4 and come close to the flared region 47 of the needle end 4.

FIGS. 7A-D depict a first embodiment of a connector 7 having limited flexible construction. This design allows for the connector 7 to pivot and bend freely about certain axes during passage into the body (rotation around the locking projection 57 and bending at the mid joint or web 51) to better follow the curved path created by the introducer needle 3.

Connector 7, as shown in FIGS. 7A-D, is symmetrical about a vertical plane. Each side of the connector 7 is designed for attachment to either the introducer needle 3 or the implant member 1, and, since the connector 7 is symmetrical, the two sides are interchangeable. This means the surgeon, when joining the connector 7 to the introducer needle 3 or implant member 1, does not have to spend time choosing a particular side of the connector 7 for attachment.

In this connector 7, the two lower arms 53a, 53b on each side of the connector 7 are joined directly to a central web 51. Each arm 53a, 53b, 55a and 55b can have a narrower region 56 which serves as a living hinge. The living hinges 56 could be molded directly or formed by machining portions of the arms 53a, 53b. The projections 57 extending upward from the lower arms 53a, 53b toward opposing upper arms 55a and 55b, respectively, are generally cylindrical in shape (and, more preferably, are frusto-conical), with a flared end cap 59. Openings 61 are formed at positions opposite to the projections 57. Each opening 61 has a beveled inner surface 63 dimensioned to receive the end cap 59 of the associated lower arm 53a, 53b, and at least one slot 65. The slot 65 allows the beveled inner surface 63 of the opening 61 to deform sufficiently to receive and allow passage of the flared end cap 59. Once the flared end cap 59 passes completely through the opening 61, the deformed inner surface 63 of the opening 61 returns to its normal position, and the flared end cap 59 cannot be retracted therethrough. Although the flared end cap 59 may project somewhat from the flat back surface of the upper arm 55a or 55b, the rounded shape of the flared end cap 59 means it still will pass smoothly through the patient's tissue during insertion of the implant member 1.

Figure 7A:
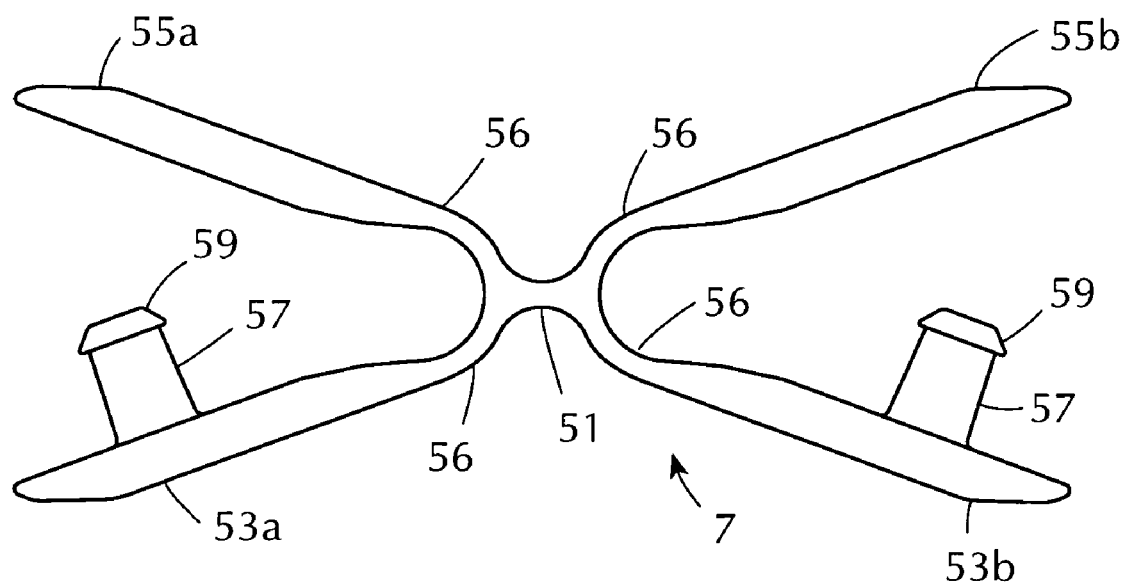
FIG. 7A is a side elevational view of a permanent snap connector according to a first embodiment in the open position.
Figure 7B:
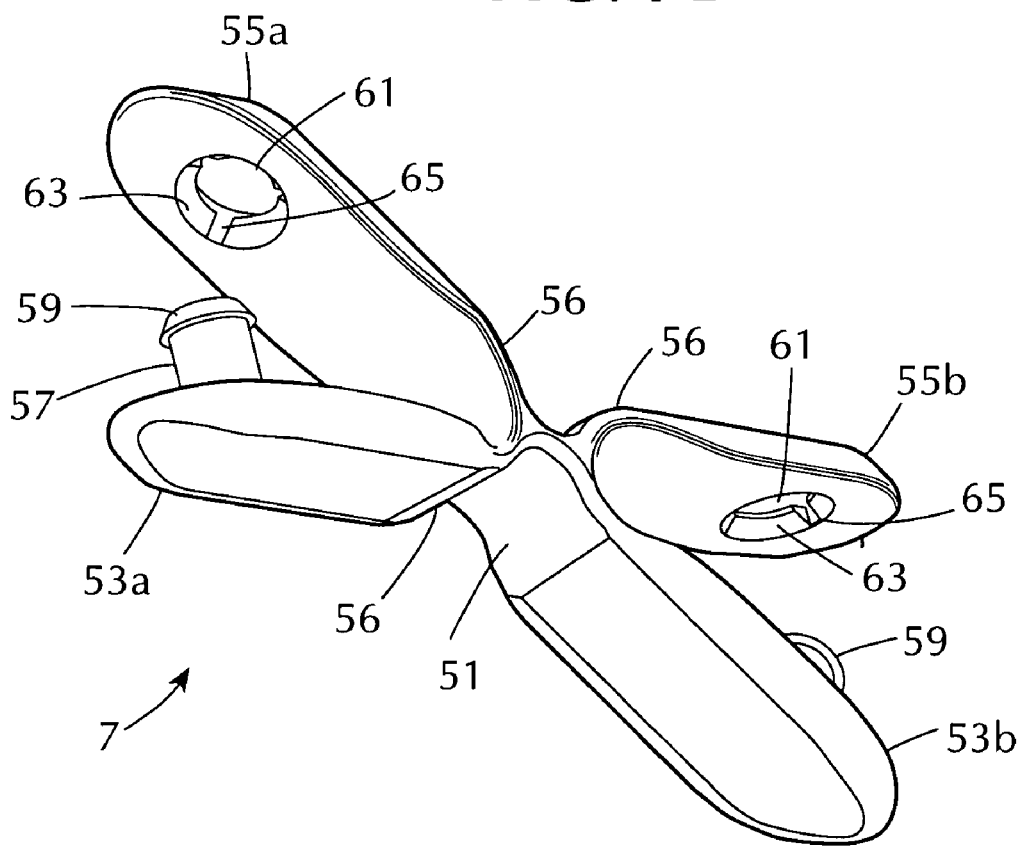
FIGS. 7B and 7C are perspective views in the open and closed positions.
Figure 7C:
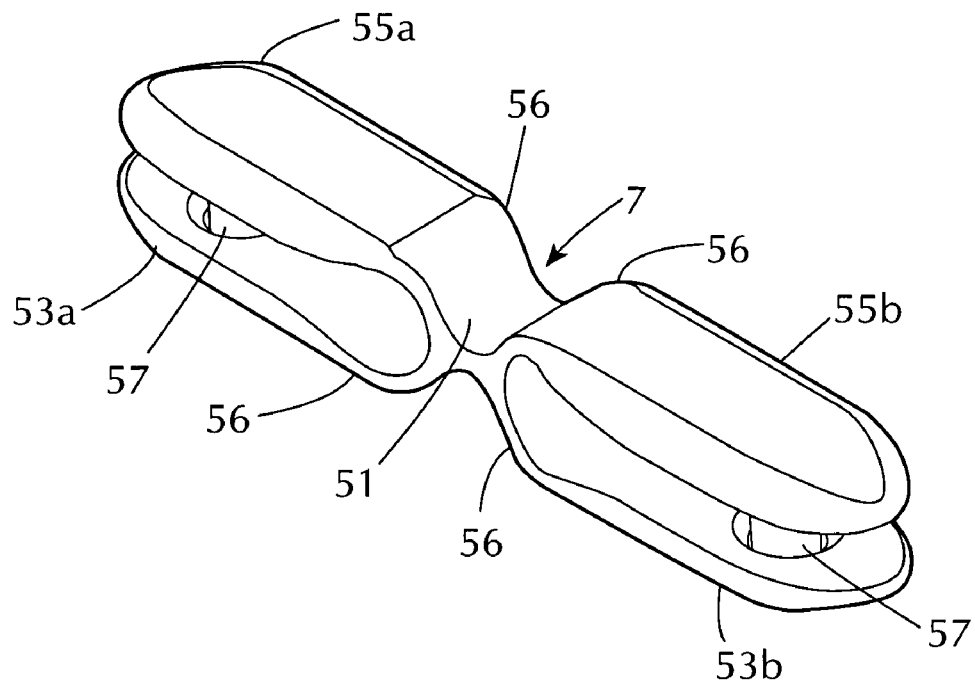
Figure 7D:
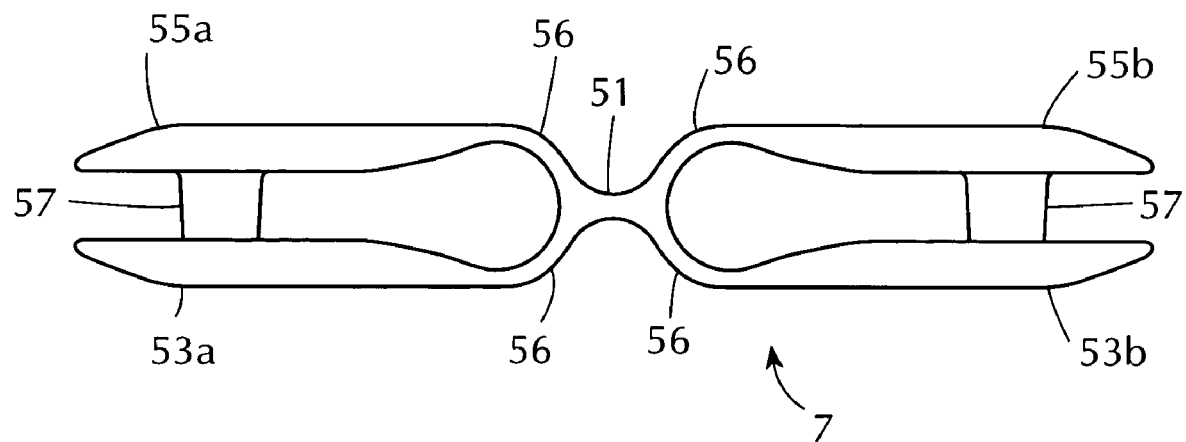
FIG. 7D is a side elevational view in the closed position of the connector shown in FIG. 7A.

FIGS. 7C and 7D show the connector 7 when each pair of upper and lower arms 53a, 53b, 55a and 55b are respectively brought together and locked by engagement of the flared end cap 59 with matching openings 61.

Figure 8A:
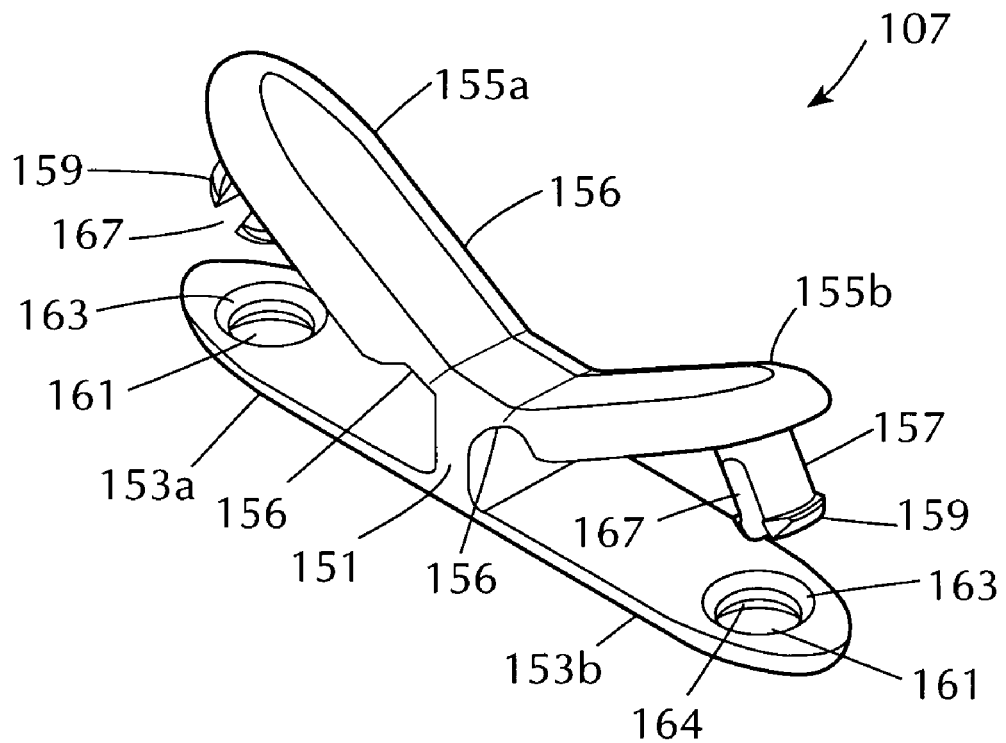
FIG. 8A is a perspective views of a second embodiment of a permanent snap connector design, FIG. 8B being a side elevational view of the connector shown in FIG. 8A.
Figure 8B:
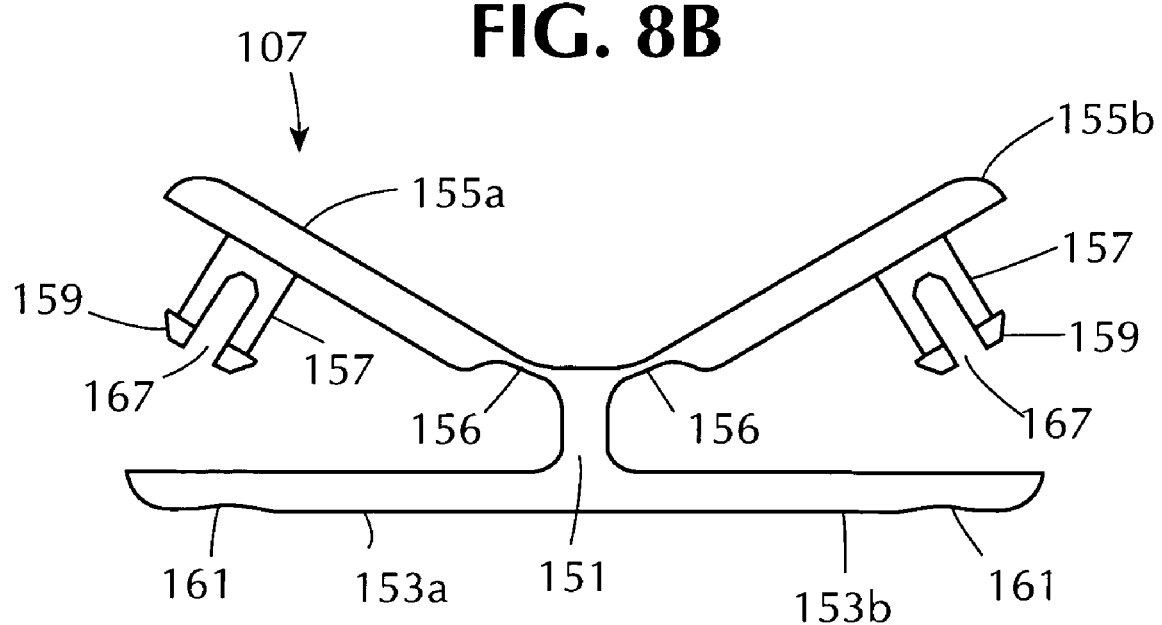

FIGS. 8A and 8B show an alternate embodiment of a connector 107 that is similar to the connector 7 just described. In this arrangement, only the upper arms 155a and 155b of the connector 107 are bendable about narrower regions 156 serving as living hinges. The lower arms 153a, 153b are fairly rigid, owing to their thickness and the lack of hinge areas, and they lie in a plane. A central web 151 extends upward perpendicular to the plane in which the lower arms 153a, 153b lie, and the upper arms 155a, 155b are attached to this central web 151. As shown in FIG. 8B, the upper arms 155a, 155b are joined to the central web 151 by living hinges 156. Here, frusto-conical projections 157 extend from the upper arms 155a, 155b toward the opposing lower arms 153a, 153b, which have matching openings 161 formed therein. Connector 107 is preferably made from a biocompatible polymeric material. To simplify manufacture and use, the connector 107 is preferably formed as a molded integral unit, but also could be made from separate components suitably connected.

Also alternatively, the connector 107 could be machined in its entirety.

As shown in FIG. 8A, each opening 161 has a beveled inner surface or countersunk portion 163 and counterbored portion 164, for reasons described below.

The end of the projection 157 has a flared end cap 159 which is sized and positioned to engage and cooperate with the beveled edge 163 of the opposed opening 161. Preferably, at least one slot 167 is formed extending through the projection 157. This way, when the arm 153a, 153b is moved toward the opposing arm 155a, 155b, the beveled surface 169 on the end of the projection 157 strikes the beveled edge 163 of the opening 161, urging the divided portions of the projection 157 toward each other. As the divided portions of the projection 157 move inward, they can pass between the edges of the opening 161, until the halves of the projection 157 extend outward from the bottom surface of the elongated lower arms 155a, 155b. The halves of the projection 157 are received in the counterbored portion 164 of the opening 161. The counterbored portion 164 is preferably dimensioned so that the flared end cap 159 does not project outward from the upper arm 153a, 153b. This way, the connector 107, when closed, still has a smooth, projection-free outer surface which is easily drawn through the patient's tissue during implant member insertion.

The halves of the projection 159 then spring out and engage the back surface of the lower arms 155a, 155b, and prevent the projection 157 from being drawn back through the opening 161.

Accordingly, the connector 107 shown in FIGS. 8A and 8B provides a more rigid structure than the previous connector 7, and may be preferred in view of a particular patient's anatomy, or in view of the surgeon's own preferences.

Figure 9A:
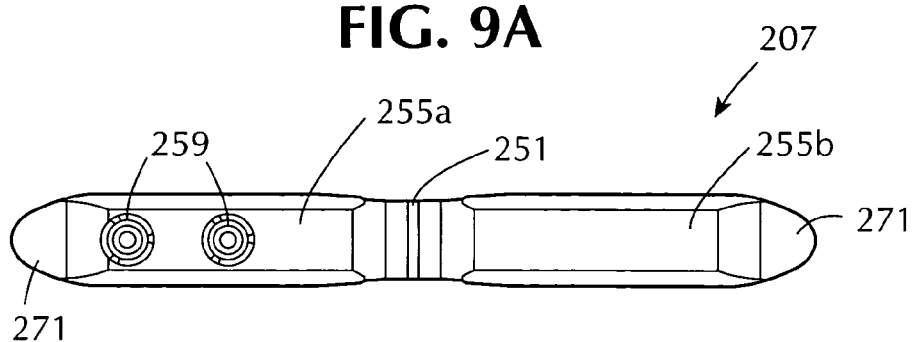
FIGS. 9A-C are, respectively, top plan, side elevational and front elevational views of a further connector in accordance with this invention, the connector being in a closed configuration.
Figure 9B:
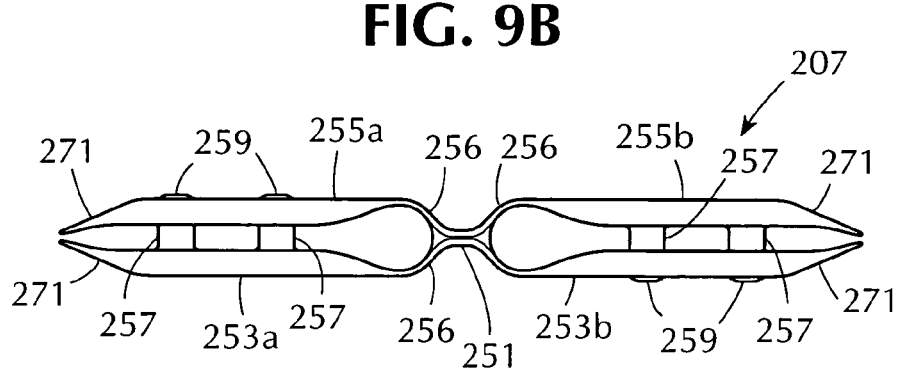
Figure 9C:
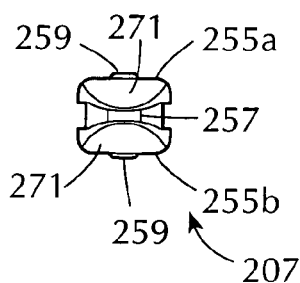

FIGS. 9A-C depict yet another embodiment of a connector 207 similar to that shown in FIGS. 7A-D. In the embodiment depicted in FIGS. 9A-C, each pair of arms 253a, 253b, 255a, 255b has two, rather than one, projections 257, each projection 257 again having a flared end cap 259. The opposing arm 253a, 253b, 255a, 255b has openings 261 sized and located to receive and securely hold the flared end caps 259. As before, the arms 253a, 253b, 255a, 255b are attached by living hinges 256 or more flexible sections, to a central web 251. The tip portion 271 of each arm 253a, 253b, 255a, 255b is tapered in thickness, and the tip portions 271 all are angled slightly to approach one another. This slight inward bend at the ends of the connector 207 helps provide a compressed, snug fit when snapped onto the introducer needle 3 or implant member 1. This way, when the connector 207 is joined to the implant member 1, the tip portions 271 of the arms 253a, 253b, 255a, 255b squeeze the implant member 1 somewhat. The tapered shape of the tip portions 271 also facilitates movement of the connector 207 through body tissue.

The use of two projections 257 in each side of the connector 207 provides several benefits. First, it improves the strength of the snap-lock by distributing the loads over the greater area of the two projections 257. Second, the dual projection design improves the connection to the implant member 1 by distributing the forces over two holes in that member, instead of one. Third, the dual projection design prevents rotation/pivoting of the connector 207 on the needle 3. This may help prevent "kinking" of the connector 207 on the needle 3 if the movement of the introducer needle 3 is reversed. However, the connector 207 may still flex in the center about the central web 251 along the longitudinal direction to better conform around the curved pubic bone during passage.

The dual projections 257 used in the connector 207 shown in FIGS. 9A-C provide stronger connections between the implant member 1 and the connector 207 and the introducer needle 3 and the connector 207, and they redundantly protect against failure of any one projection 257. Also, using two projections 257 prevents rotation of the implant member 1 or introducer needle 3 about those projections 257 (in the case of the introducer needle 3 the projections 257 are preferably received in an elongated slot 27 just able to accommodate the projections 257), which could happen if a single projection were to be used. This may prevent or at least reduce "kinking" of the connector 207 or the implant member 1 during placement in the body.

Although FIGS. 9A-C show that the projections 257 for one pair of arms 253a, 253b, 255a, 255b are located so as to extend upward and the projections 257 of the other pair of arms 253a, 253b, 255a, 255b extend downward (in other words, the projections 257 face in opposite directions), it will also be understood that the projections 257 could be positioned so that they face in the same direction.

Figure 9D:
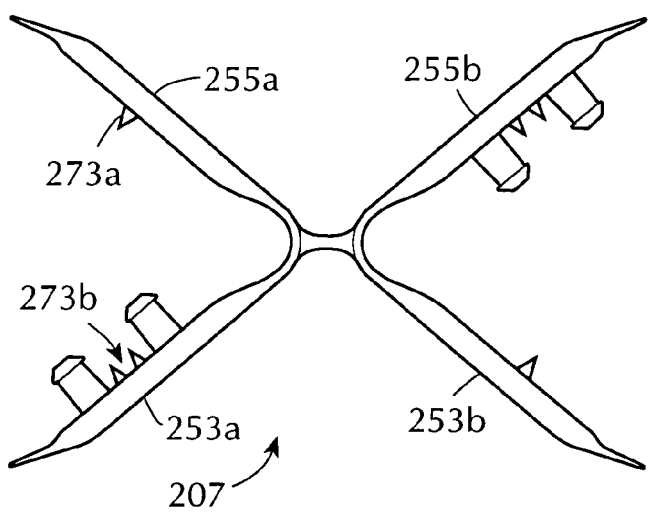
FIG. 9D is a side elevational view showing the same connector in an open configuration.

FIG. 9D depicts a further refinement of the connector 207 shown in FIGS. 9A-C. While the two connectors 207 are generally the same in appearance, the connector 207 shown in FIG. 9D has, in addition to each pair of arms 253a, 253b, 255a, 255b having two projections 257 and matching openings 261, a set of opposing and interlocking teeth 273a, 273b dimensioned and disposed to mate when the connector arms 253a, 253b, 255a, 255b are brought together. These teeth 273a, 273b can improve the connector's bite into the implant member 1. On the introducer needle 3, these teeth 273a, 273b mesh together inside the slot 27 and help prevent improper closure of the connector 207 on the introducer needle (which now has a single elongated slot 27 that allows integration with both the connector 207 and the handle 5).

As shown, the upper arm 255a on the left side has a single tooth 273a, and the facing lower arm 253a has two teeth 273b. In this embodiment, when the connector 207 is closed, the one tooth 273a of the left upper arm 255a fits between the two teeth 273b of the left lower arm 253a. When such a connector 207 is joined to the implant member 1, these teeth 273a, 273b will bite into and thereby capture the implant member 1. However, when the connector 207 is joined to the needle end 4, which has an elongated slot 27 therein, the teeth 273a, 273b will just close together without any material therebetween.

Figure 10:
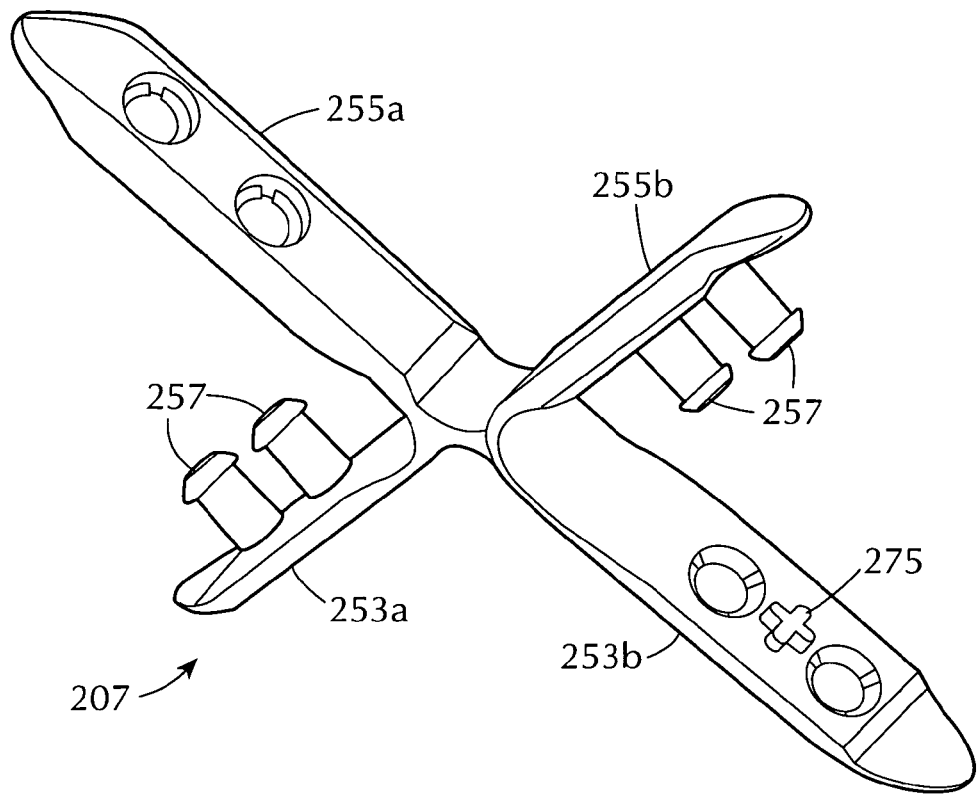
FIG. 10 is a perspective view of a modified version of the connector shown in FIGS. 7A-D.
Figure 11A:
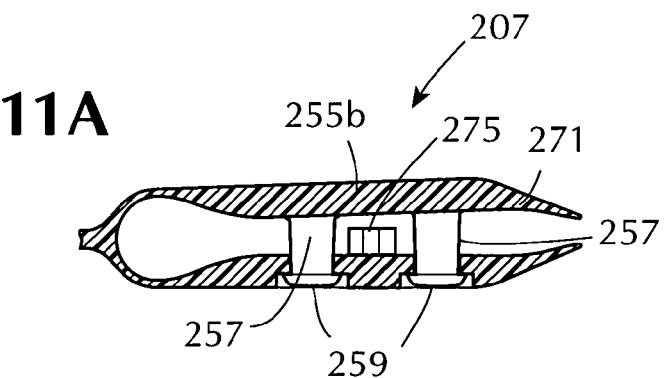
FIGS. 11A-B are side elevational views showing how the connector of FIG. 10, in closed configuration, resists the application of closing force.
Figure 11B:
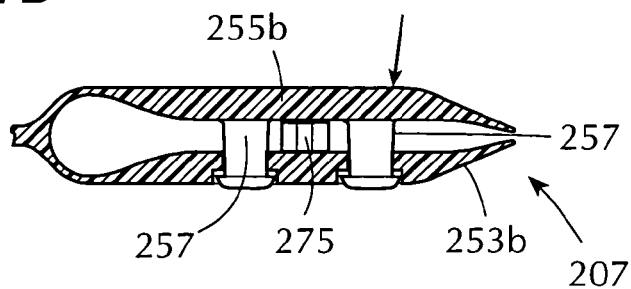

FIGS. 10 and 11A-B depict still another embodiment of a connector 207 in accordance with this invention. This embodiment is substantially similar in configuration to the connectors 207 shown in FIGS. 9A-D, but differs in that the teeth 273a, 273b of FIG. 9A have been replaced by a "+"-shaped boss or projection 275 (it should be understood that any other suitable shape boss also could be used, such as a hemispherical or cylindrical boss in place of the "+"-shaped projection 275). The "+"-shaped projection 275 is located on one of each of the two arms 253a, 255a or 253b, 255b making up each side of the connector 207. As shown in FIGS. 11A and 11B, the "+"-shaped projection 275 does not extend all the way from one arm to the other—rather, the "+"-shaped projection 275 is about half the height of the gap between the opposing arms 253a and 255a or 253b and 255b. When the opposed arms on either side of the connector 207 are squeezed together, the "+"-shaped projection 275 limits how close together the opposing arms 253a and 255a or 253a and 255b can be pressed. As shown in FIG. 11B, which depicts the "+"-shaped projection 275 being formed as part of, and extending upward from, the lower arm 255b, if the two opposing arms 253b, 255b are pressed together by sufficient force, the upward-facing "+"-shaped projection 275 strikes the upper arm 255b and prevents further compression. This keeps the two arms 253b, 255b separated by the height of the "+"-shaped projection 275. When the connector 207 is attached to the implant member, the separation maintained between the two arms 253b, 255b, becomes the height of the boss plus the thickness of the implant member.

The "+"-shaped projection 275 also helps to prevent improper connection to the introducer needle 3; for example, while a connector 7 such as that shown in FIGS. 7A-B could be connected sideways to an introducer needle 3, here the "+"-shaped projection 275 will interfere with the needle 3 unless both of the connector's cylindrical projections 257 are aligned with the slot 27 in the needle 3.

It will also be appreciated that the "+"-shaped projection 257, since it limits inward movement of the facing arms 253a, 255a and 253b, 255b ("oversnapping"), also can control the pressure that the arms 253a, 255a and 253b, 255b apply to an implant member 1 held therebetween. This may avoid unnecessary material damage.

Preferably, the "+"-shaped boss 275 has rounded and blunt surfaces, and it does not bite or clamp down on the implant member 1. Accordingly, this structure should not be viewed as a tooth.

Figure 51A:
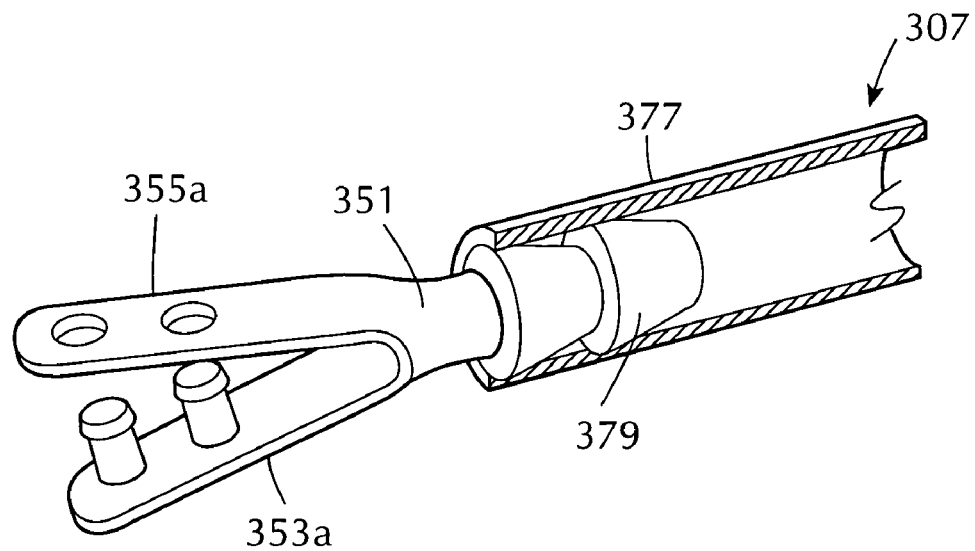
FIGS. 51A and 51B are perspective and side cross-sectional views showing another embodiment of this invention.
Figure 51B:
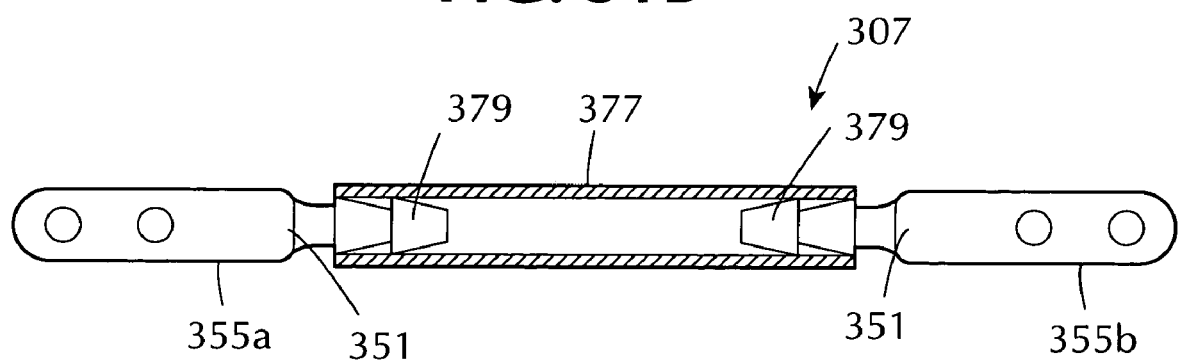

FIGS. 51A and 51B show yet another connector configuration. This connector 307 has a pair of upper and lower jaws 353a, 353b, 355a, 355b which are linked together by a length of flexible tubing 377. The length and stiffness of the tubing 377 can be chosen according to the properties required for the connector 307. Each upper and lower jaw section has upper and lower jaws 353a, 355a which come together at one side of a center body 351, and a barbed connector 379 located on the other side of the center body 351. The barbed connector 379 is dimensioned so that when it is inserted into the flexible tubing 377, the barbed connector 379 secures the upper and lower jaw sections 353a, 355a against backward movement.

Figure 14A:
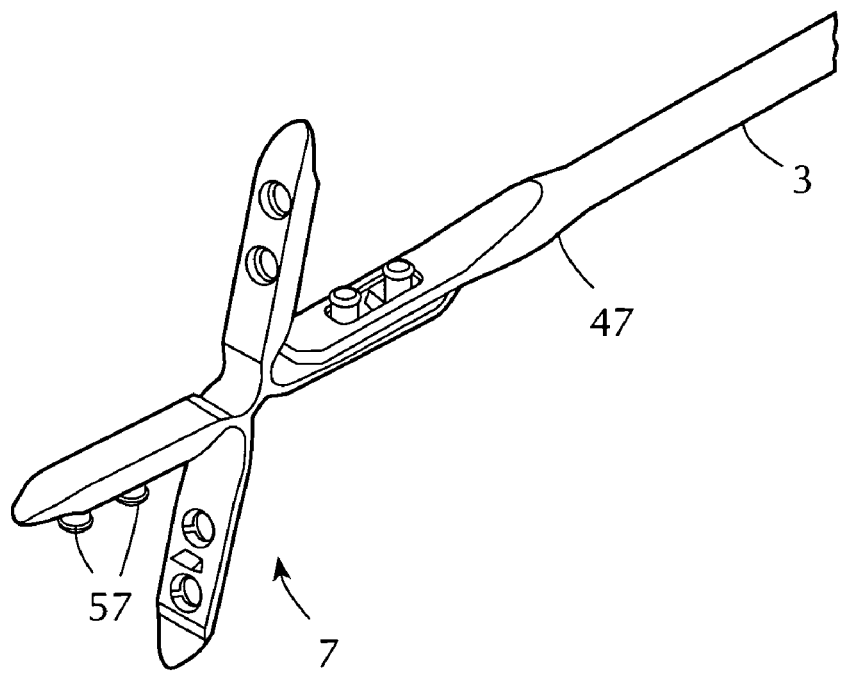
FIGS. 14A and 14B are perspective views showing the connector of FIGS. 9A-D being affixed to an introducer needle.
Figure 14B:
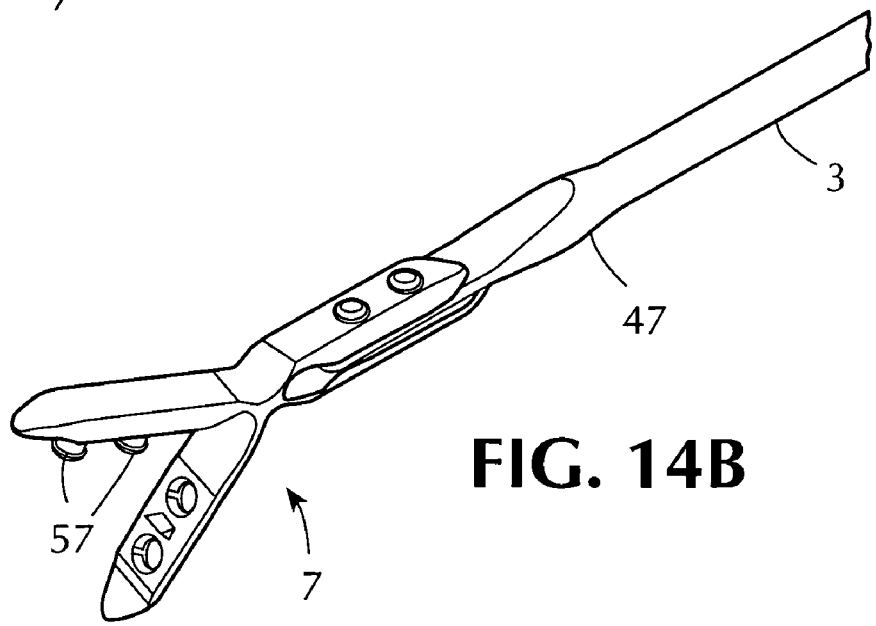
Figure 16A:
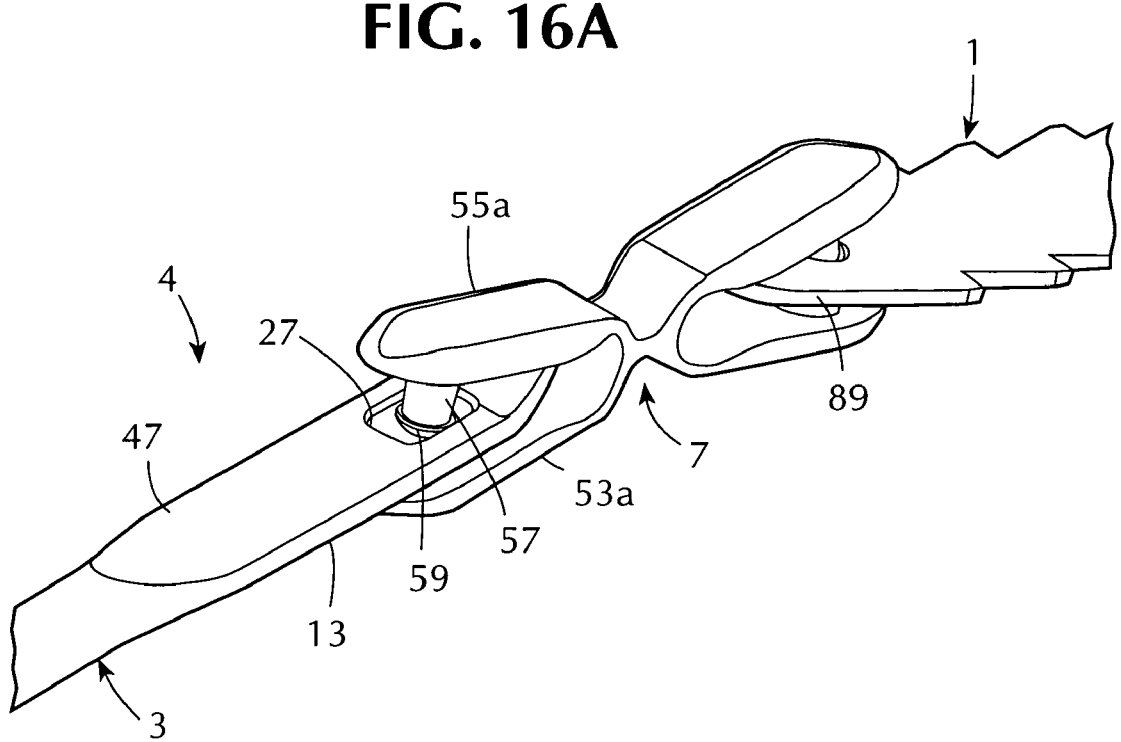
FIGS. 16A-D are perspective views showing the assembly of an introducer system and implant member in accordance with the present invention using the connector depicted in FIGS. 7A-D.
Figure 16B:
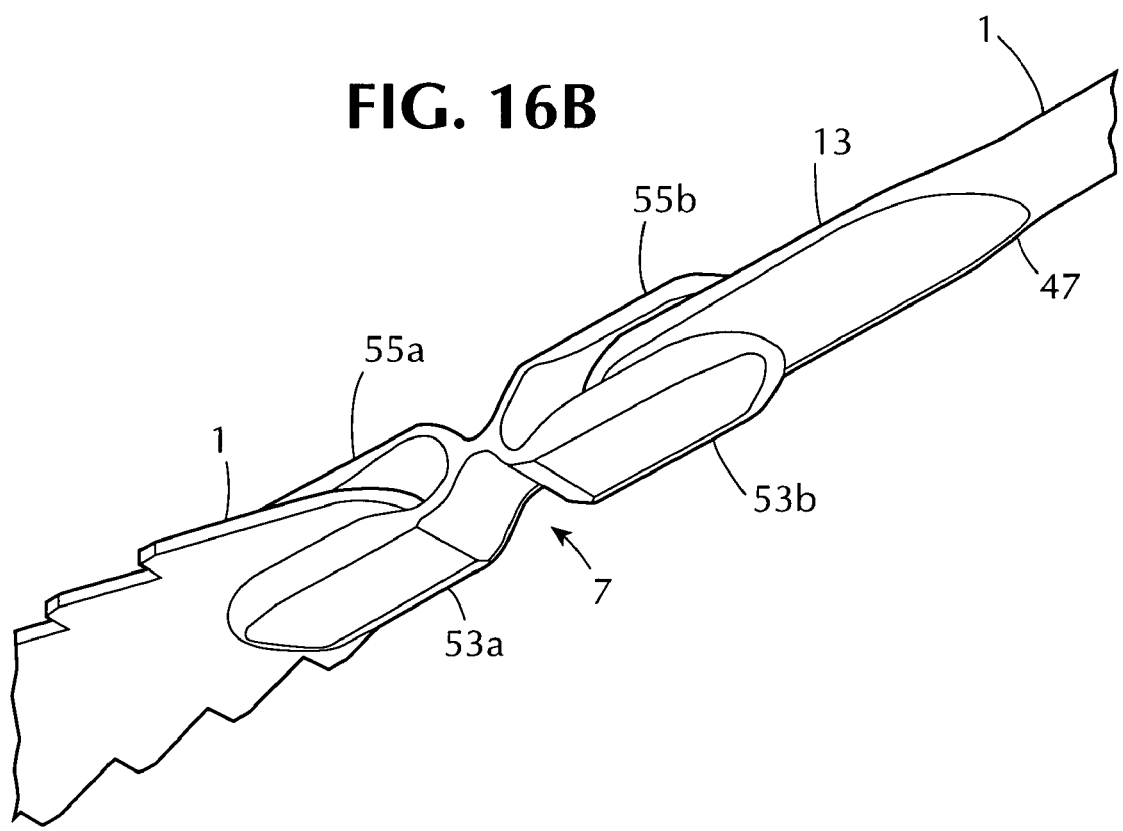
Figure 16C:
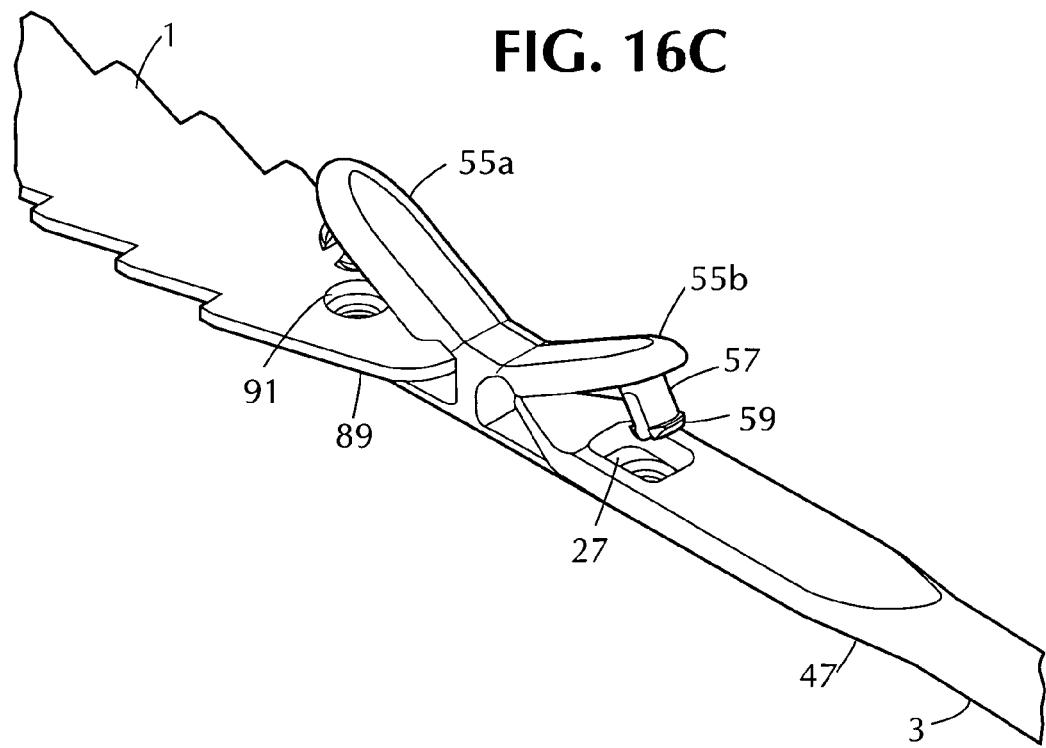
Figure 16D:
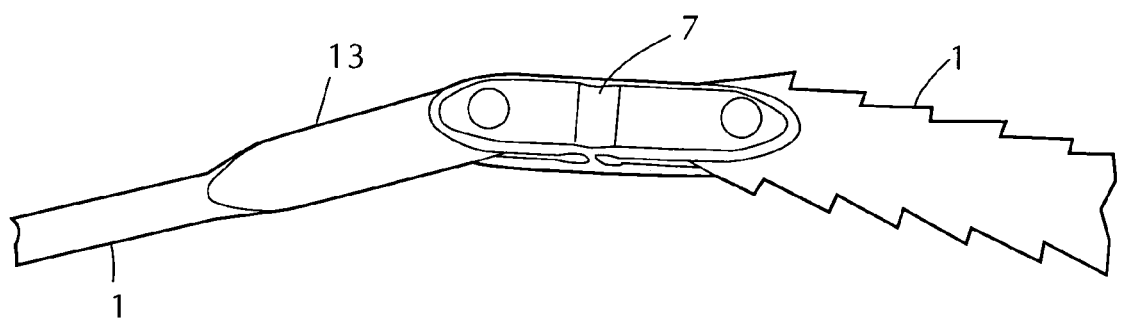

With reference now to FIGS. 6A, 6B, 14A, 14B and 15A-C, aspects of this invention are depicted in which the needle tip 4 and the connector 7 are designed with complementary shapes such that the advancing introducer needle 3 passes through the tissue prior to movement of the connector 7 therethrough, as will now be described (FIGS. 14A-B depict the connector of FIG. 9D but, for simplicity, the numbering of connector 7 has been employed). The needle 3 has a flared section 47 that, when seen perpendicular to the needle's axis, extends over at least the same area as the connector 7, and, more preferably, over a somewhat wider area than the connector 7. The flared section 47 precedes the connector 7 and implant member 1 through the tissue. The flared section 47 thereby reduces the amount of force required to create the implant passageway. As the passageway is created by the introducer needle 3, the connector 7 and implant member 1, which are attached to one end of the introducer needle 3, follow the needle into the tissue channel. The connector 7 and implant member 1 are "shadowed" by the flared section 47 of the introducer needle 3 during passage through the tissue. This way, the tissue channel is formed without substantial trauma to the patient's tissue, and the tissue channel is large enough so that the connector 7 and implant member 1 can pass through without causing injury to the tissue and without difficulty.

As depicted in FIGS. 12, 17A-D and 20A-E, the implant member 1 is an elongated strip of material about 30-50 cm long and 1-2 cm wide. In the embodiments shown in FIGS. 12, 17A-D, 20A and 20C-E, the implant member 1 has a center section 81 flanked by arm portions 83a, 83b. Preferably, the implant member 1 is symmetrical. In many cases the arm portions 83a, 83b include slits 85 that improve the implant member's anchoring properties, whereas the center section 81 does not have such slits. Alternatively, the edges 87 of the arms 83a, 83b could be smooth, scalloped, or even have irregular shapes formed thereon. The tips 89 of the arm portions 83a, 83b are rounded, and each tip 89 has one or more openings 91 therein, the purpose of which will be discussed elsewhere.

The center section 81 is preferably dimensioned so that, when the implant member 1 is positioned in the patient's body, the center section 81 helps to distribute force in the region of the urethra in a manner to provide a backboard or support that enables urethral closure when abdominal pressure increases occur.

In one embodiment of this invention, each of the arm portions 83a, 83b preferably has a length sufficient so that when the implant member 1 is first implanted in the manner discussed below, the tips 89 of the arms 83*a*, 83*b* protrude outward from the patient's body. Thus, the arms 83*a*, 83B should be sized for use with the largest patients likely to undergo this procedure. The protruding tips 89 of the arms 83*a*, 83*b* can be manipulated by the surgeon to properly position the implant member 1, and also to apply the desired amount of tension to the implant member 1.

Given these dimensional considerations, it may be preferable to provide a range of different sized implant members to better accommodate the physiologies of different sized patients. Implant member width, the length of the center section 81 and of the arms 83*a*, 83*b* all could be varied to provide a number of different implant members 1. Implant member shape and dimensions can be selected according to the holding force desired.

Figure 22A:
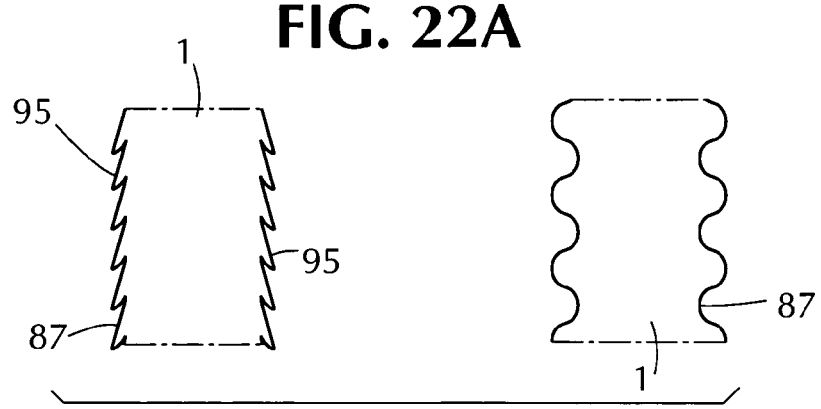
FIGS. 22A-F are views showing various implant member configurations.

The arms 83*a*, 83*b* of the implant member 1 shown in FIGS. 12, 13 and 22A have "sawtooth" or "wave" shaped outer edges 87. This arrangement will help anchor the implant member 1 in the patient's tissue, and will secure the implant member 1 against unwanted movement.

Other possible edge styles that allow for easy insertion in the tapered direction, but that also resist movement in the opposite direction include uniform "saw-tooth" edges 87 and smooth curved edges 87. Each edge style can either be deep or shallow to generate higher or lower amounts of self-anchoring force. The edges 87 can also have numerous small slits 93 to help generate additional anchoring ability and possibly more adjustability in the surrounding tissue through out-of-plane deformation of the material between the slits 93, as discussed in greater detail below. By way of further non-limiting example, a plain, straight-edged implant member 1 also could be used, whether of constant width or having a different width in the region of the urethra.

An implant member 1 having an irregular edge 87 could support a greater force than an implant member 1 having a straight edge 87. Larger serrations should provide better holding power, but cannot be adjusted in position as easily; the serrations or projections 95 act as "ratchets", and a finely pitched ratchet, it will be appreciated, can be adjusted more precisely.

By way of non-limiting example, one configuration of the implant member 1 is a 10-15 mm wide strip with directional texturing about 1-2 mm deep on each side. The spacing between each peak of the edge texture (the "teeth") 95 is preferably in the range of 2-10 mm. This spacing characteristic can provide maximum adjustability (an analogy is to a belt-closer spaced holes in the belt allow smaller and more precise adjustments). Also, the implant member 1 is preferably 30-50 cm in length, and has an untextured center section 81 approximately 1-15 cm long, with 2-10 cm. being more preferable. Arm widths of 12 mm and center section widths of 15 mm may be preferred.

It should be understood that as the number and size of the projections (teeth) 95 increase, the force which the implant member 1 can withstand also increases.

In one embodiment, the projections 95 on the edge of the implant member 1 could be 1.5 mm deep, 6 mm. apart in pitch, and the implant member 12 mm wide at its widest portion. Again, these dimensions are exemplary, and other dimensions also could be used.

The use of inner slits 85, rather than sawtooth-shaped outer edges 87, may be preferred because an implant member 1 with inner slits 85 may be easier to position than an implant member with sawtooth-shaped outer edges 87. By virtue of the slits' shape, the implant member 1, as it is introduced into the patient's body, slides easily through tissue, since the low force required to pull the implant member 1 behind the flared section 47 of the introducer needle 3 means that the internal slits 85 will lie flat in the same plane as the rest of the implant member 1, and will not interfere with insertion of the implant member 1.

The use of "V"-shaped slits 85, as depicted in FIGS. 17A, 17C, 17D, 18A-B and 19A, and others, is presently preferred. Implant members 1 constructed in this manner have a dynamic and centrally-located self-anchoring design. The self-anchoring design has series of V-shaped slits 85 (preferably identical in size and shape) arranged along the central axis of the implant member 1. These V-shaped slits 85 are cut in each arm 83*a*, 83*b* of the implant member 1 and point towards the center support section 81 of the implant member 1.

Unlike systems which rely on statically-formed geometry, such as the saw-tooth edges 87 discussed above, to create the self-anchoring force, this configuration incorporates a dynamic self-anchoring system which develops a progressively-increasing anchoring ability that provides greater resistance to movement the more the implant member 1 is stressed. By using a soft, natural tissue material, the implant member 1 can deform easily when subjected to the stress and tension encountered during implantation. As tension is applied, the implant member 1 stretches and buckles causing expansion and opening of the slits 85 to allow the surrounding patient tissue to compress inward through the implant member 1. As the applied tension increases, the slits 85 begin to deflect outward to create a progressively greater anchoring force. The greater the deflection, the greater the surface area contacting the patient's tissue, and the better the anchoring force. If, however, an excessive amount of stress or tension is applied, the slits 85 buckle inward allowing the implant member 1 to slide gradually through the patient's tissue. This helps minimize the possibility that too much anchoring force will be generated by the implant member 1.

This self-regulated anchoring design creates the dynamic ability to provide a progressive anchoring force for the implant member 1. The static geometry-based systems cannot develop this progressive anchoring ability because the self-anchoring features are fixed in a single, static position. As a result, their functionality and ability to self-adjust to the tension being applied is limited.

As an added benefit of the centralized self-anchoring design, all edge texturing can be eliminated, leaving smooth, straight edges on the implant member 1. This may be helpful because edge texturing can create additional drag during implantation (i.e. a higher implantation force is required) which could cause additional trauma to the surrounding tissue. By centrally locating the self-anchoring mechanism on the implant member 1, there is almost no drag generated by the slits 85. The anchoring force is only generated when the direction of tension on the implant member 1 is reversed, exactly as is desired during clinical use of the implant member 1 as a sling.

With reference to FIGS. 17A and 20A-E, it should be noted that the V-shaped slits 85 on one side of the implant member 1 face in the opposite direction from the slits 85 on the other side of the implant member 1. This is done because the implant member 1 is introduced in the patient's body one arm at a time, with each arm 83*a*, 83*b* being drawn upward from beneath the area of the patient's urethra into the suprapubic space toward the abdomen. Thus, it is the direction in which each arm 83*a*, 83*b* of the implant member 1 advances into the body during placement that determines slit orientation.

In contrast to the foregoing implant member configuration, an implant member 1 having outer sawtooth-shaped edges 87, as shown in FIG. 12 will be more difficult to position, because the sawtooth-shaped outer edges 87 of the implant member 1 will tend to resist any movement, whether forward or backward. To some extent, this resistance to movement can be controlled by altering the shape of the sawtoothed outer edges 87—by suitably tapering the teeth 95 so that, moving from the proximal end of the tooth 95 to the distal end of the tooth 95, the tooth 95 narrows inward, resistance to rearward movement can be increased and resistance to forward movement can be decreased.

Further, as shown in FIGS. 15A, 15C, 17A-D, 18A-B, 19A-E, 20A-E; 22A-F and 24A-C, internal slits 85 or perforations could be provided in at least some portion of the implant members arms 83a, 83b to allow the patient's tissue to fold into the interstitial spaces formed by those slits 85 or perforations. This arrangement also facilitate tissue ingrowth, and increase strip flexibility, much like synthetic mesh.

Alternate designs for the dynamic, self-anchoring slits 85 can be envisioned. In these other designs, the shape of the slits 85 is altered, for example, with an arrow design (essentially a V having a bisecting slit in the middle of the V), a semicircular slit design, a rectangular slit, etc. all could be used. Some of these other configurations will later be discussed in detail.

By way of non-limiting example, the internal slits 85 could be V-shaped, arrow-shaped, curved, round, oval, square, triangular or irregular, and they could be arranged in a straight line, as depicted in FIGS. 19A-E and 22C-E, or in patterns such as rows, checkerboards, diagonal lines, or even randomly, as shown in FIGS. 24A-C and 26A. A range of different size and pattern slits or perforations 85 could be used in a single implant member 1, and the internal perforations also could be combined with various edge details, or could be used alone to vary the anchoring properties of the implant member 1.

Figure 17A:
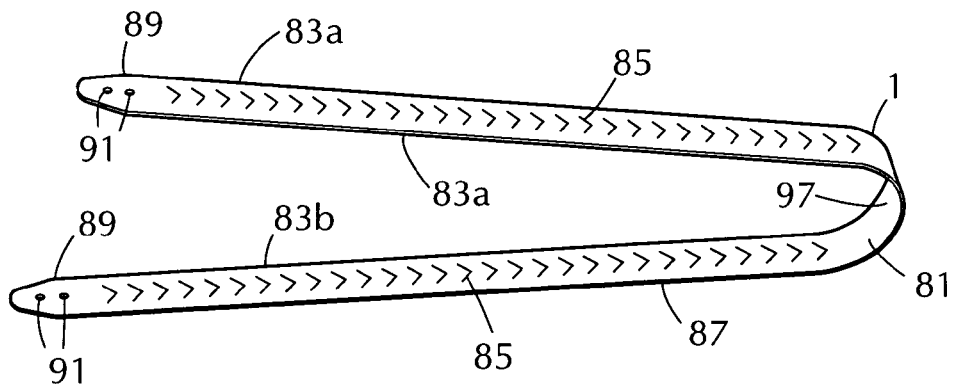
FIGS. 17A-D are views depicting various implant members in accordance with the present invention.
Figure 17B:
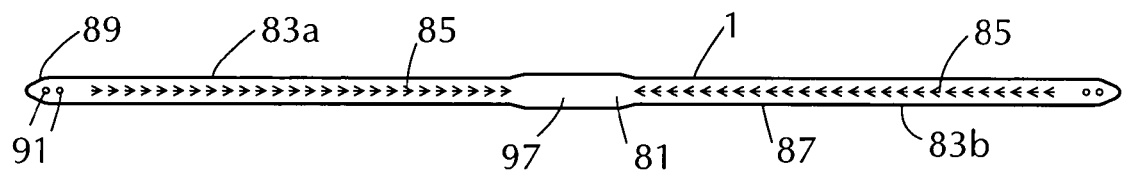
Figure 17C:
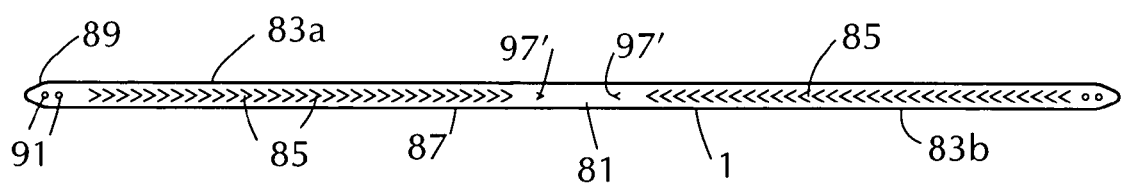
Figure 17D:
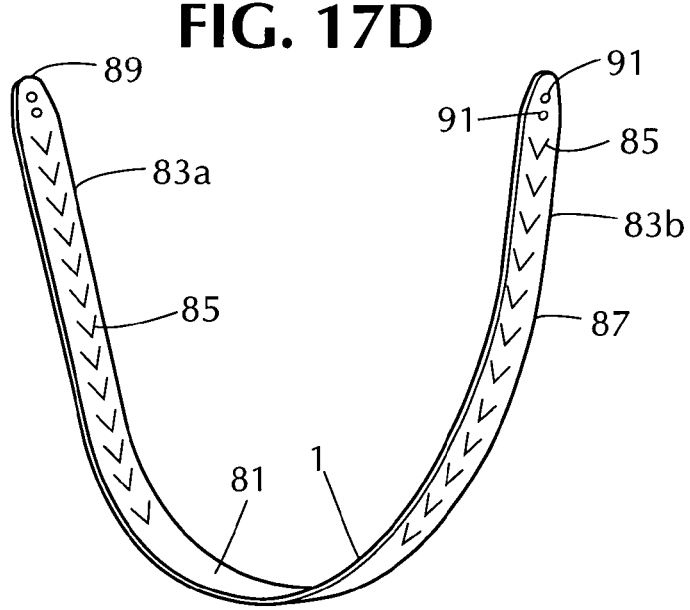

Different arrangements of slits 85 could be combined with different implant member shapes. The middle urethral support section 81 can either be straight-edged tissue without holes, or it can be continuously textured over the full length of the implant member 1. In addition, the middle urethral support section 81 could be wider than the textured arms 83a, 83b of the implant member 1 to provide a larger support area under the urethra. The present most preferred option is a straight-edged, uniform width, non-textured support section 81 to help alleviate any concerns over erosion from the texturing details. In the middle of the urethral support 81, a small hole 97, visible in FIGS. 17A, 17B, 20A and 20C-E, or notches on the edges (not shown) could be provided to help identify the center of the implant member 1 for even positioning under the urethra. As shown in FIG. 17C, inwardly-pointing triangles 97' also could be used to define the center part of the implant member 1. Alternatively, a dye mark (not shown) could be made across the center.

Figure 20A:
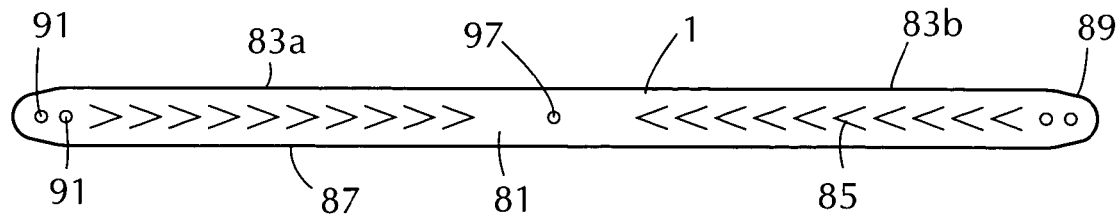
FIGS. 20A-E are views showing the configurations of different implant members in accordance with this invention.

For example, FIG. 20A shows an implant member 1 of uniform width having V-shaped slits 85 disposed along its centerline that is presently preferred. A center region 81 of the implant member 1 does not have such slits, however, so that it can better support the patient's tissue. Also, this embodiment has a hole 97 formed at its center in order to help the surgeon determine when the implant member 1 has been properly positioned. Each arm 83a, 83b has two openings 91 formed at its tip 89, and these openings 91 receive the projections 157 of a connector 107 such as that shown in FIG. 9D. This arrangement also could be used with a connector 7 having a single projection 57 on each side, as shown in FIG. 8A. Alternatively, these holes could be omitted and they could be formed by the surgeon using a blade or scissor, or the could even be formed when the connector arms 53a, 53b, 55a, 55b are closed together, the projections 57 serving as punches.

Figure 20B:
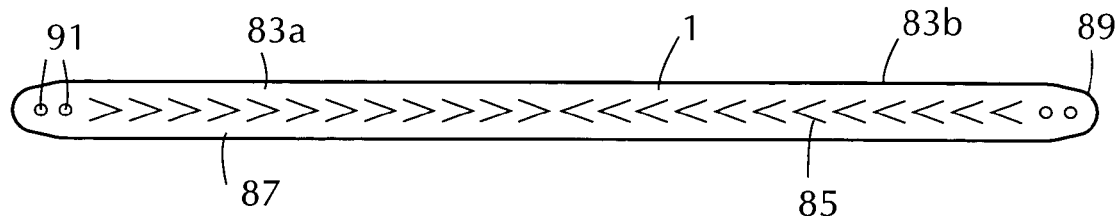

In contrast, the implant member 1 depicted in FIG. 20B has slits 85 along its entire length—here, the surgeon can identify the center of the implant member 1 by looking for the region where the V-shaped slits 85 change their orientation. This configuration may allow for greater variation in the placement of the implant member 1 in the patient's body.

Figure 20C:
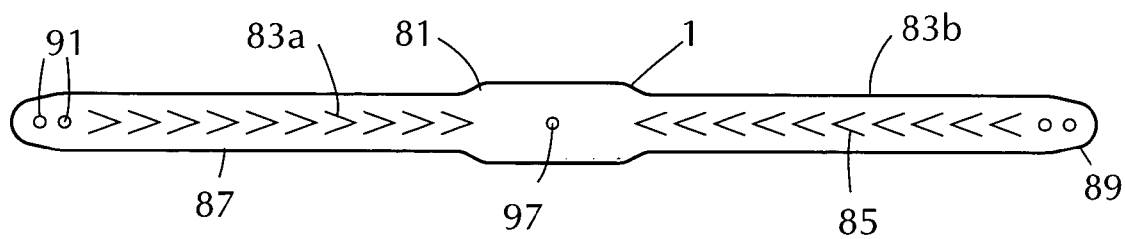

The implant member 1 shown in FIG. 20C is generally similar to that depicted in FIG. 20A, differing in that the central section 81 of the implant member 1 is wider than the arms 83a. 83b. Again, the central section 81 is solid, save for a central opening 97 that helps in determining when the implant member 1 is properly placed. The wider center section 81 provides additional support for the patient's urethra.

Figure 20D:
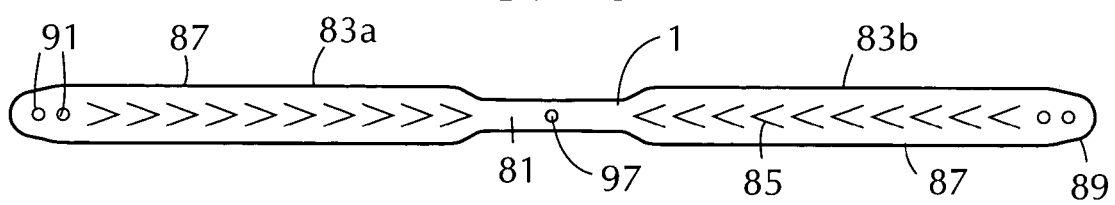

The implant member 1 shown in FIG. 20D has a solid center section 81 with a central positioning opening 97 and arms 83a, 83b that are wider than the central section 81.

Figure 20E:
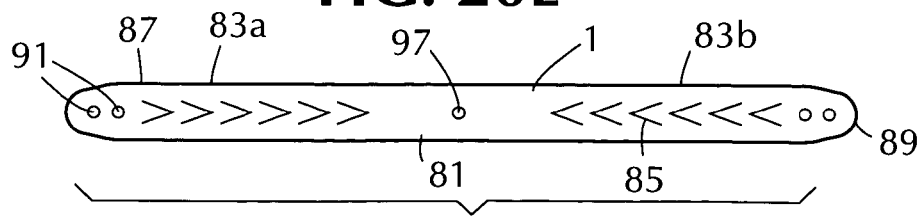

The implant member 1 depicted in FIG. 20E is similar to that shown in FIG. 20A, but the arms 83a, 83b are shorter in length. The shorter arms 83a, 83b anchor primarily in the endopelvic fascia. An implant of this length also could be implanted without the need for an abdominal incision. Also, this implant member 1 could be used with extensions attached to the tips 89 of the arms 83a, 83b, as will be discussed later in this description.

With reference now to FIGS. 18A-B, the V-shaped slits 85 formed in the implant member 1 allow easy implantation of the implant member 1 in the forward direction, and the implant member 1 has a lower resistance to pull-through than a strip having sawtooth-shaped edges. FIG. 18A shows the implant member 1 in the free state, without any tension applied thereto. The slits 85 are closed and, when seen from the side, the implant member 1 is flat. However, as shown in FIG. 18B, when tension is applied along the length of the implant member 1, the slits 85 open so that portions of the implant material extend outward from the plane of the implant member 1.

Figures 21A, 21B:
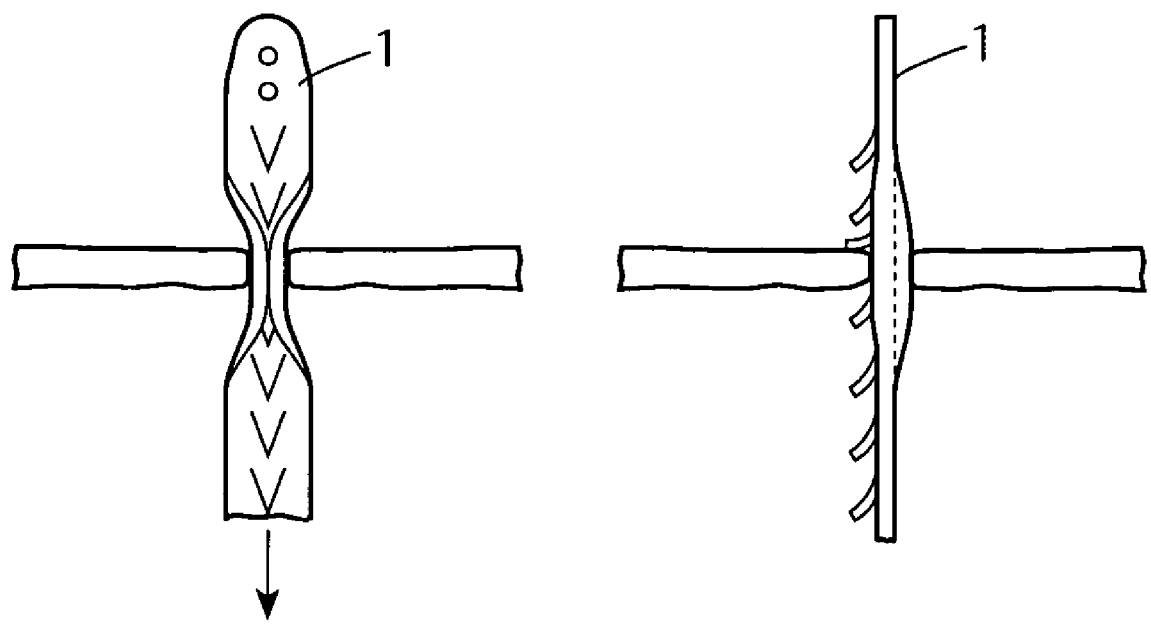
FIG. 21A is a front view and FIG. 21B is a side view showing how an implant member in accordance with this invention deforms as it passes through a layer of tissue.

With reference now to FIGS. 21A and 21B, the lateral edges 87 of the slits 85 press against the surrounding fascia and tissue, providing a secure anchorage from which to suspend the implant member 1. When seen in the front view of FIG. 21A, the implant member 1 is substantially curved and compressed at the position where it passes through the tissue. However, the portions above and below the tissue through which the implant member 1 passes are uncompressed, and the tension applied to the implant member 1 causes the slit regions to open up. The portions of the implant member 1 defined by the slits bend outward and, as seen in FIG. 21B, interfere with the tissue and increase the implant member's resistance to backward movement.

Figure 26A:
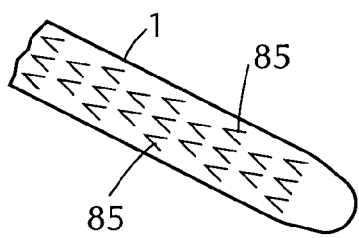
Figure 26B:
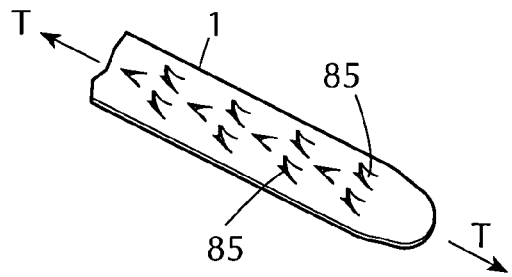

A similar design that is easy to pull forward but which resists rearward movement is depicted in FIGS. 26A-B. In this embodiment, the implant member 1 has a pattern of V-shaped slits 85 formed on its surface not in a line, but rather, over substantially the entire area of the implant member's arm 83. When in the untensioned state shown in FIG. 26A, the slit portions lie flat. However, when tension T is applied to the implant member 1, as can occur during implantation or thereafter if there is an abdominal pressure increase, and as shown in FIG. 26B, portions of the implant member 1 project outward and will help to anchor the implant member 1 in the patient's tissue.

FIGS. 26C-E show other embodiments of an implant member 1 similar to that shown in FIGS. 26A-B, differing with regard to the shape and arrangement of the slits 85. It should be noted that the implant member 1 shown in FIG. 26C has a line of triangular internal openings 86, as well as two adjacent lines of V-shaped slits 85.

Figure 22B:
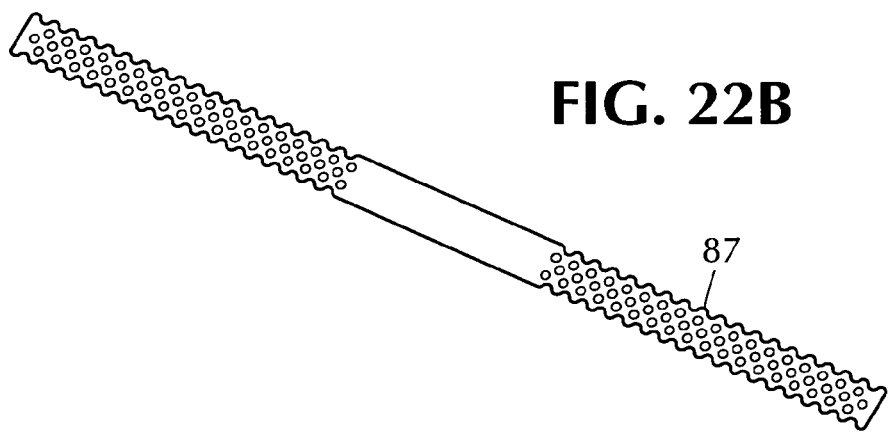
Figure 22C:
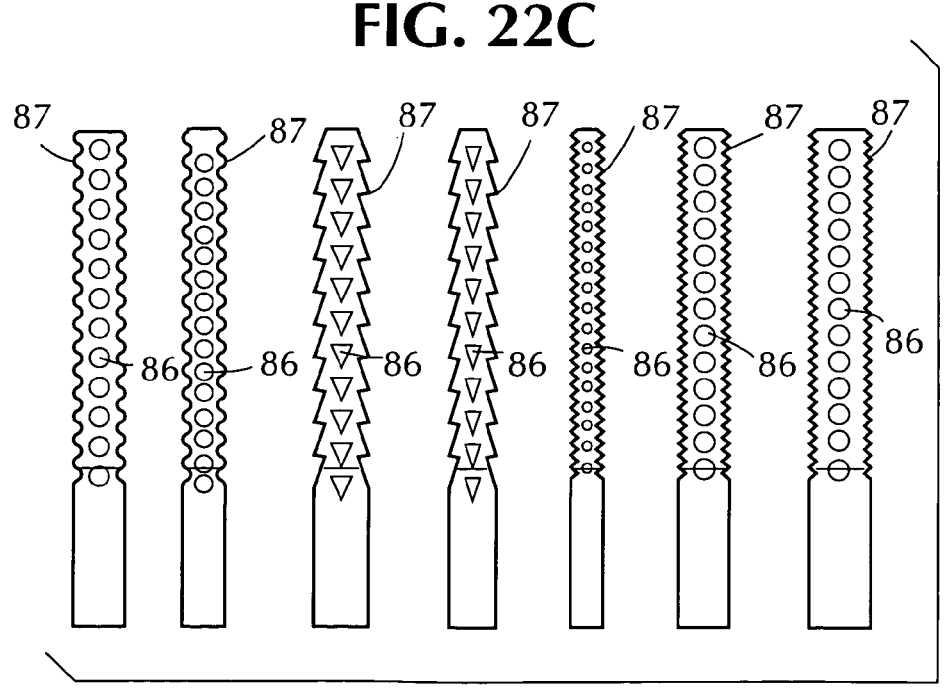
Figure 22D:
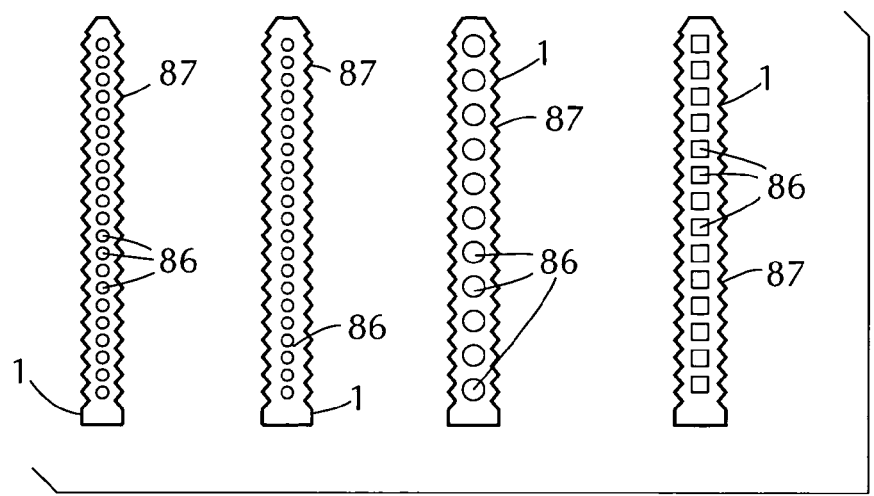
Figure 22E:
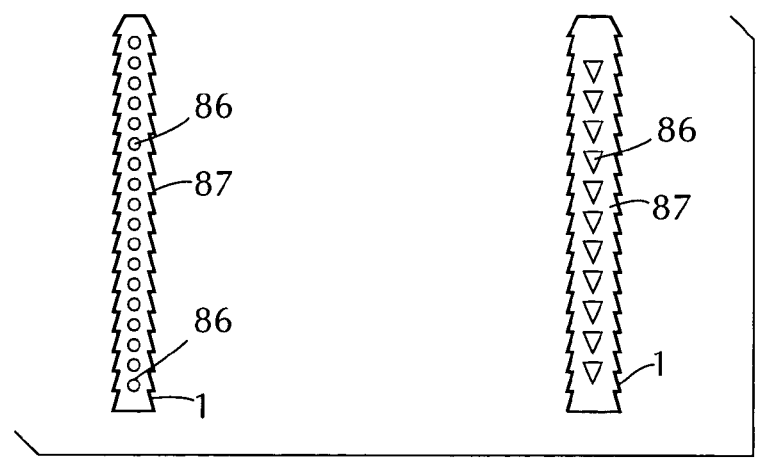
Figure 22F:
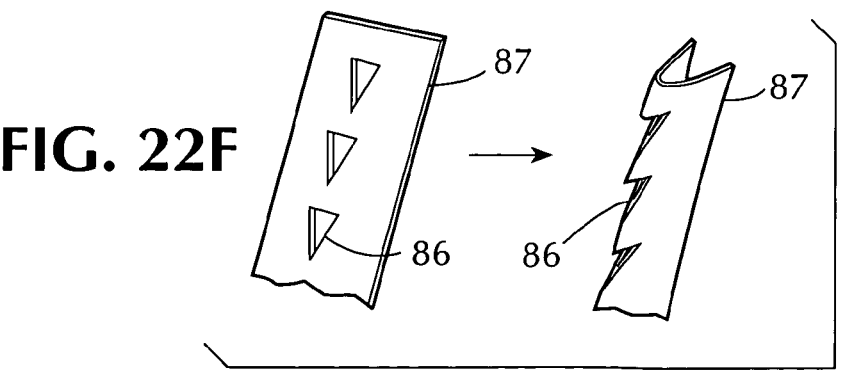
Figure 24A:
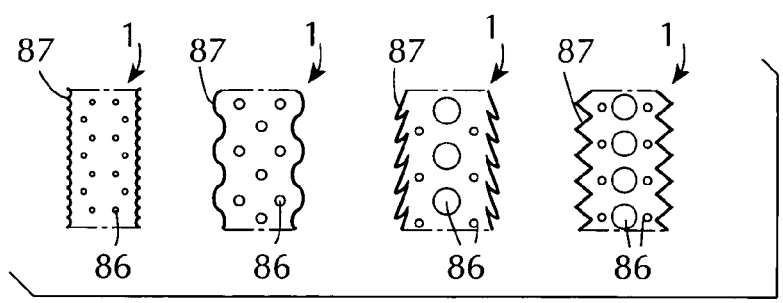
FIGS. 24A-C are views showing alternative implant member arrangements in accordance with this invention.
Figure 24B:
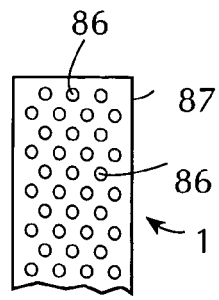
Figure 24C:
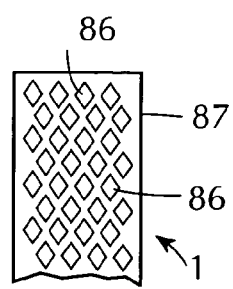

FIGS. 22B-F and 24A-C show implant members 1 having internal openings 86. As shown in FIGS. 22C-F, these openings 86 can be circular, triangular or rectangular, or even irregular (not shown). The openings 86 shown in FIGS. 22C-F are arranged along a line parallel to the center axis of the implant member 1, while the openings 86 shown in FIGS. 22B, 24A and 24C are arranged over substantially the entire width of the implant member 1. While the implant members 1 shown in FIGS. 22B-E and 24A have irregularly shaped outer edges 87, and the implant members 1 shown in FIGS. 22F, 24B and 24C have straight outer edges 87, it will be understood that the different opening shapes and arrangements can be used with either straight or irregular outer edges 87 as is desired. In other words, and by way of nonlimiting example, the implant members 1 shown in FIG. 22C could be produced with straight outer edges 87, and the implant members 1 shown in FIGS. 24B and C could be produced with sawtooth shaped outer edges 87.

It should be understood that although the designs depicted in FIGS. 17A-D, 18A-B, 19A-E and 20A-E all have a single row of slits 85, this invention is not to be limited to that arrangement. Multiple rows of slits 85, random arrangements of slits 85, and a combination of rows of slits 87 and a random arrangement of slits 85 all could be employed without departing from the present invention.

Figure 23A:
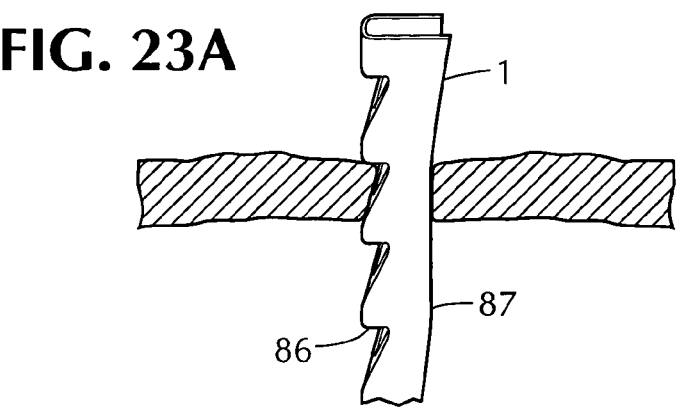
FIGS. 23A and 23B are perspective views showing changes in shape of an implant member as it passes through a layer of tissue.
Figure 23B:
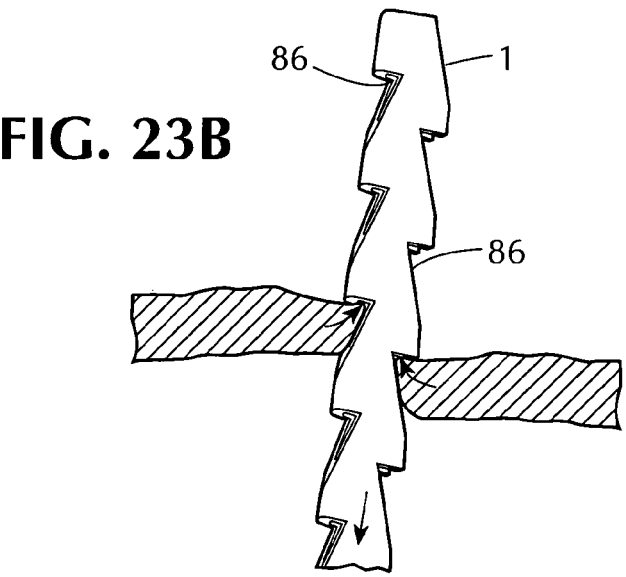

In a design having centerline openings 86 disposed along the length of the implant member 1, such as the design depicted in FIGS. 23A-B, the tissue will tend to fold over on itself during implantation, creating multiple ridges at the centerline of the implant member 1, helping to anchor the implant member 1 in the patient's tissue. Owing to the geometry of the openings 86 openings in this embodiment, the implant member 1 can easily advance into the patient's tissue, but when in place "locks" and resists rearward tension.

Different opening shapes also could be combined; as depicted in FIG. 26C, the implant member 1 could have both triangular openings 86 arranged along its centerline, along with triangular surface slits 85 arranged laterally to the centerline openings 86, and smooth edges 87 for smooth and easy implantation. The triangular openings 86 and triangular slits 85 operate in the manner already discussed to resist rearward tension.

Figure 25A:
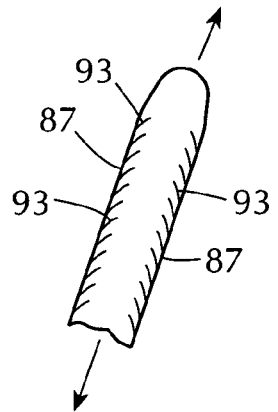
FIGS. 25A-C are views showing how an implant member with straight but slitted edges can be secured in tissue.
Figure 25B:
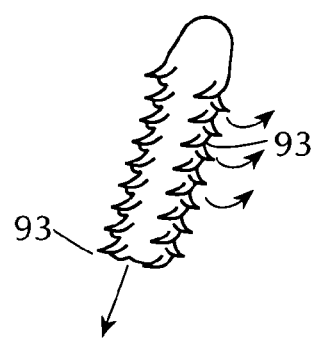
Figure 25C:
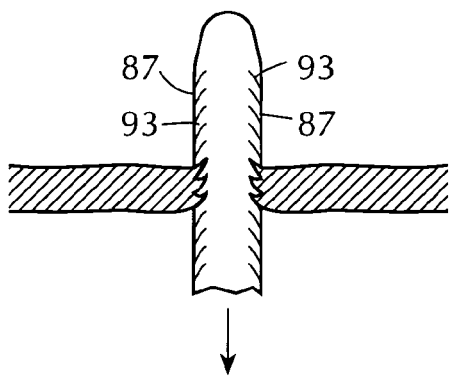

Also by way of non-limiting example, an embodiment of an implant member 1 having straight edges 87, yet having improved anchoring properties, is shown in FIGS. 25A-C. As depicted therein, the implant member 1 has a series of angled, inward-extending slits 93 arranged preferably on both of the implant member's edges 87 (it will be appreciated that only one side of the implant member could be provided with such slits 93). With reference to FIG. 25A, when tension is not applied to the implant member 1, the edges 87 of the implant member 1 lie flat. However, as seen in FIGS. 25B and 25C, when the implant member 1 passes through the patient's tissue and tension is applied to the implant member 1, the edges 87 of the implant member 1 having slits 93 deform and flare outward and "lock" into the tissue, resisting the tension being applied. The implant member 1 "locks" into the surrounding tissue because the slits 93 allow portions of the implant member 1 to fold out from the member's main body. As depicted in FIG. 25C, the portions that fold out extend into the patient's tissue, resisting backward force. This increases the implant member's resistance to backward movement.

As a further option, implant member 1 could have one or more openings 86 formed in arm portions 83a, 83b. By way of non-limiting example, such openings 86 could be of geometric shape (i.e., round, square, triangular), or irregular, and could be arranged in a line, in a pattern, or irregularly. Embodiments of such implant members are depicted in FIGS. 22B-F and 24A-C. During implantation, the openings 86 do not interfere with insertion of the strip It will be appreciated that more than one opening shape could be used on a single implant member 1, and that opening size and pattern could be varied to change the strip's ability to resist backward tension. As discussed earlier with regard to different slit arrangements, this invention is not to be limited to the configurations shown in the drawings. Multiple rows of openings, random arrangements of openings, and a combination of rows of openings and a random arrangement of openings all could be employed without departing from the present invention, for example, as shown in FIGS. 24A-C.

By way of non-limiting example, the openings 86 in the implant member 1 shown in FIG. 24B could range in size from 0.25-3.0 mm.

The foregoing embodiments of this invention employ implant members each made from a single piece of material. This invention also envisions composite implant members that are assembled from several different pieces of material.

Figure 28C:
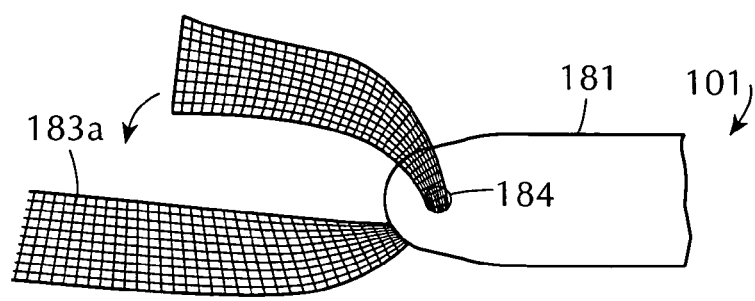
Figure 28D:
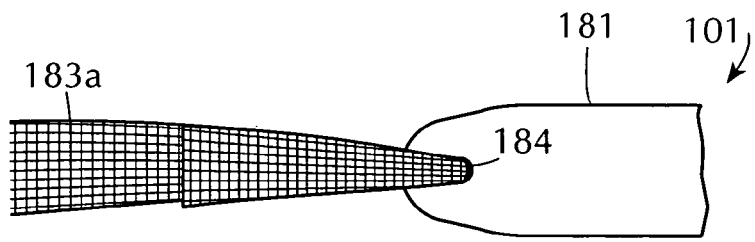
Figure 28E:
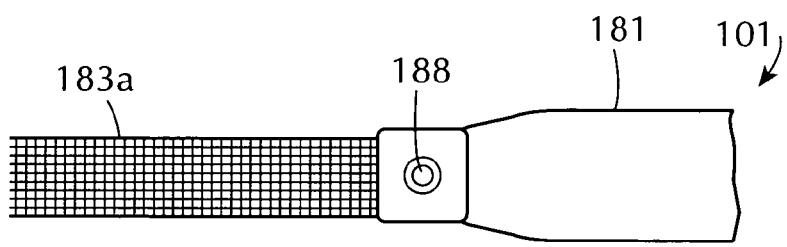
Figure 28F:
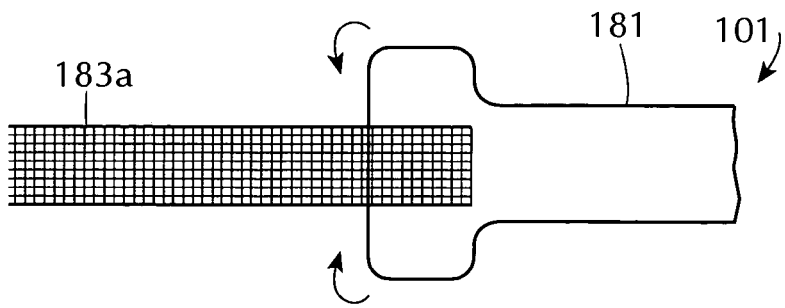
Figure 28G:
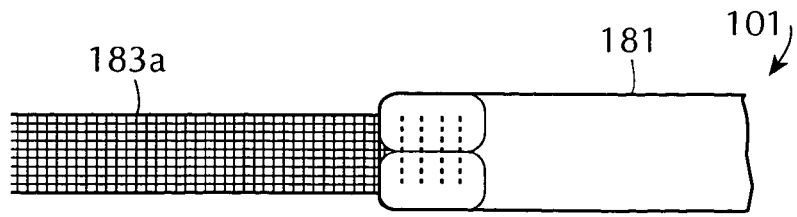

FIGS. 27-28G depict a range of different composite implant members 101. Such implant members 101 can have a center section 181 made from one type of material, such as natural material, and arms 183a, 183b made of a different material, such as synthetic mesh, as shown in FIGS. 27-28G. Among the benefits of this arrangement is the ability to construct each of these sections using material which has the requisite properties desired for the section where is used; the mesh arms 183a, 183b can be self-anchoring, and the central natural material 181, if positioned under the urethra, reduces the potential for erosion and infection.

The arms 183a, 183b can be attached to the center section 181 using any suitable technique now known or hereafter discovered. By way of non-limiting example, FIGS. 27, 28C and 28D show mesh arms 183a, 183b passing through slits 184 formed at the ends of the center section 181 and doubling back over the body of the mesh arms 183a, 183b. The tip of the doubled section is then fastened to the body of the mesh section 183a, 183b by any suitable attachment technique, such as suturing, heat-bonding, ultrasonic welding, adhesive, stapling or riveting.

As depicted in FIGS. 28B and 28E, the mesh arm 183a, 183b can be joined to the natural center section 181 using a rivet or snap-down connector 188.

FIGS. 28F and 28G show still another embodiment, wherein the end of the natural material center section 181 is "T" shaped, the mesh arm 183a or 183b is placed onto the cross-arm of the T, and the cross-arm of the "T" is folded back over the mesh arm 183a, 183b, and is then secured, for example, by suturing or adhesive.

While the foregoing implant member configurations are suitable for connection to the introducer needle 3 by a separate connector 7, the present invention also contemplates that the implant members 1 could be constructed with a suitable integral connector 407 for attachment to the introducer needle. Such an implant member design allows the surgeon to complete the implantation procedure more rapidly, since there is no need for the surgeon to join the implant member to the connector.

Such a connector 407 can be thought of as a "half" connector, since it already is joined to the implant member 1 and only needs to be attached to the introducer needle 3.

One example of an implant member 401 having integral connectors 407 attached to the ends of the implant member

Figure 39:
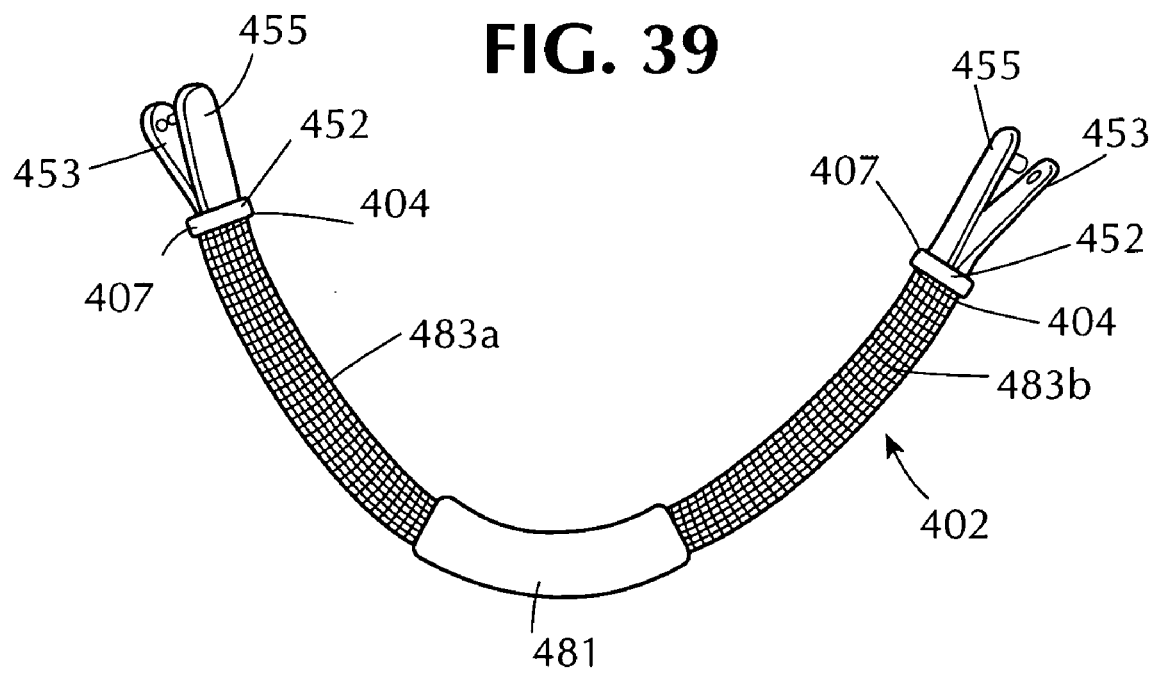
FIG. 39 is a perspective view showing another embodiment of an implant member used with connectors.

401 is shown in FIG. 39. As shown, the ends 404 of the arm sections 483a, 483b have connectors 407 respectively attached thereto. These connectors 407 serve to join the implant member 401 to a needle (not shown), which is used to position the implant member 401 in the patient's body, as has already been discussed. This arrangement, it should be noted, is a composite, in which the central portion 481 of the implant member 401 is made of one material, such as biocompatible natural material, and the arms 483a, 483b, to which the half-connectors 407 are joined, are made of a different material, such as synthetic mesh material.

Connectors 407 are generally similar in configuration and operation to connectors 7, 107, 207 and 307 discussed above. They differ, however, in that whereas the connectors 7, 107, 207 and 307 are double-ended, connectors 407 are single-ended. Thus, connectors 407 are jaw-like in appearance. A projection 452 at the base of the jaws 453, 455 is provided for attachment to the arms 483a, 483b of the implant member 401. The projection 452 can be attached to the arms 483a, 483b using any suitable technique now known or later discovered. By way of non-limiting example, thermal bonding could be employed.

Also by way of non-limiting example, the projection 452 could be made from two shorter jaws (not shown) having a suitable locking mechanism, such as an interfering flanged projection in one jaw and a mating opening in the other jaw, and which can be squeezed together with the arms 483a, 483b therebetween to securely join the implant member 401 to the projection 452.

The composite implant member 401 discussed above preferably has a middle urethral support section 481 that is about 7-8 cm long. This size is, however, mentioned only by way of example, and not limitation.

A number of other implant member configurations having integral connectors will now be discussed.

Figure 40:
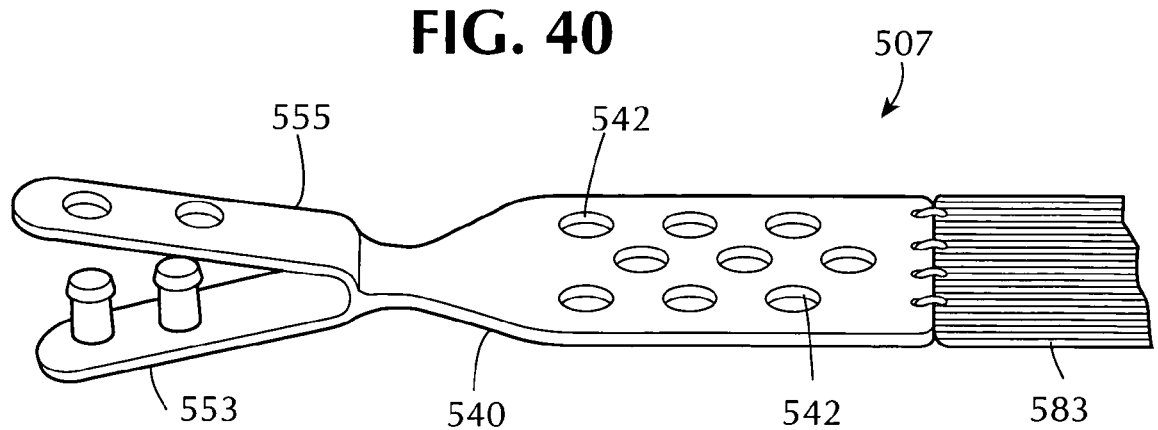
FIGS. 40 and 41 are perspective views showing two different types of connectors.

As shown in FIG. 40, an elongated connector 507 with an integral strap 540 is depicted. This connector 507 has lower and upper arms 553 and 555 which are substantially similar in form and function to the connector arms 253a, 253b, 255a, 255b shown in FIGS. 9A-C. These arms 553, 555 are integrally attached to one end of the flat strap/connector body 540 having a plurality of holes 542 running therethrough (alternatively, the holes 542 could be omitted). The other end of the connector body 540 is permanently attached to the arm portion 583 of the implant member 501 (in practice, a connector 507 will be attached to each of the two ends of the implant member 1). As shown in FIG. 40, this connection is made by suturing, but this invention is not to be limited to that arrangement. Any other suitable attachment technique, whether now known or hereafter discovered, could be used, such as, for example, adhesive bonding, ultrasonic welding, or mechanical interconnection using a fastener such as a rivet. This connector 507 could be made by any suitable manufacturing technique, such as molding.

Once the implant member 501 to which connector 507 is attached has been properly positioned, the exposed portion of the connector protruding above the patient's abdomen is removed by cutting the connector body where it is exposed. This way, all of the implant member 501, and a portion of the connector 507, the holes 542 of which also contribute to the anchoring function, remain in the body. If a very long implant member 501 is used, it is conceivable the arms 583a, 583b of the connector will be exposed and so would have to be cut to detach the connector, although this would be less desirable insofar as implant material would be wasted.

Figure 41:
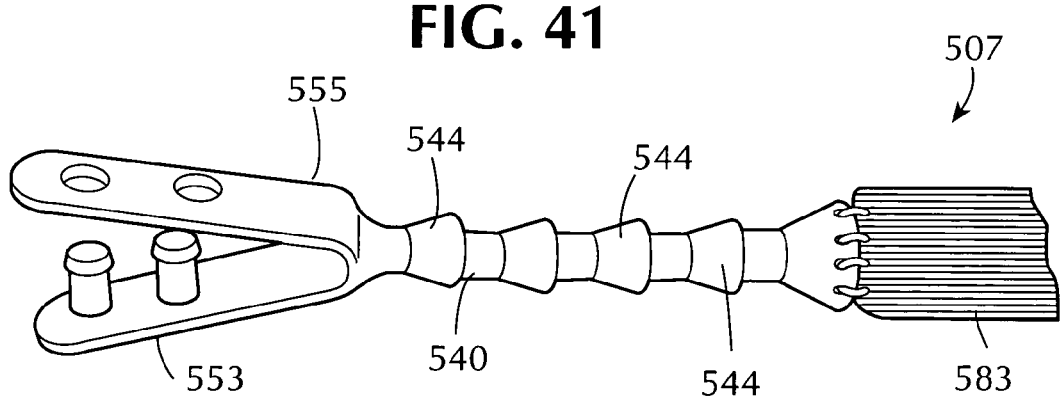

FIG. 41 depicts still another example of an elongated connector. Like the embodiment shown in FIG. 40, this connector 507 also has lower and upper arms 553, 555. Such a connector 507 could be formed in any suitable manner, such as by molding. These arms 553, 555 are integrally attached to a generally cylindrical connector body 540 having a plurality of spherical or conical enlargements 544 disposed along its length (other shapes also could be used). The precise shape and number of enlarged regions 544 is not to be limited, and, if desired, the enlarged regions 544 could be omitted altogether. The other end of the connector body 540 is enlarged and is permanently attached to the end of the arms 583 of the implant member 501. Again, this connection is shown as being made by suturing. Any other suitable attachment technique could be used, including the techniques just described above.

Again, once implant member 501 is properly positioned in the body, the exposed portion of the connector protruding above the patient's abdomen is removed by cutting the connector body where it is exposed. All of the implant member 501, and a portion of the connector 507, the holes 542 of which also contribute to the anchoring function, remain in the body. As already noted, if a very long implant member 501 is used, it is conceivable the arms 583a, 583b of the connector will be exposed and so would have to be cut to detach the connector, although this would be less desirable insofar as implant material would be wasted.

An alternate embodiment of an implant member 201 according to this invention will now be discussed in connection with FIGS. 29-38. The implant member 201 is intended to handle more easily than other implant members, while still applying the required force to the body tissue being supported. As will now be explained in detail, this implant member 201 is preferably made of natural material, and is processed to improve the material's physical properties.

Among the materials which can serve as supports in female urinary incontinence sling suspension procedures is acellular porcine dermal tissue. Such dermal tissue material must, however, be processed to render it biocompatible. One scheme for preparing biocompatible porcine dermal tissue is set forth in U.S. Pat. No. 5,397,353 to Oliver et al. and owned by Tissue Science Laboratories plc. Such material is commercially available as Pelvicol™ implant material, distributed by C.R. Bard, Inc. of Murray Hill, N.J. and produced by Tissue Science Laboratories PLC, of Aldershot, Hampshire, United Kingdom.

The material described in the '353 patent is particularly preferable for use in the present invention because such material is non-antigenic and is recolonized and revascularized by the host tissue. Also, this material, owing to cross-linking, is non-resorbable, meaning it is not processed and eventually absorbed by the patient's body. Consequently, a support made from this material will provide permanent support, and in contrast to a procedure using a support made from resorbable material, the patient will not have to undergo later surgery to replace the support. It should be understood that other types of natural materials also could be used.

Advantageously, Pelvicol™ implant material has omnidirectional strength properties. Further, Pelvicol™ implant material does not shed particles under load, as mesh material does. In this invention, the Pelvicol™ implant material is specifically designed to provide for optimum anchoring and adjustability in the rectus fascia at the abdomen and/or the endopelvic fascia near the urethra. These two tissue layers provide the majority of the anchoring force around the implant by virtue of the dense fibrous nature of the fascia. Based on simulated use testing, the Pelvicol™ implant material creates an anchoring force that is comparable to and, in some cases, even better than that generated by pure synthetic mesh implanted in the fascia.

Figure 29:
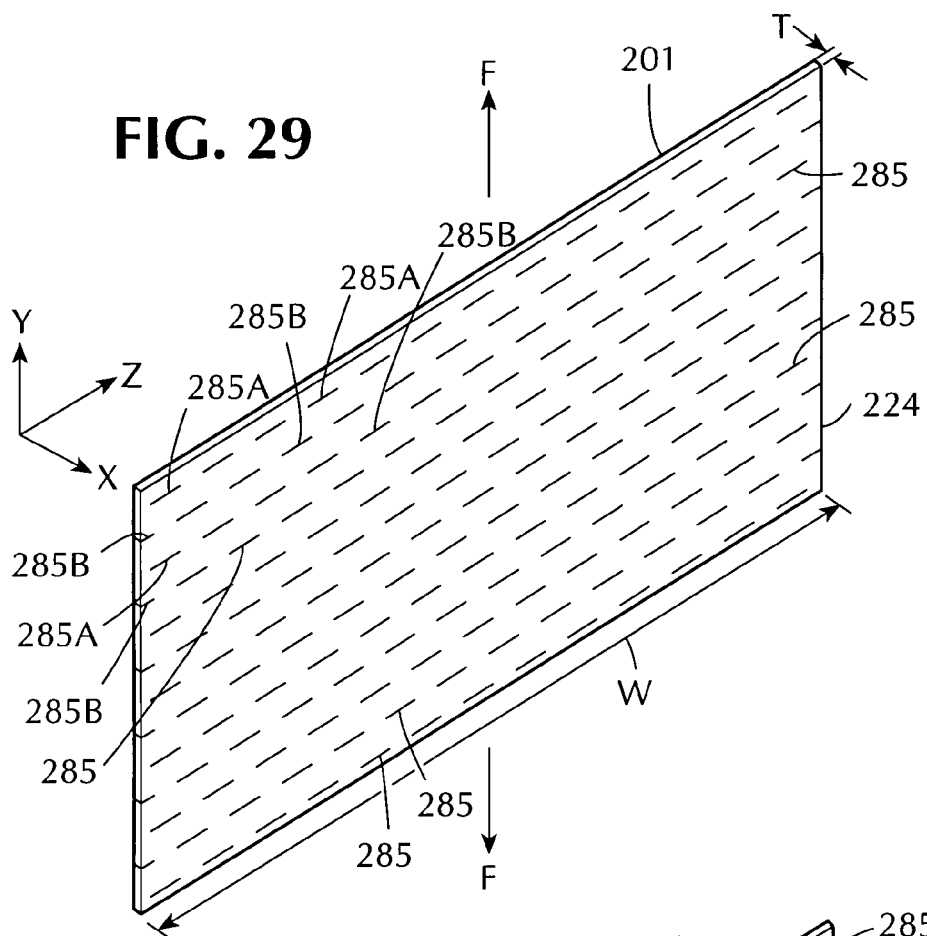
FIG. 29 is a close-up perspective view of a portion of a slitted support member prepared in accordance with this invention and which is in the relaxed (unexpanded) state.
Figure 30:
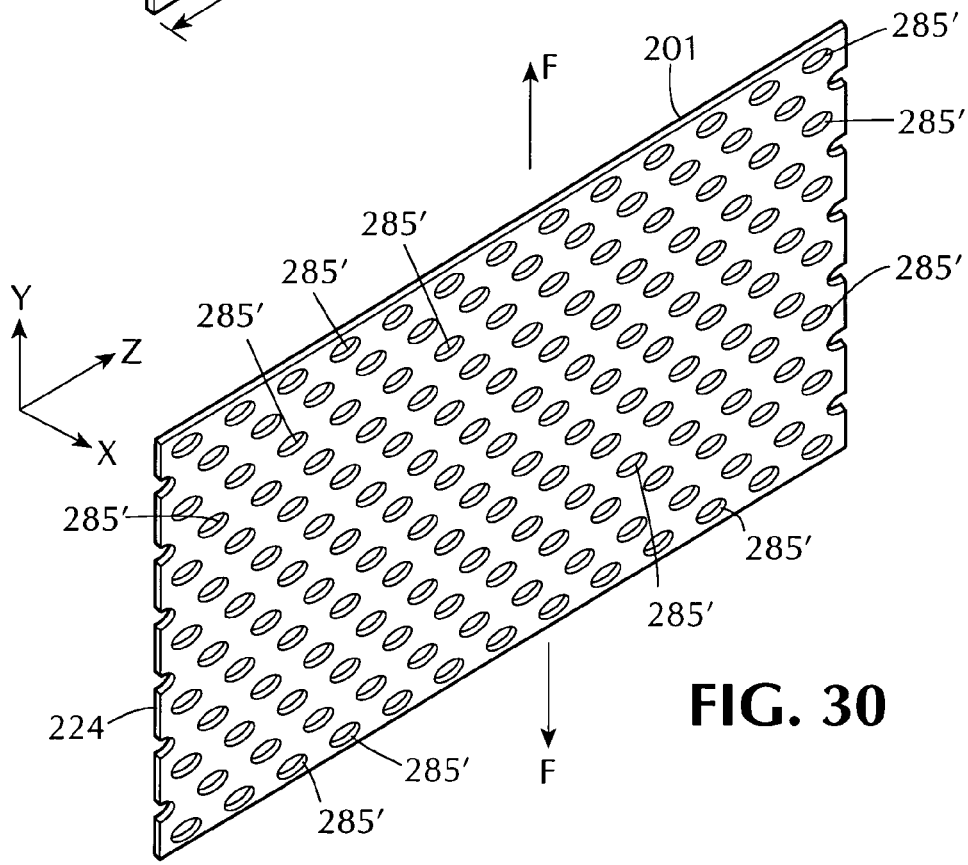
FIG. 30 is a close-up perspective view of portion of the slitted support member of FIG. 29 under tension, in the expanded state.

FIGS. 29 and 30 show in close-up how a slitted piece of processed dermal tissue 224 can expand in response to applied force.

As depicted in FIG. 29, implant member 201, which is incorporated into a suitably-shaped sling, as discussed below, includes a number of slits 285 formed therein. Implant member 201 can be a flat piece of acellular dermal tissue 224, preferably, porcine, prepared in accordance with the '353 patent. Because no tension is being applied to implant member 201, slits 285 remain closed due to the inherent elasticity of the material from which implant member 201 is made.

Implant member 201 has a length (not shown in full in FIGS. 29 and 30) running in the direction of axis Y, a width W extending in the direction of axis Z, and thickness T in the direction of axis X.

The thickness T is of interest because it affects how the material "handles"; a thin piece of material will be more supple than a thicker piece of material, and so the thin piece of material can better conform to the patient's anatomy. A thin piece of material may not, however, be able to support all loads applied. This means that the thickness of the material should be selected so that the material is sufficiently flexible, yet is also strong enough to support all forces that it may be subjected to.

By way of non-limiting example, the preferred thickness T is about 0.8-2.0 mm; thinner material can be used but, depending upon the load applied, may deform excessively or even fail. Consequently, material thinner than about 0.8 mm preferably will not be used in most circumstances. Thicker material also can be used, although it should be understood that material greater than 2.0 mm may be too thick because it might be noticeable to the patient, and also might be so stiff that it is difficult for the surgeon to work with. Here, material thicker than about 2.0 mm preferably will not be used in most circumstances.

The implant member 201 is preferably between 0.5-3 cm. in width (W), and, more preferably, between 1-2 cm. in width. When choosing the width of the implant member 201, the patient's body size and the amount of force likely to be required can be taken into account. Higher force levels may require the use of a wider or thicker implant member 201.

The implant member 201 extends in length along the direction of axis Y. Preferably, the implant member 201 is between 20-40 cm., more preferably, between 30-40 cm., and even more preferably, 30 cm long when in the tension-free state.

It also will be appreciated that the implant member 201 could be trimmed as needed, whether because of the patient's anatomy or because less than the full amount of the implant member material is needed.

With continued reference to FIG. 29, the slits 285 formed in the implant member 201 are preferably arranged in a regular and repeating pattern. By way of non-limiting example, the slits 285 can be about 3.7 mm in length. As can be seen, the slits 285 in the implant member 201 are formed in rows that run in the direction of axis Z and which rows are parallel to the length of the implant member 201. Slits 285 are arranged in a "row" where those slits 285 are all line segments which lie on a single line. The slits 285 are preferably arranged in a staggered fashion; as shown in FIG. 29, alternating rows of slits 285A and 285B are placed so that, moving in the direction of axis Y along the length of the implant member 201, the slits in rows 285A do not lie directly adjacent to and in registry with the slits in rows 285B. Instead, moving along axis Y from a slit 285 in any given row 285A one then encounters the solid material between the slits 285 in the adjoining row 285B and then the slit 285 in the next row 285A that follows the row 285B. The slits 285 can be arranged so that the slits 285 in alternating (rather than adjacent) rows are disposed in registry. Staggered also can be construed more broadly to mean that the rows of slits 285 are arranged in any manner such that a slit 285 in one row does not lie alongside and in complete registry with a slit 285 in an adjacent row, meaning partial overlap of slits 285 is permitted.

Optionally, the ends 289 of the implant member 201 could be rounded for easier implantation.

The arrangement and quantity of slits 285 will affect the properties of the implant member 201. As the number and/or length of the slits 285 increases, the implant member 201 will stretch more under a given load. An implant member 201 having a large number of slits 285 will be more pliable than an otherwise identical implant member having a lower number of slits, but the former implant member 201 may not be as strong because of the greater number of slits 285.

So too, slit size can be varied to control the elastic properties of the implant member 201. As larger slits 285 are formed, the implant member 201 will stretch more under a given load, and will not be able to withstand as large a maximum load before failing.

This configuration provides the anchoring benefits which can be obtained when synthetic mesh is used, without the possibility of tissue abrasion, which can occur with synthetic mesh.

The slits 285 can be formed in the source material 224 using a skin graft mesher (not shown). Skin graft meshers are known and are currently used in connection with the treatment of burns. These devices allow a skin graft of a particular size to be expanded so as to cover a greater area wound. Skin graft meshers are described in U.S. Pat. No. 5,004,468, No. 5,219,352 and No. 5,306,279, all assigned to Zimmer, Inc., of Warsaw Ind., and No. 6,063,094, assigned to L.R. Surgical Instruments Ltd. of Ofakim, Israel. These devices use one or more bladed cylindrical cutters and a support carrier to produce an array of slits in the skin graft. The meshing ratio, also known as a slit ratio, (i.e., 1.5:1, 3:1 or 6:1) refers to the approximate amount by which the graft expands; for example, a 1.5:1 meshing ratio provides a graft that covers approximately 1.5 times the area of the original graft. Different cutters are used to produce different mesh ratios. In general, as the mesh ratio increases, so does the number (or length) of slits that are formed in the graft.

Presently, a Zimmer Skin Graft Mesher is preferred. This device is manufactured by Zimmer, Inc.

The present invention encompasses the use of slit ratios up to approximately 6:1.

Alternatively, the slits 285 could be formed using a suitable die, or even by hand-slitting the source material 224 with a blade. Other cutting techniques, such as water jet or laser beam, also could be used.

A slit ratio of 1.5:1 is presently preferred because it results in an implant member 201 having both good strength and extensibility. As noted above, the slit ratio refers to the approximate amount by which the area of the resulting meshed graft is increased. A 1.5:1 ratio graft therefore will cover approximately 150% of the area of the source graft prior to meshing. Ratios of 3:1 and 6:1 also could be used, depending upon the amount of force that will be applied to the implant 201. In deciding which meshing ratio to use, it should be understood that higher meshing ratios, while they allow the use of less material, result in a more elastic implant member 201 which may have difficulty supporting the maximum loads likely to be encountered. By way of non-limiting example, using a piece of material 224 of the preferred length of 30 cm., after meshing that material 224 could be expanded under tension to approximately 45 cm.

As an alternative to slits 285, and as shown in FIGS. 22B-F, holes 86 could be formed in the implant member 1. Holes 86 may enhance wound drainage (and so reduce wound dehiscence), but the elastic properties of the resulting implant member 1 would not be the same. Also, unlike slits 285, where virtually no material is removed from the implant member 201, to form holes 86 it is necessary to remove (and so waste) material from the implant member 1, since the holes 86 must be formed by punching the implant member 1 with a die or cutter.

As a further alternative, slits 285 and holes 286 could be arranged in a generally alternating manner to insure the benefits of the slits 285 are still available.

With reference now to FIG. 30, the depicted implant member 201, which includes an array of slits 285, is under tension from force applied in the direction of arrow F. The applied force, which is preferably spread over the ends of the implant member 201 in generally uniform fashion, causes the slits 285 to open. The open slits 285 result in expansion of the implant member 201 by approximately its meshing ratio.

While the implant member 201 is under tension, the slits 285 define openings 285'. Openings 285' provide at least two benefits. First, some of the patient's tissue may extend into at least some of the openings 285', and that can increase the friction between the implant member 201 and the patient's body. Depending upon the manner in which the implant member 201 is placed in the body, owing to this increased friction, it may not be necessary to suture the implant member 201 into place. Second, over the course of time, tissue will grow into the openings 285', and that will help to secure the implant member 201 into place in the patient's body. Such ingrowth differs from ingrowth into the microstructure of the implant member 201; here, tissue will actually enter into and grow through the open slits 285 (openings 285') of the implant member 201 (which is not to say that tissue also cannot grow into the microstructure of the implant member 1). Second, fluid exchange through the implant member 201 is enhanced, since fluid and suspended and dissolved materials can pass through the openings 285'.

The precise shape of the openings 285' will be determined by both the length of the associated slit 285 and the magnitude of the force that is applied. Seen in the direction perpendicular to the Y-Z plane of FIGS. 29 and 30, the openings 285' are approximately lens-shaped. In practice, the shape of the openings may differ without departing from this invention.

Figure 31:
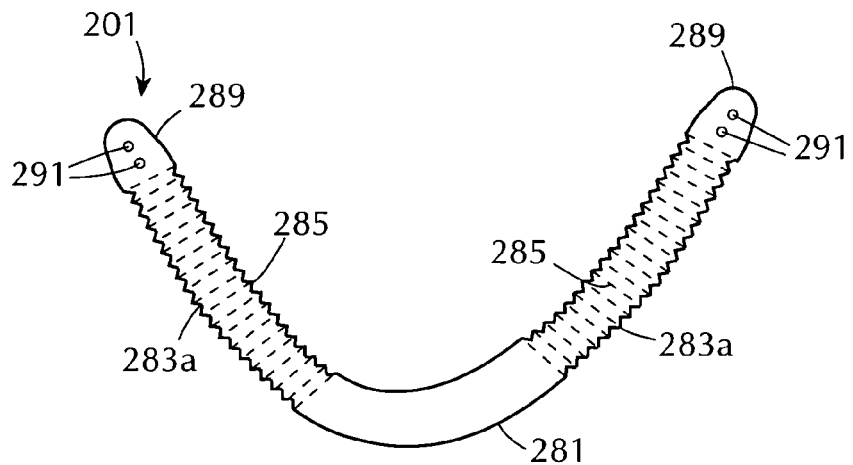
FIG. 31 is a perspective view of a support member suitable for use in a urethral sling suspension procedure.
Figure 32A:
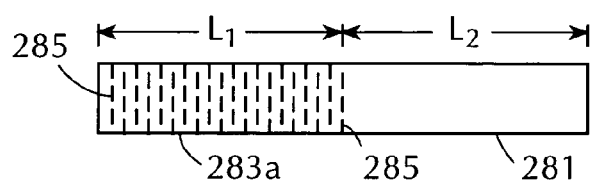
FIGS. 32A and 32B depict a support in accordance with this invention in the unexpanded and expanded state, respectively.
Figure 32B:
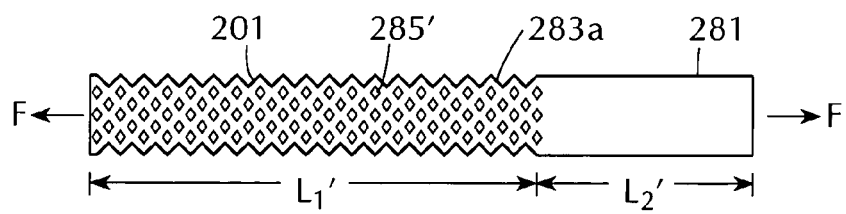
Figure 33:
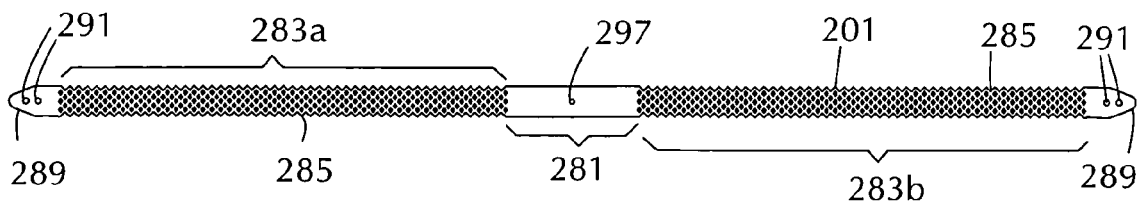
FIG. 33 is a top plan view depicting the support member of FIG. 31 in an expanded state as a result of tension applied thereto.

An embodiment of this invention particularly suitable for use as the support in a urethral sling suspension procedure is depicted in FIGS. 31-33.

As shown in FIGS. 31 and 33, implant member 201 has an unmeshed central region 281 free of any slits. A first perforated arm region 283a having slits 285 is located on one side of the central region 281, and a second perforated arm region 283b having slits 285 is located on the other side of the central region 281. Consequently, the central region 281 is disposed between the perforated regions 283a, 283b. FIG. 33, it will be appreciated, depicts the implant member 201 of FIG. 31 when tension has been applied thereto, so that the slits 285 open up.

As shown in FIGS. 32A-B, slits 285 are arranged in rows running across the width of the implant member 201. The slits 285 in these rows can be disposed in the manner described above in connection with FIGS. 29 and 30.

When introduced into the patient's body, the implant member 201 is positioned so that the central region 281 is located beneath and approximately centered with respect to the patient's urethra.

Because the central region 281, which does not have any slits, lies in the vicinity of the patient's urethra, the solid portion 281 of the implant member 201 can provide greater support for, and help distribute force over, the patient's urethra. Also, the smooth surface of the solid portion 281 may be less likely to irritate the urethral tissue than it would if slits were formed therein.

To aid the surgeon in positioning implant member 201, a small circular hole 297 can be formed at approximately the center of the central region 281. Alternatively, a colored dot or line, or any other suitable visual or tactile indicia, could be provided. This way, the surgeon can easily position the implant member 201 by arranging the implant member 201 so that the opening (or colored region) 297, or other center indicator, is located beneath or at least near the urethra.

In addition, the implant member 201 can (but need not) have one or more openings 291 formed at each of its tips 289. These openings 281 can serve as attachment points for an introducer needle or a connector such as that already described and shown in FIGS. 9A-D, which can be used to place the implant member 201 into the patient's body in the manner already described. While FIGS. 31 and 33 depict two openings 291 at each tip 289 of the implant member 201 to accommodate a connector 107 such as that shown in FIGS. 9A-D, which has two projections 157, and so help distribute the forces which are applied to the ends 289 of the implant member 201, just one opening 291 could be provided at each end, say, for use with the connector 107 shown in FIGS. 8A-B. Alternatively, no holes could be provided, in which case the projections 157 on the arms 153a, 153b, 155a, 155b of the connector 107 would, as the connector arms 153a, 153b, 155a, 155b are pressed together with the implant member 201 therebetween, pass through existing slits 285 in the implant material 224, or would pierce solid portions of the implant member 201 and form such holes.

FIGS. 32A-B show how the implant member 201 deforms and stretches in response to applied force F.

FIG. 32A shows the implant member 201, including slits 285, in the relaxed state. Owing to the inherent elasticity of the material 224 from which implant member 201 is made, the slits 285 remain closed.

FIG. 32B shows the implant member 201 subjected to tensile force F along its length. Such force F could be applied to each end 289 of the implant member 201 over an area or at one or more discrete points; uniform loading is preferred because it is less likely to apply excessive stress to any particular portion of the implant member 201. The resulting difference in shape between the unloaded and loaded implant member 201 can be seen by comparing FIGS. 32A and 32B.

The tensile force F causes the slits 285 to deform and change shape to openings 285', which are approximately lens-shaped. Again, the precise shape of the openings 285' will depend upon the size and spacing of the slits 285 and the properties of the material 224 from which the implant member 201 is made.

It will be noted that, under load F, the arm portion 283a stretches from length $L_1$ to length $L_1'$. The center portion 281 stretches from $L_2$ to $L_2'$. The amount of stretching of the arm portion 283a is greater than that for the central portion, 281, owing to the slits 253 (accordingly, $(L_1')/(L_1) > (L_2')/(L_2)$) formed in the arm portion.

The applied tensile force F also may cause the implant member 201 to "neck-down" in width. By way of non-limiting example, it is thought that an implant member 201 that is 2 cm. wide will, when loaded, narrow down to approximately 1.5 cm. in width. This is desirable because a strip 1.5 cm. wide is thought to be the optimal size for use in the typical patient's anatomy. These dimensions are given by way of example and not limitation, and it will be appreciated that other size implant members also could be provided.

The implant member 201 is preferably made from material 224 which retains its elasticity, and so, when tension is not applied to the implant member 201, the inherent resiliency of the material closes slits 285.

The slits 285 can be distributed uniformly throughout perforated arms 283a, 283b, as shown in FIGS. 31 and 33. Alternatively, the slits 285 could be distributed in an asymmetric manner (not shown), for example, the implant member 201 can be formed with fewer slits 285 near the central region 281, and more slits 285 near the free ends 289 of the meshed arm section 283a, 283b. It is expected that with this configuration, the strength of the implant member 201 beneath the urethra and flexibility of the meshed arm sections 283a, 283b will be increased.

In some instances, it may be desirable to have the slits 285 in the implant member 201 remain open even when tension is not applied. One way to do this is by first forming the slits 283 in the implant member 201, applying tension to the implant member 201 to cause the slits 285 to open and form holes 285', and then, while the implant member 201 is still under tension, applying cross-linking agent to, or carrying out a cross-linking treatment on, the implant member 201. This cross-linking will "set" the implant member 201 in its deformed shape so that even when tension is no longer applied the implant member 201 will retain its expanded arrangement and holes 285' will be maintained. This cross-linking can be effected in known manner, and so need not be described in further detail.

With reference now to FIG. 35, another alternative embodiment of this invention is shown. In this embodiment, the implant member 301 is formed with slits 385 throughout substantially all of the length of the implant member 301. The ends 389 of the implant member 301 can be left unmeshed to facilitate attachment of the implant member 301 to the equipment used for placement of the implant member 301 in the patient's body. In FIG. 35, the ends 389 of the implant member 301 have holes 391 for use in attaching the implant member 301 to the equipment used for placement. This embodiment has a single uniform portion 381 comparable to the center portion 281 of the previous embodiment. Because the portion of the implant member 301 underneath the urethra is meshed, tissue ingrown under the urethra could be improved.

FIGS. 36 and 37 depict a further embodiment of this invention. In this embodiment, the implant member 401 has an elongated portion 481 similar to that depicted in FIG. 35, as well as an enlarged portion 482 located at the center of the elongated portion 481. These drawings differ in that FIG. 36 depicts an implant member 401 having attachments holes 491 at its ends 489.

FIG. 37, which can be prepared by cutting off the tips of the arms 481, has no openings at its tips. Thus, the ends 489 of the implant member 401 are meshed and do not have other openings for attachment; rather, some of the slits 485 are used as attachment points.

In each of these embodiments the elongated section 481 and the enlarged portion 482 have slits 485 formed therein. When tension is applied along the length of the elongated portion 481, the slits 485 open to form diamond shaped openings or holes 485'. By applying tension to the sides 480 of the enlarged portion 482, the slits 485 in the enlarged portion 482 will open in the same manner. It will be appreciated that, owing to the geometry of the implant member 401, it may be preferable to apply force to the sides 480 of the enlarged portion 482 by attaching each of those sides 480 at one or more points to the patient's tissue, since such force will serve to hold the slits 485 open and thereby provide benefits as set forth above.

Alternatively, the implant member 401 could be subjected to tension and thereby be deformed to open the slits 485 outside the body and then treated to fix the implant member 401 in its deformed position. One way to do this would be by a suitable cross-linking treatment, as already discussed.

The enlarged portion 482 is positioned and dimensioned to lie beneath the urethra. Owing to the greater area covered by the enlarged portion 482, the pressure applied to the patient's tissue in the vicinity of the urethra can be reduced, since the enlarged portion 482 distributes force over a larger region.

This implant member 401 is thought to be particularly suited for cystocele repair procedures or other surgical procedures involving the support of body organs. If desired, the enlarged portion 482 can be secured in place for such a procedure by passing one or more sutures through the enlarged portion 482 into the patient's tissue, or using any other suitable attachment technique now known or hereafter developed.

The enlarged portion 482 can be formed as an integral part of the implant member 401 (the entire strip will be formed from a single piece of suitable material) or can be attached to a separate elongated strip of material. The elongated portion 481 and enlarged portion 482 can be joined together by suturing, biocompatible adhesive, or any other suitable technique now known or hereafter developed.

As shown in FIG. 37, the enlarged portion 482 can include a circular opening 497 which visually assists the surgeon in finding the center of the implant member 401, in the manner already described above.

Although the foregoing embodiments of this invention employ acellular dermal tissue, and, more preferably, acellular porcine dermal tissue, this invention is not to be limited thereto. Any other suitable material, whether natural or synthetic, or even a combination thereof, can be used. Other examples of suitable materials that could be used with this invention include allografts, xenografts and autografts, and absorbable and non-absorbable synthetic materials.

As a further alternate configuration, it may be desirable not to have slits along the edges of the meshed sections so that the slits are only formed in the center of the implant member (not depicted). This will alter the elastic properties of the implant member. Also, one or more regions not having any slits and running along the length of the implant member could be provided. For example, the implant member could have an elongated rectangular region running parallel to the length of the implant member, in the direction of axis Z (not shown). The rectangular region could be arranged about the centerline of the implant member 1. If more than one rectangular region is used, they could be arranged symmetrically with regard to the longitudinal (as opposed to the transverse) centerline of the implant member.

Although FIGS. 31-33 and 35-37 depict implant members 301 and 401 in which slits 385 and 485 are formed in lines parallel to the long axis of the implant member 301 and 401, respectively, this invention is not limited to those arrangements. By way of non-limiting examples, all of the slits could be formed, parallel to one another, at any angle between 0-180° to the implant member's longitudinal axis.

Figure 34:
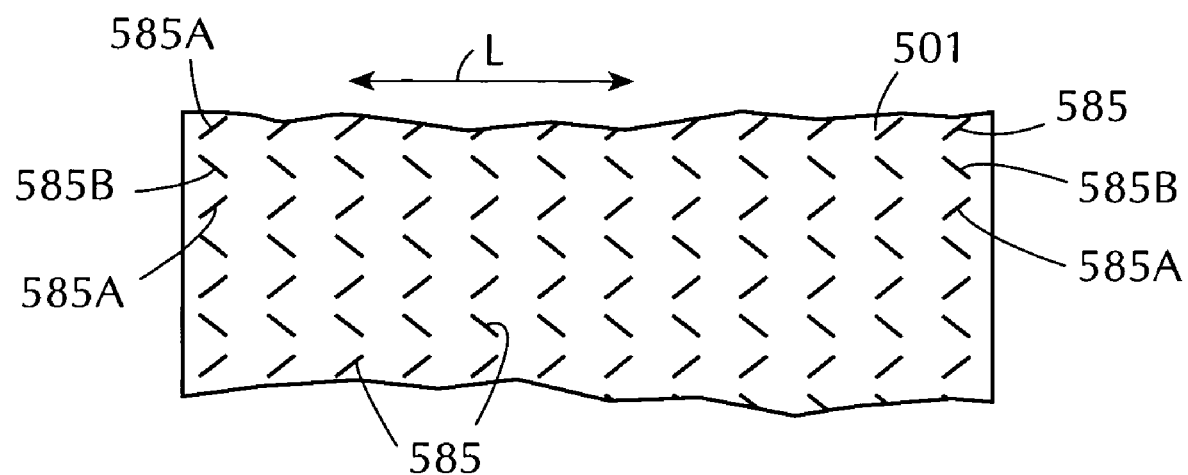
FIG. 34 is a top plan view in close-up showing a further embodiment of this invention having an alternate arrangement of slits.

Nor must all of the slits be arranged in parallel to each other. With reference now to FIG. 34, and by way of nonlimiting example, an implant member 501 can be constructed having rows of slits 585A oriented at a first angle and alternating with other rows of slits 585B oriented at a second angle relative to the longitudinal axis of the implant member 501. This results in a "herringbone" pattern of slits 585. Force will be applied along the long axis of the implant member 501, represented by arrow L. Further, there may be other situations where it is desirable to apply force to the implant member 501 at some other angle. In that case, owing to the different orientations of the slits in rows 585A and 585B, the implant member 501 may have different tensile properties along its length and width As a further variation, slits intersecting at right angles to form "+"-shaped slits could be arranged in a grid pattern (not shown). As a still further variation, in order to increase isotropy of the implant member a second grid of "+"-shaped slits, rotated by 45°, could then be interlaced with the first grid of slits (not shown). Other arrangements of "+"-shaped slits, or other shapes of intersecting slits, also could be used. Such slits could be formed in a single pass using correspondingly-shaped cutters or in multiple passes, with slits of one orientation being formed in one pass, slits in another orientation being formed in a different pass.

Another way to obtain an implant member with more uniform tensile properties would be to form the slits in the implant member with a random arrangement (not shown). Since the slits as a group are arranged without any particular preferred direction, the resulting implant member should not elongate in any one direction more than another (this presumes the number of slits is sufficient to offset the effect of any one slit).

Also by way of example only and not limitation, one side of the implant member could be formed with more or larger slits than the other in order to provide asymmetrical elastic properties (not shown). When placed in the patient's body, the more heavily perforated portion of the implant member will expand to a greater degree than the other portion of the implant member.

If desired, the slits also could be arranged in an asymmetrical pattern (not shown). This would affect the manner in which the implant member expands under tension.

Also by way of example only and not limitation, one side of the implant member could be formed with more or larger slits than the other (not shown). Then, when placed in the patient's body, the more heavily perforated portion of the implant member will expand to a greater degree than the other portion of the implant member. In other words, differential slit arrangement can provide an implant member with asymmetric properties.

A random arrangement of slits also could be employed—since the slits are, overall, arranged without a particular preferred direction, the resulting implant member should not elongate in any one direction more than another, provided the number of slits is large enough so that the effect of any one slit is not too great.

The implant member 301/401/501 prepared in this manner can be joined to an introducer needle using suitable connectors, whether separate or permanently attached to the implant arms, in the manner discussed earlier, for example, and as shown in FIG. 38, which shows such an implant member 301/401/501 in the non-tensioned state. Each connector can be attached to the introducer needle, and then to the tip of one of the arms of the implant member, and the introducer needle can then be used to draw that arm of the implant member into position in the patient's body.

Alternatively, a connector similar to that shown in FIG. 39 could be permanently affixed to the tip of each arm of the implant member, in the manner discussed in connection with FIG. 39.

In a further embodiment of this invention, the implant member can at least in part be contained in a sheath of flexible material (not shown) having suitable friction and porosity properties, such as PTFE (Teflon®). The flexible material can be joined to the implant material, connected by passing a suture around the sheath to squeeze the sheath and implant therein against the base of the connector, or the implant material could "float" therein.

In still another embodiment of this invention, the implant material could be contained in the sheath and the sheath itself be pulled into position by the introducer needle attached thereto. Once in position the sheath could be removed, leaving the implant material exposed.

Turning now to FIGS. 13, 14A-B, 15A-C and 16A-D, the introducer needle 3, connector 7 and implant member 1 according to the present invention are shown in various stages of assembly. Those skilled in the art will appreciate that the following discussion can be applied to the different embodiments of this invention which have been described.

FIG. 13 shows the introducer needle 3 securely joined at one end to the handle 5. One end 89 of the implant member 1 is free, and the other end 89 is joined to one end of the connector 7. As better seen in FIGS. 14A and 16A, the other end of the connector 7 is being secured to the other end 4 of the introducer needle 3. The projection 57 in the connector has begun to enter the opening 27 in the introducer needle end 4, as the upper arm 55a has not yet reached its closed position.

FIGS. 15A-C and 16A-C show both sides of the connector 7 joining the introducer needle 3 to the implant member 1.

Again, it should be noted that in order to minimize tissue trauma during use, all of the surfaces of the connector 7 are preferably tapered and/or rounded.

In some instances it may be desirable to reduce the amount of material required to form the body of the implant member, the body of the implant member being the portion of the implant member which remains in the patient's body after the surgical procedure is completed to support the patient's tissue.

Figure 38:
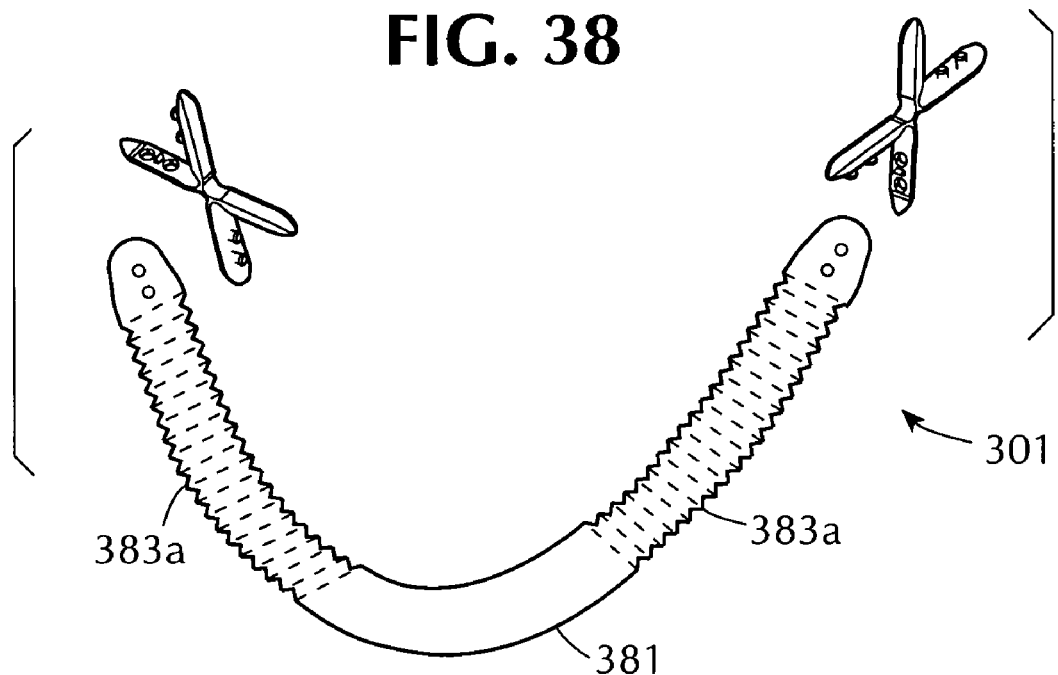
FIG. 38 is a perspective view showing one embodiment of an implant member used with connectors, and in the non-expanded state.

For example, the processed natural material that can be used in implant slings such as that shown in FIGS. 31, 33 and 38 may be expensive, and so reducing the amount of material that is required will reduce the cost of the implant member.

The present invention reduces the amount of material used to form the body of the implant member by providing removable extensions made from less expensive material at the ends of the implant member body. The removable extensions, which provide added working length during implantation, are long enough so that they allow the surgeon to position and tension the implant member in the same manner as longer strips, and these extensions then can be removed at the conclusion of the implant procedure. Long-them anchoring still comes from the tissue implant.

While this aspect of the present invention is thought to be especially suited for use with processed natural materials, it is not to be limited thereto. Any other suitable biocompatible implant material could be employed.

One example of an implant member configuration having removable extensions on the sides of a central body is depicted in FIGS. 42-45. In this embodiment, the implant member 601 consists of a middle urethral support section 681 and two extension loops 690. The middle urethral support section 681 can be made of any suitable material, such as the materials discussed earlier in connection with other embodiments of this invention. Presently, natural material is preferred, owing to its compatibility with body tissue.

By way of non-limiting example, the middle urethral support 681 can be about 30 cm. in length. Other size supports can be employed according to the needs of any particular surgery.

The extension loops 690, each of which passes through two holes 691 in the end 689 of the middle urethral support 681, can be made of any suitable flexible material, whether natural or synthetic, monofilament or multifilament, provided the selected material possesses suitable tensile strength, flexibility and biocompatibility. Presently, synthetic materials are preferred, and the extension loops 690 shown in FIGS. 42-45 are tubes of polyurethane or suture material, and any other suitable material also could be used. The loops 690 can be formed from solid filaments, intertwined braids or strands. If made from polymeric material, the extension loops 690 can be injection molded, extruded or, if multi-strand woven. If made from metal, the extension loops 690 can be made from wire.

Figure 45:
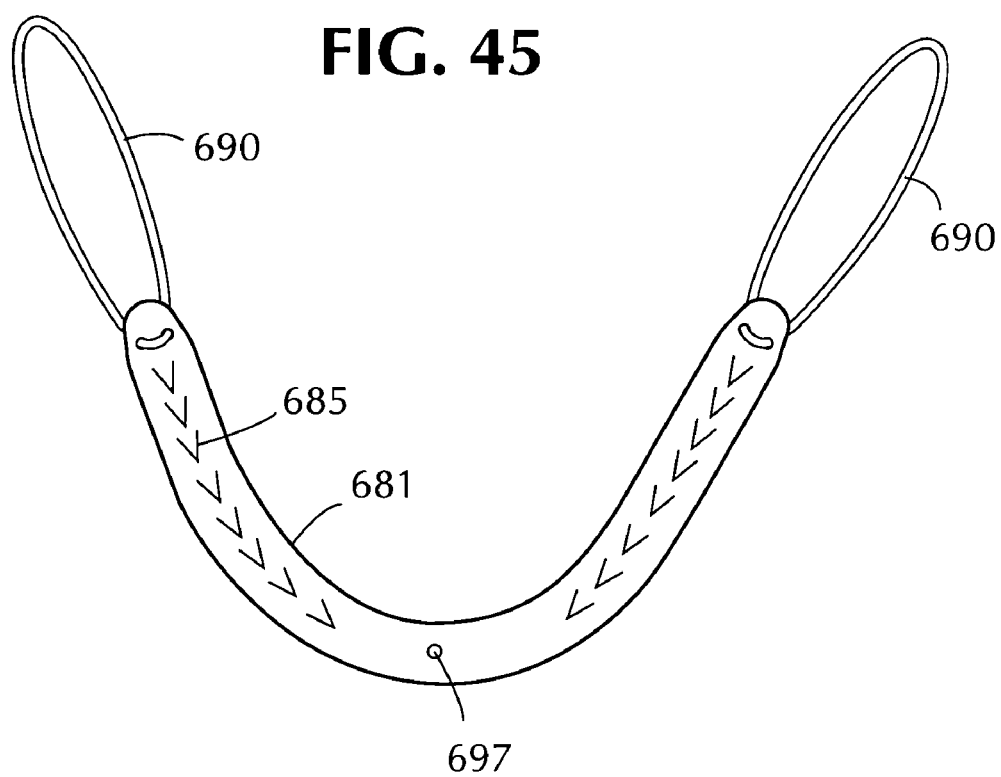
FIG. 45 is a perspective view of an implant member.

With reference now to FIGS. 42-43C and 45, one extension loop 690 is attached to each end 689 of the middle urethral support section 681 through one or more holes 691 formed in the middle urethral support section 681. FIGS. 42, 43B and 45 show an embodiment in which the middle urethral support section 681 has two holes 691 lying on a line perpendicular to the long axis of the implant member 601. FIG. 43A depicts an embodiment in which the extension loop 690 passes through a single hole 691 in the end 689 of the middle urethral support section 681. FIG. 43C shows an embodiment in which the extension loop 690 passes through two holes 691 that lie on a line parallel to the axis of the implant member 601. Presently, the use of two holes 691 at each end 689 of the middle urethral support section 681 is preferred because the holes 691 better distribute applied loads than one hole 691. Thus, it also will be appreciated that more than two holes 691 could be provided at each end 689.

One of the benefits of the composite implant member 601 is that after the implant member 601 has been properly positioned in the patient's body, the connectors 607 and loops 690 can be detached, leaving only the middle urethral support section 681 in place. This is beneficial because it reduces the amount of foreign material in the patient's body and so allows for faster healing of the tissue channel wound formed during placement of the implant member. Thus, it may be preferable for the holes 691 in the middle urethral support section 681 to be somewhat larger in diameter than the extension loop 690 passing therethrough, so that the loop filaments can slide through the holes 691 without binding, which will help during placement of the implant member 601 in the patient's body. This also allow for easy removal of the extension loop 690, as discussed below.

FIG. 52 is a side cross-sectional view showing how the implant member 601 of FIG. 45 can be joined to a introducer needle 603 through a hole or slot 627 formed in the introducer needle 603.

Figure 44A:
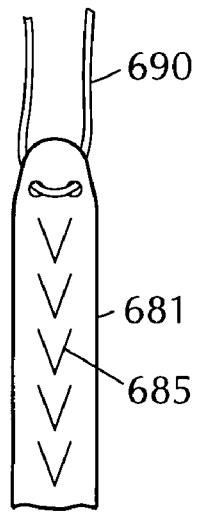
FIGS. 44A and 44B are front perspective views of the implant member of FIG. 42 showing the effect of force applied thereto.
Figure 44B:
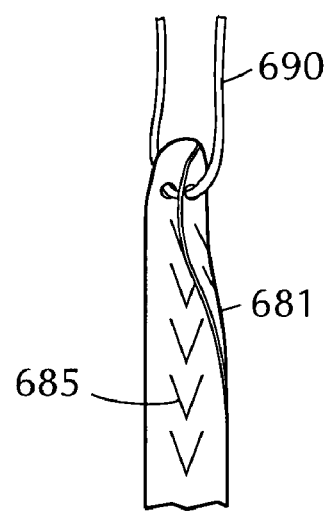

The configuration depicted in FIGS. 42, 43B and 45 is may be preferred because, as shown in FIGS. 44A-B, when tension is applied to the extension loop 690, the implant member 601 changes shape from flat to somewhat curved. The curved tip 689 of the implant member 601 forms a tapered nose section that allows for easier implantation of the implant member. The curving of the tip 689 of the implant member 601 also encourages flaring out of the slits 685 of the implant member 601, which improves the implant member's anchoring ability.

One benefit of the embodiment depicted in FIGS. 42-45 is that it can be positioned without the use of a separate connector, provided a suitable proper introducer needle 603 is employed. FIGS. 53A-B depicts one example of such an introducer needle.

With reference now to FIGS. 53A-B, an introducer needle 603 that can be used to directly attach to the extension loop 690 of an implant member 601 as shown in FIGS. 42-45. The introducer needle 603 has a central body section 611 that is generally circular or oval cross-section, and a spatulated section 613 just proximal of its tip 616. The spatulated section 613 and tip 616 are shaped to allow for the dissection of tissue by the advancing tip 616. The tip 616 also has a "T"-shaped cavity 634 which receives the extension loop 690. As shown in FIG. 53A, the extension loop 690 passes into the cavity 634 through the short leg 634a of the "T", and is then received in one of the two arms 634b, 634c of the "T". The extension loop 690 is attached to the needle 603 prior to passage into the patient's body. The portion of the "T"-shaped cavity 634 into which the extension loop 690 is placed will depend upon whether the extension loop 690 is to be positioned by advancing or retracting the introducer needle 603. If the introducer needle 634 advances forward to position the implant member 601, then the extension loop 690 is placed in the proximal leg of the "T" 634b, and if the needle is retracted backward to draw the implant member 601 into place it is placed in the distal part of the "T" 634c. To avoid movement of the captured extension loop 690, the "T"-shaped cavity 634 can be made slightly narrower than the extension loop 690, so that when the extension loop 690 is placed into the "T"-shaped cavity 634 it is compressed and secured in place.

Figure 46A:
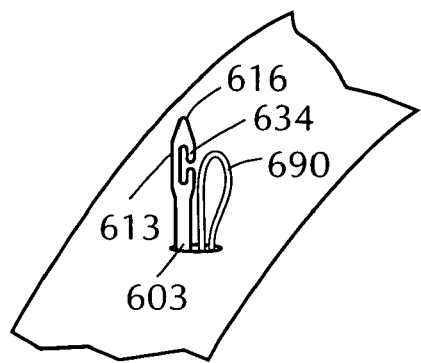
FIGS. 46A and 46B are perspective views showing a portion of the implant member of FIG. 45 during placement in a patient.
Figure 46B:
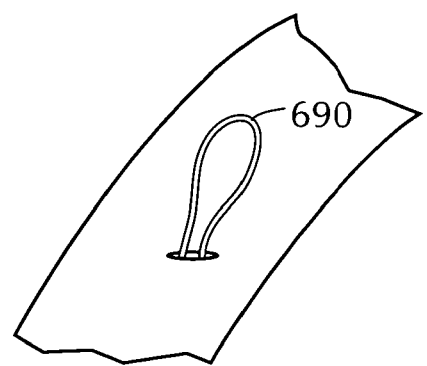
Figure 47:
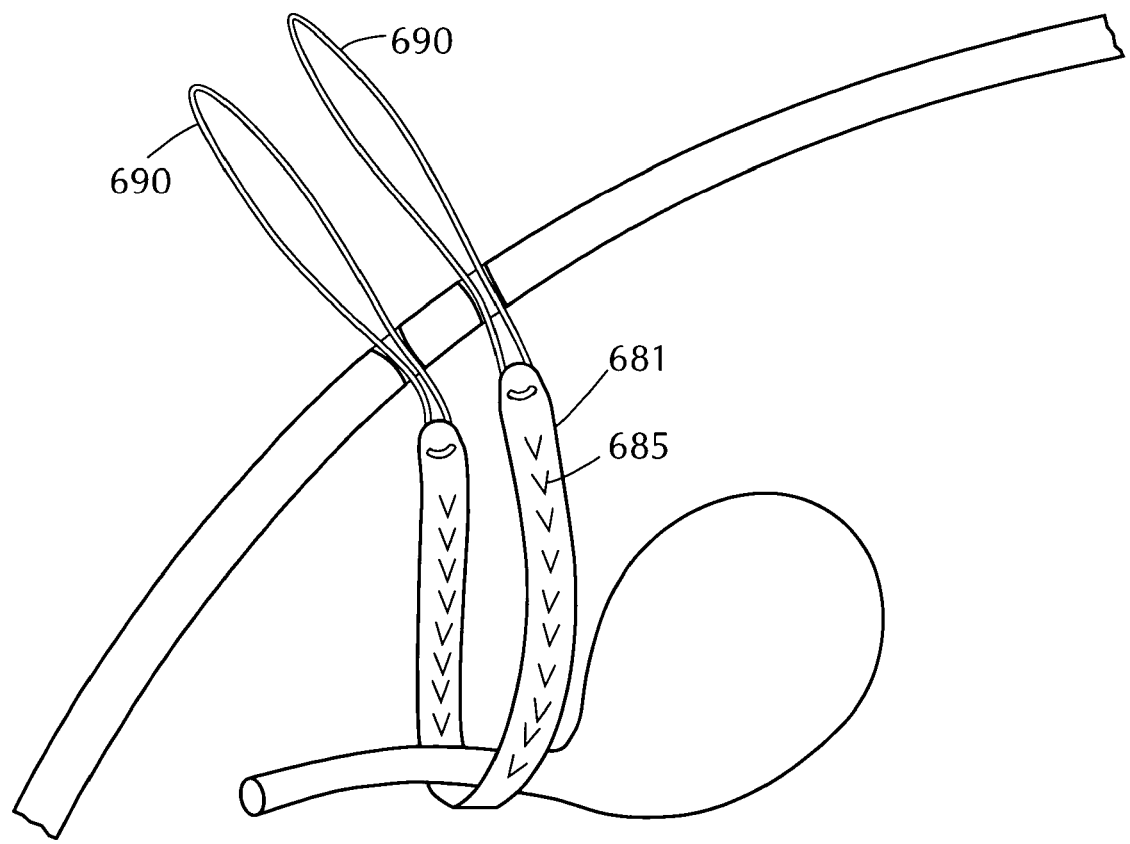
FIG. 47 is a side cross-sectional view showing the implant member of FIG. 45 as positioned in a patient's body.

FIGS. 46A-B and 54 show how the introducer needle 603 of FIGS. 53A-B is used. As depicted in FIG. 54, the introducer needle 603, with the filament of the extension loop 690 held in the "T"-shaped cavity 634, is advanced from an incision in the vicinity of the urethra behind the pubic bone and upward until it emerges from an abdominal incision. As shown in FIGS. 46A-B, the extension loop 690 can then be disengaged from the "T"-shaped cavity 634 in the distal tip of the introducer-needle 603 and the introducer needle 603 then can be backed out of the retropubic space, leaving just the extension loop 690 protruding from the patient's abdomen. The extension loop 690 is then used to draw the implant member 601 into position beneath the urethra. As shown in FIG. 47, the extension loops 690 and the central support 681 are dimensioned such that the extension loops 690 can be cut at any point and removed while the central support 681 remains beneath the abdominal wall, anchored in the surrounding host tissue.

It should be noted that the extension loop 690 shown in FIG. 54 is long enough so that even when the end of the extension loop filament held in the introducer needle 603 that protrudes up from the abdominal incision, the urethral support has not yet even been drawn into the patient's body. This way, the extension loops 690 can be placed in the patient's body and used to adjust the position of the implant member 601 after the introducer needle 603 has been removed.

The surgeon then applies moderate tension to the two exposed extension loops 690 to draw the urethral support 681 into position beneath the patient's urethra and to apply the required amount of pressure to the patient's tissue. At this point, the ends of the urethral support 681 still do not protrude out of the body from the abdominal incisions, and the proximal portion of the extension loops 690 remain within the body, as shown in FIG. 47. Alternatively, if a longer urethral support 681 is used, the ends of the support could protrude from the abdominal incisions.

It is now desirable to remove the extension loops 690 so that the abdominal incisions can be closed. To do this, each extension loop 690 is cut at a single point, as shown in FIG. 57A. Since the filament is now severed, when tension is applied to the associated connector (not shown), the filament is pulled out from the hole(s) 691 in the urethral support 681, as shown in FIGS. 57B-C, and is drawn outward from the patient's body, the longer leg of the filament passing through the opening(s) 691 in the middle urethral support section 681 and out of the patient's body.

It also will be appreciated that it is undesirable to cut both filament legs, because then it will be less convenient to draw out the portion of the filament that was isolated by the two cuts.

The introducer needle 603 and handle 605 shown in FIG. 54 can be joined together permanently. By eliminating the latch mechanism of a movable handle, cost can be reduced and the device construction simplified.

Figure 55:
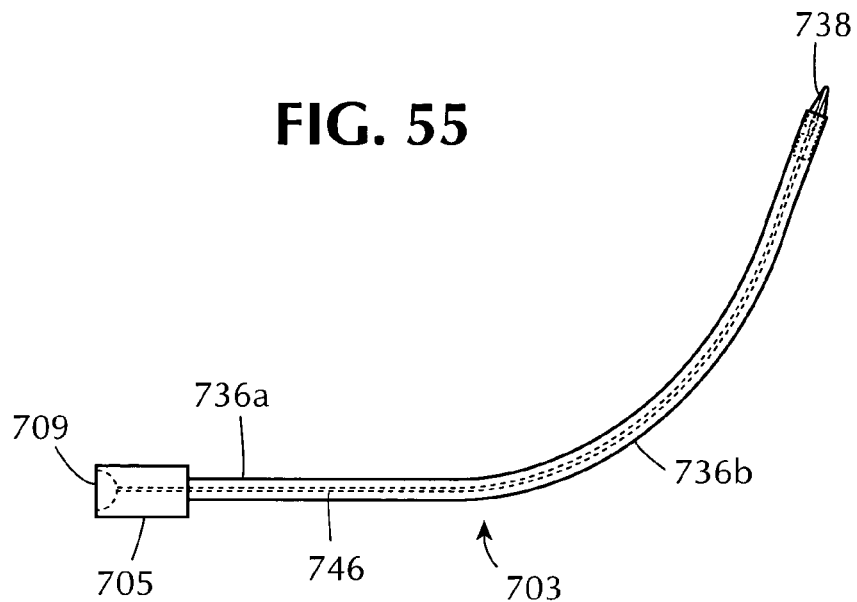
FIG. 55 is a simplified cross-sectional view of an introducer needle according to this invention.
Figure 56A:
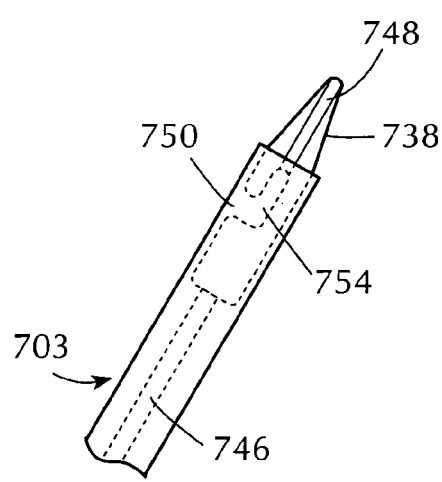
FIGS. 56A-C are side plan views showing a portion of the introducer of FIG. 55 in different stages of use.
Figure 56B:
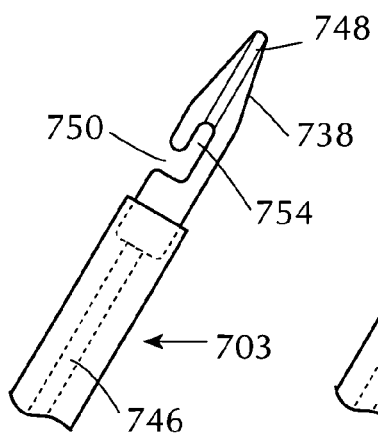
Figure 56C:
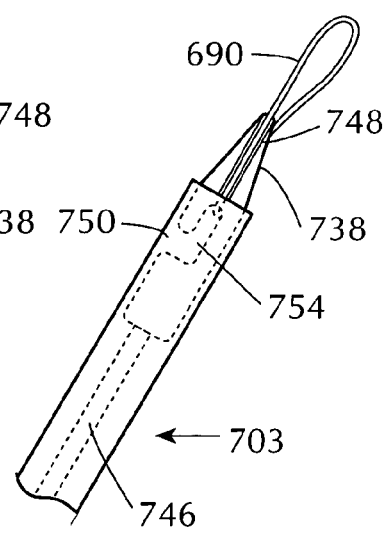

FIGS. 55-56C depict an alternative configuration of an introducer needle 703 that can be used to draw an implant member having an extension loop into place in the patient's body. As shown in FIG. 55, the introducer needle 703 has a generally straight body portion 736a leading to a curved portion 736b. A handle 705 having a pushbutton 709 is located at the proximal end of the body portion 736a. A movable conical tip 738 is located in at the distal end of the needle 703, and a rod 746 connects the conical tip 738 to the pushbutton 709. The pushbutton is biased by an elastic member such as a spring (not shown) so that it pulls the movable conical tip 738 backward toward the handle 705.

FIGS. 56A-C show how the movable tip 738 of the introducer needle 703 of FIG. 55 is used to capture the extension loop 790 of an implant member 701 like that shown in FIG. 45.

FIG. 56A depicts the movable conical tip 738 pulled backward into the tip of the curved portion 736b of the introducer needle 703 under the influence of the elastic member, as just discussed. The movable conical tip 738 preferably has at least one and more preferably two grooves 748 running from its tip to its rear, and these grooves 748 receive the filaments of an attached extension loop 690 (not shown). The conical tip 738 also has an opening 750 on one side that leads to a larger internal recess 754 (in other words, a finger blocks much of the opening 750 in the side of the movable conical tip 738). The base of the conical tip is attached to a flexible rod 746, which in turn is connected to the biased pushbutton 709.

Turning now to FIG. 56B, the movable conical tip 738 has been shifted forward in position until almost all but the proximal end of the movable conical tip 738 projects forward from the distal end of the curved portion 736b of the introducer needle 701. The movable conical tip 738 is shifted forward by depressing the pushbutton 709 in the handle 705 with force sufficient to overcome the biasing member (not shown). The movable conical tip 738 then advances so that the opening 750 in the side of the conical tip 738 is fully-exposed, and can now receive the filament of the extension loop 690.

Once the filament of the extension loop 690 is received in the internal recess 754 of the movable conical tip 738, the user can release the pushbutton 709. The biasing spring then retracts the movable conical tip 738 back to its original position in the needle body 736. Because the opening 750 in the movable conical tip 738 is covered by the needle body 736, the filament of the extension loop 690 cannot escape from the internal recess 754. Also, the filament of the extension loop 690 lies in the grooves 748 formed in the side of the movable conical tip 738.

It is contemplated that this introducer needle 703 could be used for both abdominal and vaginal placement of the implant member. In the abdominal approach, the introducer needle 703 is driven downward from an abdominal incision, behind the pubic bone, and out beneath the urethral. The movable conical tip 738 is then actuated by depressing the pushbutton 709 to move the rod 746 forward, advancing the movable conical tip outward, to capture the extension loop of an implant member. The introducer needle 703 is then retracted with the extension loop attached until the extension loop emerges from the abdominal incision. The introducer needle 703 is disconnected from the implant member and then the extension loop is drawn upward by the surgeon to pull the middle urethral support into place. Then, the extension loop is cut and the loop is removed. This procedure is repeated on the contralateral side of the body.

In a vaginal approach, the extension loop is first captured by the needle tip 738 outside the body. Then, the introducer needle 703, with the attached extension loop, is driven inward beneath the urethra and upward around the pubic bone, until the movable needle tip 738 and captured extension loop emerge from an abdominal incision. The extension loop is then released from the needle tip 738 and the needle 703 is withdrawn from the patient's body. Tension is applied to the extension loop to draw support section of the implant member into the proper position. After that, the extension loop is cut and removed. Finally, the procedure is repeated on the contralateral side of the body.

Figure 48:
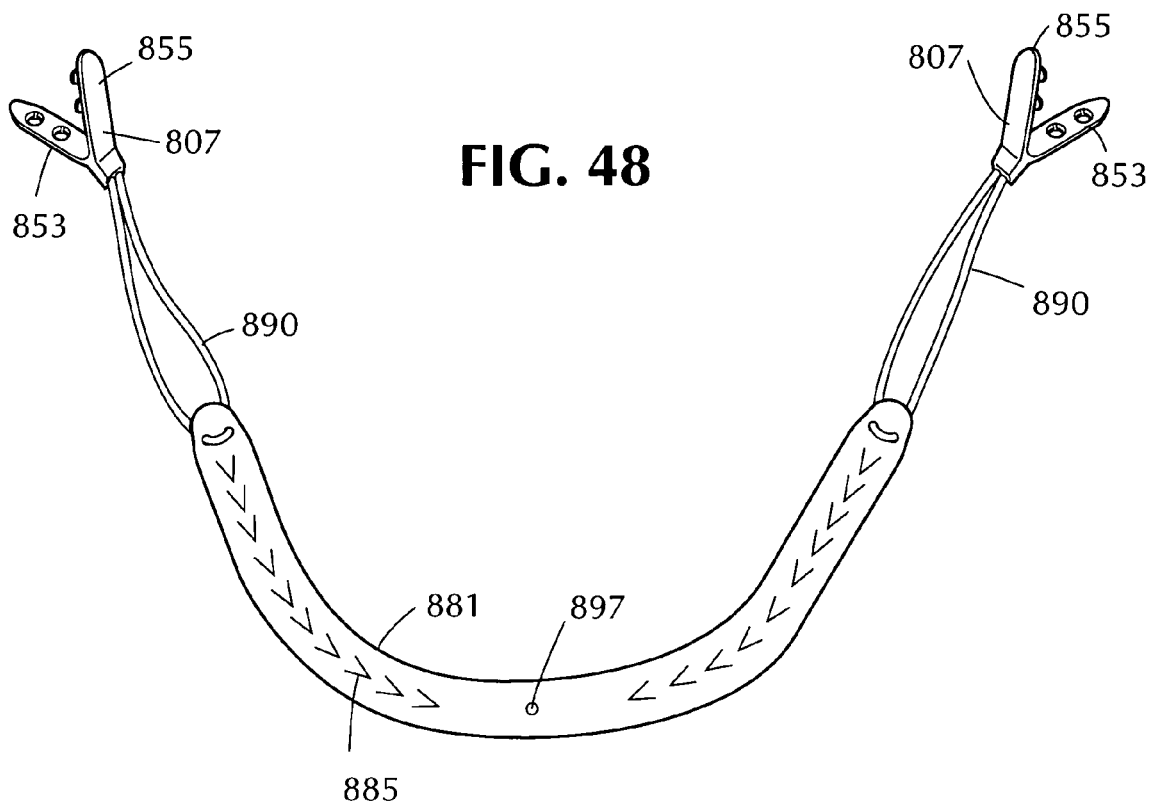
FIG. 48 is a perspective view of another implant member.

FIG. 48 depicts a variation of the implant member shown in FIG. 45. In this embodiment, each extension loop 890 has a connector 807 located at its distal tip. This connector 807 has at its distal end movable lower and upper arms 853, 855 which are in appearance and function the same as the upper and lower arms of the connectors shown in FIGS. 9A-D. The connector 807 is joined at its proximal end to the filament of the extension loop 890. The precise manner in which the connector 807 is joined to the filament will be described later.

Figure 49:
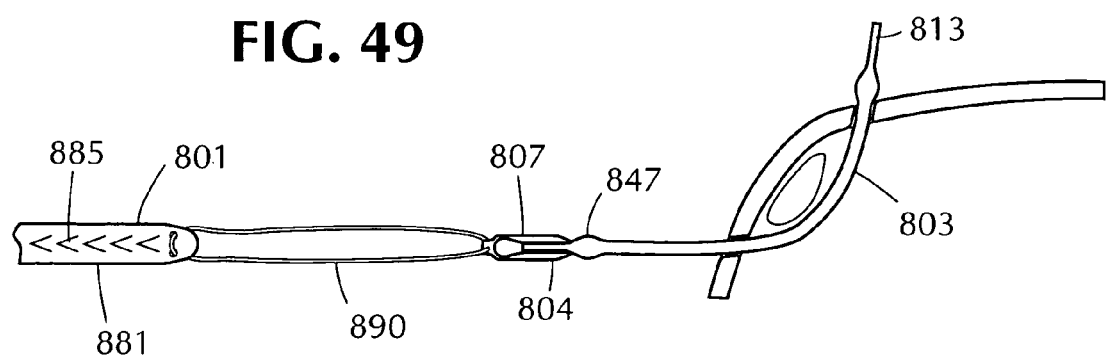
FIG. 49 is a side cross-sectional view showing the implant member of FIG. 48 during positioning in a patient.

FIG. 49 shows how an implant member 801 as depicted in FIG. 48 having extension loops 890 can be positioned in a patient. This configuration is intended to be used with an introducer needle 803 which can be removably attached to the handle 805, so that the handle 805 can be used to guide the introducer needle 803 beneath the urethra, upward around the pubic bone and out of the abdomen. If the introducer needle 803 used is symmetrical, the handle 805 can then be attached to the portion of the introducer needle 803 protruding from the abdomen and assist the surgeon in drawing the implant member 801 into the body.

With continued reference to FIG. 49, the connector 807 is attached to the end 804 of an introducer needle 803 having an internal slot 827 in the end 804 by bringing the lower and upper arms 853 and 855 together. At least one and preferably two projections 857 extend from one of the arms through the internal slot 827 and are received in a matching opening(s) 861 in the other arm (not shown). Then, when the introducer needle 803 is retracted backward toward the patient's abdomen, the implant member 801 joined thereto by the connector 807 is drawn inward into place in the patient's body. The surgeon moves the implant member 807 into its final position by selective tensioning the extension loops 890. Once the implant member 801 is properly positioned, the extension loop 890 is cut at one place and the extension loop 890 is detached from the urethral support portion (center section) 881 of the implant member 801, which remains in place in the patient's body after the surgery is complete.

FIGS. 50A-B depict one exemplary construction of a connector 807 that can be used to join the filament of the extension loop 890 to the center section 881. The connector 807 shown in FIG. 50A has a single projection 857 and a matching hole 861 in the upper and lower arms 855, 853 respectively, and a central web 851, to which the upper and lower movable arms 855, 853 are joined by living hinges 856. The single projection 857 allows for some rotation of the connector 807 once it is attached to a needle. A clevis structure 858 is attached to the other side of the central web 851. Then, as seen in FIG. 50B, the filament of the extension loop 890 is arranged to pass around the vertical post 860 of the clevis structure 858. Preferably, the filament of the extension loop 890 freely passes through the clevis 858.

FIG. 50B depicts an alternate connector 807 having two projections 857 and matching holes 861, as well as a "+"-shaped projection 862. These aspects of this embodiment are similar in construction and function to structure shown in FIG. 10, already described. The two projections 857 prevent rotation of the connector 807 after it is attached to the needle (not shown). The clevis 858 used in this embodiment is the same as that just described with reference to FIG. 50A.

FIG. 50C depicts an alternative arrangement for joining the connector 807 to the filament of the extension loop 890. In this arrangement, the connector 807 has a central web 851 similar to that shown in FIGS. 50A-B. In place of the clevis, however, there is a panel 866 having a flat wall 866'. The two ends 868 of the extension loop filament abut and are joined to the flat wall using any suitable known attachment scheme, such as press-fitting, adhesive bonding, ultrasonic welding or any other suitable technique.

This configuration may be advantageous because the extension loop, when cut at a single point, remains attached to the connector 807, in contrast to the clevis arrangement of FIGS. 50A-B, where the extension loop 890 can slide freely out of the connector 807. Having a permanently attached extension loop 890 may prevent loss of the filament in the operating room.

The filament can be formed into the extension loop using any of a number of different techniques. FIGS. 58A-G show various ways to form extension loops. FIG. 58A shows a filament bonded to a sleeve bushing. FIG. 58B depicts a knotted filament. As seen in FIG. 58C, the filament is continuous (this could be done by butting the two ends of the filament together and melting or bonding them). FIG. 58D shows an internal connector inserted into the ends of the filament. FIG. 58E depicts an ends connector which receives the two free ends of the filament. FIG. 58F shows a figure-8 shaped extension loop formed by twisting the oval loop, and FIG. 58G depicts a figure-8 shaped extension loop formed by using a sleeve to bring together the central portion of the oval loop.

Of these approaches, the use of an end connector may be of the most interest because it allows a length of tubing to be quickly formed into an extension loop.

Figure 59:
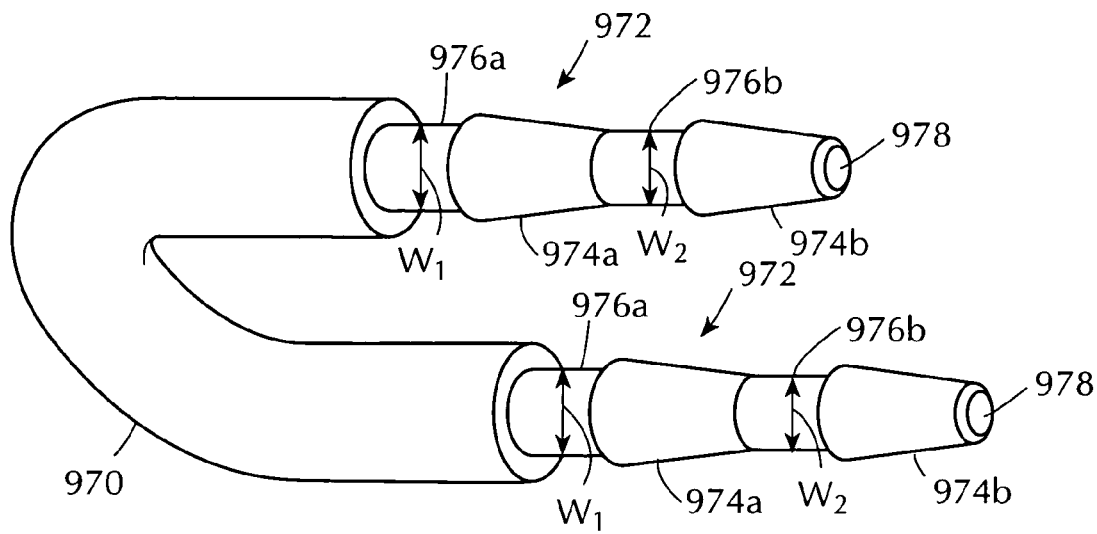
FIG. 59 is a perspective view showing a portion of a loop connector according to this invention.
Figure 60A:
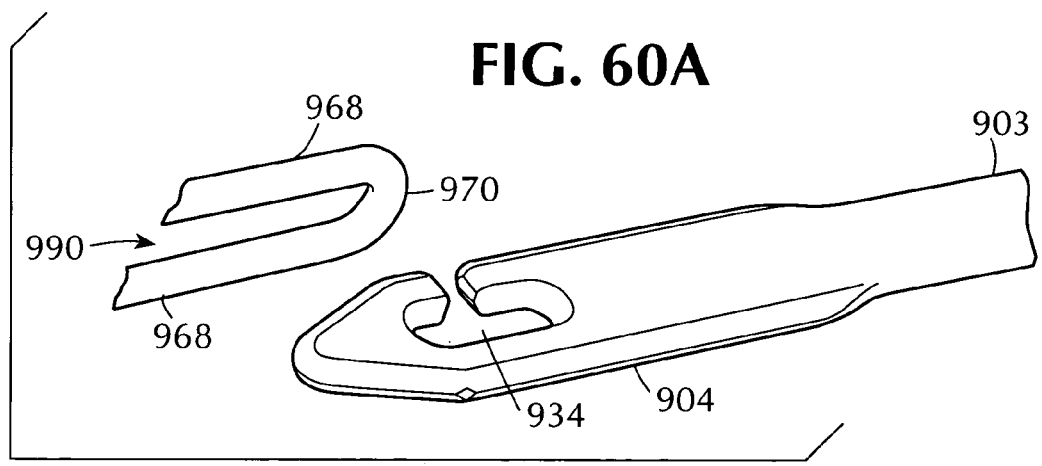
FIGS. 60A and 60B are perspective views showing another embodiment of this invention in which a loop is captured by an introducer needle.
Figure 60B:
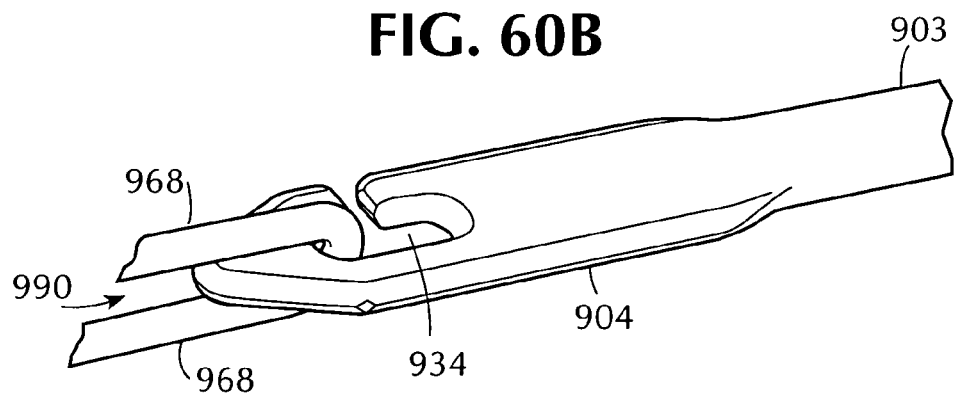

With reference now to FIGS. 59-60B, an end connector 970 is depicted that is suitable for attachment to the two ends 968 of a tubular filament to form an extension loop 990. This connector 970, rather than the loop material, can be held in the cavity 954 in the tip 904 of the introducer needle 903. The end connector 970 is generally U-shaped. Each leg of the U has a barbed extension 972 protruding therefrom that provides a frictional fit with a length of tubing fit thereon. Moving along either of the arms of the U and away from the curve of the U, the barbed extension has a cylindrical region 976a of first width W1, a tapered first barbed section 974a decreasing in width, followed by a cylindrical region 976b of second width W2, and a second barbed section 974b that also decreases in width until it reaches a blunt tip 978. As shown in FIG. 59, the wide end of each barbed section 974a, 974b is wider than the width of the cylindrical region 976 to which it is adjacent. This way, the end of a length of elastic tubing can be advanced over the barbed sections 974a, 974b and cylindrical regions 976 and will be deformed somewhat by the barbed regions 974a, 974b, which will then prevent the tubing from being pulled backward and away from the connector 907.

The U-shaped connector 970 can be made from any suitable biocompatible material such as plastic or metal, and preferably has a smooth and non-irritating surface finish. If desired, a low-friction coating could be applied.

Also, the connection between the U-shaped connector 970 and the tubing could be made by bonding or welding.

FIGS. 60A and 60B illustrate how an extension loop 990 formed using the U-shaped connector 970 of FIG. 59 can be captured at the tip 904 of an introducer needle 903. As shown, the introducer needle tip 904 has a "T"-shaped cavity 934 formed therein. The recess has legs which are of the right size to receive the curved portion of the U-shaped connector 970. The U-shaped connector 970 passes through the base of the "T"-shaped cavity 934 and then sits one of the two ends of the crossbar of the "T", depending upon whether the introducer needle 903 is being advanced into or withdrawn from the patient's body to position the implant member 901. As shown in FIG. 60 the introducer needle 903 will be withdrawn from the patient's body to draw the implant member 901 into place.

Alternatively, the extension loop 990 shown in FIG. 60A could be formed by joining the two ends of the filament together, say, by placing one loop end inside the other.

It also should be understood that the extension loop 990 used in FIG. 60A could be made from flat tape, solid cord, or any other suitable material.

Figure 61A:
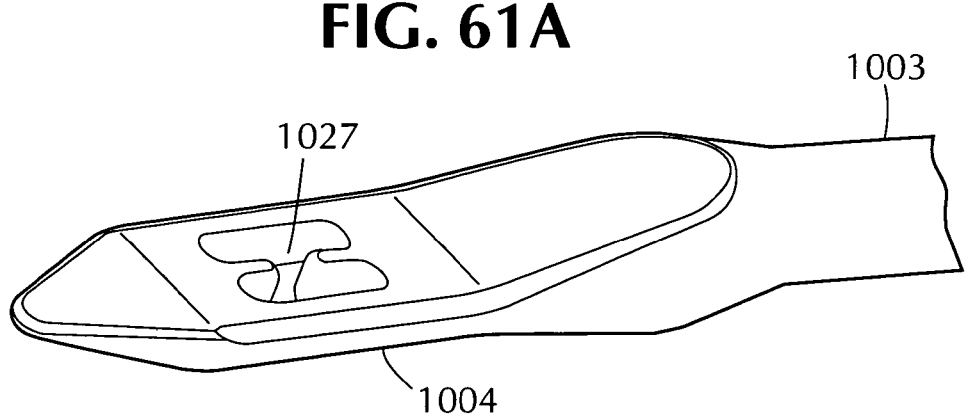
FIGS. 61A and 61B are perspective views showing another embodiment of this invention in which a loop connector is captured by an introducer needle.
Figure 61B:
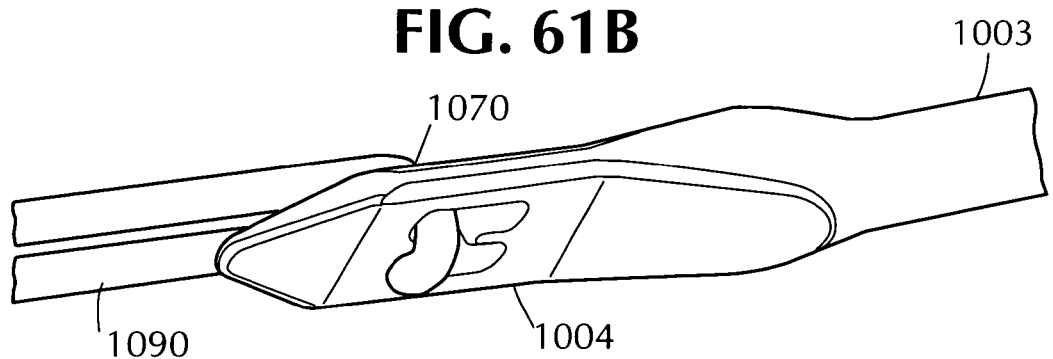

An alternate needle tip configuration for capturing the U-shaped connector is depicted in FIGS. 61A-B. Here, the tip 1004 of the needle 1003 has an "H" shaped opening 1027, the grooves forming the "H" being sized to securely receive the U-shaped connector 1070. As shown in FIG. 61B, the legs of the curved portion of the U-shaped connector 1070 fit into the ends of the long legs of the "H". The curved portion of the U-shaped connector 1070 runs from one long leg of the "H" around the solid piece separating that leg from the other long leg, and into the other leg (it will be appreciated that this embodiment may work best with a U-shaped connector 1070 made of compliant material). This arrangement securely holds the U-shaped connector 1070 in place so that the introducer needle 1003 can be retracted, drawing the extension loop 1090 and attached urethral support 1081 into the patient's body.

It will be appreciated that if the implant member 1001 is to be positioned by advancing the introducer needle 1003, then the curved portion of the U-shaped connector 1070 can be attached in the same manner as discussed above to the other ends of the long legs of the "H" shaped opening in the needle tip 1004.

Figure 62A:
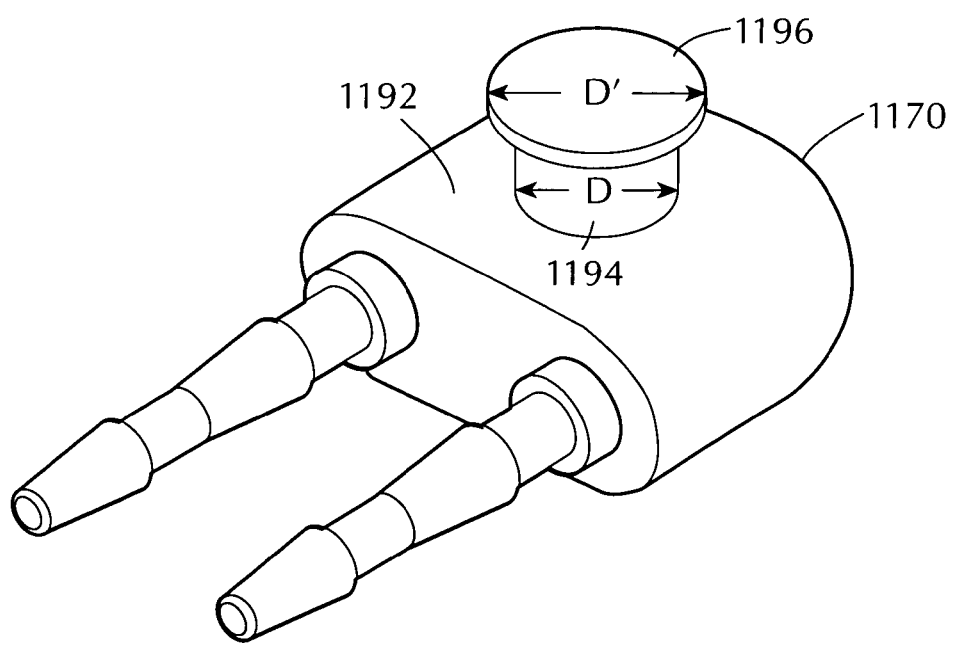
FIGS. 62A and 62B are perspective views showing another embodiment of this invention in which a loop connector has a projection that is captured by an introducer needle.
Figure 62B:
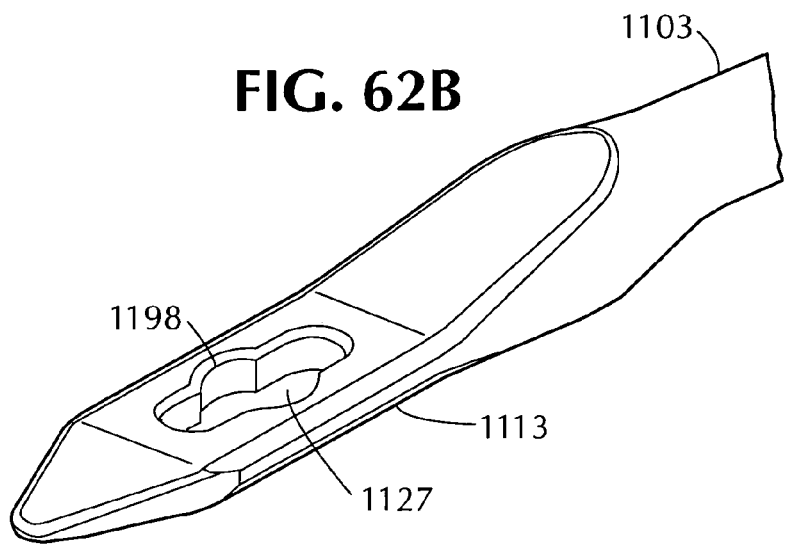

FIGS. 62A-B depict another embodiment of a U-shaped end connector 1170 that can be used to form an extension loop 1190. This U-shaped connector 1170 is generally similar to that shown in FIG. 59, but in place of the open portion of the U the connector 1170 carries a solid base portion 1192 from which extends a cylindrical projection 1194 having a diameter D. The top 1196 of the projection 1194 is enlarged and has a diameter D' that is somewhat larger than diameter D. Thus, the top portion 1196 serves as a flange.

The U-shaped connector 1170 shown in FIG. 62A is used with and is received by a needle 1103 having a slot 1127 formed therein as shown in FIG. 62B. The slot 1127 is generally rectangular, with rounded end portions and a curved opening 1198 at its center. The opening 1198 is slightly larger than the diameter D' of the top 1196 of the projection 1194 on the U-shaped connector 1170. The rest of the slot 1127 has a width that is slightly wider than the diameter D of the cylindrical projection 1194 on the U-shaped connector 1170, but which is still narrower than the diameter D' of the top 1196 of the projection 1194. This way, the U-shaped connector 1170 can be joined to the introducer needle 1103 by fitting the projection 1194 into the curved opening 1198 of the slot 1127 and then moving the U-shaped connector 1170 along the length of the slot 1127 so that the cylindrical portion 1194 rides in the slot 1127 and is held in place because the flat, spatulated section of the instrument 1113 is held between the top 1196 of the projection 1194 and the base 1192 of the U-shaped connector 1170.

Because the projection 1194 is cylindrical, it is possible for the connector 1170 to rotate in a plane which is perpendicular to the plane that the needle tip lies in.

Figure 63A:
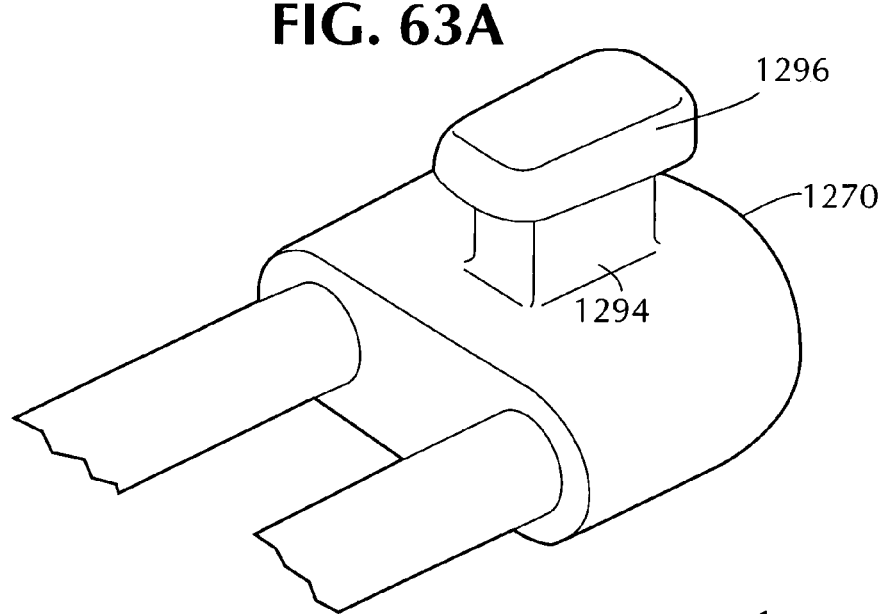
FIGS. 63A and 63B are perspective views showing another embodiment of this invention in which a loop connector has a projection that is captured by an introducer needle.
Figure 63B:
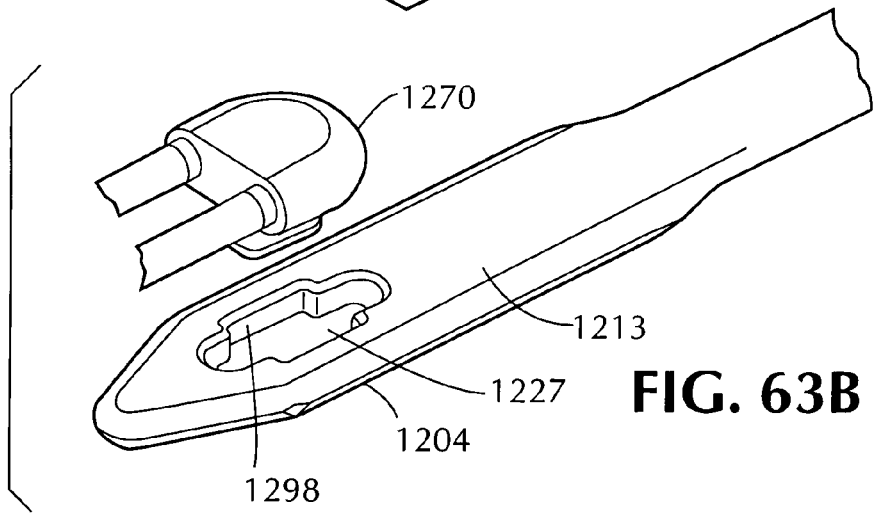

FIGS. 63A and 63B depict a modification of the embodiment shown in FIGS. 62A-B. In this structure, the U-shaped connector 1270 has an upwardly-extending rectangular projection 1294 or tab having an enlarged head region 1296. The needle tip 1204 has a generally-rectangular slot 1227 of a given width with an enlarged central opening 1298 that is dimensioned to receive the enlarged head region 1296 of the U-shaped connector 1270. As with the previous embodiment, when the U-shaped connector 1270 is moved along the slot 1227, the flat, spatulated section 1213 of the introducer needle 1203 is held between the solid base 1292 of the U-shaped connector 1270 and the enlarged head region 1296. Again, this secures the U-shaped connector 1270 to the needle.

Furthermore, the rectangular shape of the projection 1294 prevents rotation of the connector 1270 relative to the needle in a plane lying parallel to the plane in which the needle tip lies (by suitably adjusting the relative side of the tab and slot, some degree of rotation could be allowed).

Next, techniques for using this invention will be described.

The present invention can be used for implantation via either an abdominal or vaginal approach. Such versatility is a strong benefit of the invention, as it provides surgeons with the option of using whichever approach they feel most comfortable with.

In the abdominal approach, appropriate anesthesia is chosen according to the physician's preference. Then, at least one small skin nick is made in the abdominal wall at the level of the pubic symphysis, just lateral to the midline if two nicks are created. A small incision is made in the anterior vaginal wall just below the urethral meatus. If not already done, the handle is attached to the first introducer needle, and the assembly is advanced into the retropubic space via one of the abdominal incisions. The needle is further advanced downward until the needle tip is exposed at the vaginal incision. Next, a cystoscopy is performed to confirm bladder integrity. One end of the tissue implant is connected to the needle tip, preferably using the permanent snap-on tissue connector, and the introducer is withdrawn from the abdominal incision with the tissue attached. The handle is then disconnected from the first needle and attached to the second needle.

The steps starting with attachment of the handle to the needle through withdrawal of the introducer from the abdominal incision with the tissue implant attached are repeated on the contralateral side using the second needle and connector. The implant member now forms a U-shaped loop beneath the urethra, and the ends of the U are available at the abdominal incisions.

At this point the implant member is positioned loosely under the urethra by either gently tightening the strip by pulling on the abdominal ends of the implant or, if necessary, by loosening the strip by pulling on the implant with a clamp at the vaginal incision. The textured design of the implant allows it to anchor itself in the patient's own tissue, eliminating the need for suturing.

Once the appropriate implant position is achieved, the abdominal ends of the implant are cut just below the level of the skin and all incisions are closed. The introducer needles and connectors are then discarded (although the needles could be sterilized and reused, that is not presently preferred).

It should be understood that instead of using a single handle, two handles could be provided, one for each of the introducer needles.

In the vaginal approach, appropriate anesthesia is chosen according to the physician's preference and at least one small skin nick is made in the abdominal wall at the level of the pubic symphysis, just lateral to the midline if two nicks are created. A small incision is made in the anterior vaginal wall just below the urethral meatus. The handle is attached to the first introducer needle, and the introducer needle is inserted, via the vaginal incision, and advanced upward until the tip is exposed through the first abdominal incision. A cystoscopy is performed to confirm bladder integrity and the handle is disconnected from the introducer needle. One end of the tissue implant is connected at the vaginal end of the introducer via the permanent snap-on tissue connector, as shown and described in FIGS. 7A-10. The introducer is then used to draw the implant up to the first abdominal incision. The steps of attaching the handle to the introducer needle through using the introducer to draw the tissue implant up to the abdominal incision are then repeated using the second needle and connector on the patient's contralateral side. The implant member now forms a U-shaped loop under the urethra with the ends of the U available at the abdominal incisions.

The implant member is positioned loosely under the urethra by either tightening the strip with the abdominal ends of the implant or loosening the strip by pulling on the implant with a clamp at the vaginal incision. The textured design of the implant allows it to anchor itself in the patient's own tissue, eliminating the need for suturing.

Once the appropriate position is achieved, the abdominal ends of the implant are cut just below the level of the skin and all incisions are closed. The introducer needles and connectors are then discarded (again, while the needles could be sterilized for reuse, that is not presently preferred).

Again, it should be understood that instead of using a single handle, two handles could be provided, one for each of the introducer needles.

Together, the components used in this invention provide a minimally invasive, simple technique that is easily learned and which requires little operative time. The implant member will offer the low complication rate and good tissue ingrowth of a natural material, while the texturing provides the self-anchoring properties of a synthetic mesh, thereby eliminating the need for sutures or other anchoring means.

Thus, while there have been shown and described and pointed out novel features of the present invention as applied to preferred embodiments thereof, it will be understood that various omissions and substitutions and changes in the form and details of the disclosed invention may be made by those skilled in the art without departing from the spirit of the invention. It is the intention, therefore, to be limited only as indicated by the scope of the claims appended hereto.

It is also to be understood that the following claims are intended to cover all of the generic and specific features of the invention herein described and all statements of the scope of the invention which, as a matter of language, might be said to fall therebetween.

What is claimed is:

1. An introducer needle system configured to surgically introduce a urethral implant in a patient, comprising:

an integrally formed introducer needle including an elongated shaft connecting first and second flat spatulated sections, at least one of said spatulated sections having a tip, a constant width portion extending from the tip, and an opening formed in the constant width portion, the shaft including a straight portion connected to a curved portion, the first flat spatulated section connected to the curved portion by a flared section having a cross-sectional profile that covers a cross-sectional profile of the first flat spatulated section; and a handle including a housing having an elongated portion with a distal end opening dimensioned to receive and hold one of said flat spatulated sections, and an elastically-based latch portion having a projection dimensioned and disposed in the housing to engage the flat spatulated section inserted into the distal end opening of the housing to secure the handle to the introducer needle.

* * * * *